US011872276B2

(12) United States Patent
Roth et al.

(10) Patent No.: US 11,872,276 B2
(45) Date of Patent: Jan. 16, 2024

(54) ZIKA VIRUS CHIMERIC POLYEPITOPE COMPRISING NON-STRUCTURAL PROTEINS AND ITS USE IN AN IMMUNOGENIC COMPOSITION

(71) Applicants: INSTITUT PASTEUR, Paris (FR); UNIVERSIDAD EL BOSQUE, Bogota (CO)

(72) Inventors: Claude Roth, Paris (FR); Etienne Simon-Loriere, Paris (FR); Anavaj Sakuntabhai, Paris (FR); Felix Delgado, Bogota (CO)

(73) Assignees: INSTITUT PASTEUR, Paris (FR); UNIVERSIDAD EL BOSQUE, Bogota (CO)

( * ) Notice: Subject to any disclaimer, the term of this patent is extended or adjusted under 35 U.S.C. 154(b) by 117 days.

(21) Appl. No.: 17/694,440

(22) Filed: Mar. 14, 2022

(65) Prior Publication Data
US 2022/0233678 A1    Jul. 28, 2022

Related U.S. Application Data

(63) Continuation of application No. 16/762,849, filed as application No. PCT/EP2018/080677 on Nov. 8, 2018, now Pat. No. 11,305,003.

(30) Foreign Application Priority Data

Nov. 9, 2017   (EP) ..................... 17306553

(51) Int. Cl.
| A61K 39/00 | (2006.01) |
| A61K 9/00 | (2006.01) |
| A61K 39/12 | (2006.01) |
| A61K 39/295 | (2006.01) |
| A61P 31/14 | (2006.01) |
| C07K 14/005 | (2006.01) |
| C12N 7/00 | (2006.01) |

(52) U.S. Cl.
CPC ............ *A61K 39/12* (2013.01); *A61K 9/0029* (2013.01); *C07K 14/005* (2013.01); *C12N 7/00* (2013.01); *C12N 2770/24122* (2013.01); *C12N 2770/24134* (2013.01)

(58) Field of Classification Search
CPC ................ A61K 39/12; A61K 2039/53; A61K 2039/70; C12N 7/00; C12N 2770/18034
See application file for complete search history.

(56) References Cited

U.S. PATENT DOCUMENTS

2020/0282043 A1   9/2020  Roth et al.

FOREIGN PATENT DOCUMENTS

| EP | 2959915 A1 | 12/2015 |
| WO | 2015/197565 A1 | 12/2015 |
| WO | 2016/181147 A1 | 11/2016 |
| WO | 2017/189891 A1 | 11/2017 |
| WO | 2018/009603 A1 | 1/2018 |
| WO | 2018/009604 A1 | 1/2018 |
| WO | 2018/071405 A1 | 4/2018 |
| WO | 2018/176075 A1 | 10/2018 |

OTHER PUBLICATIONS

International Search Report and Written Opinion of the International Searching Authority, PCT/EP2018/080677, dated Feb. 5, 2019.
Alba Grifoni et al: "Prior Dengue Virus Exposure Shapes T Cell Immunity to Zika Viurs in Humans", Journal of Virology., vol. 91, No. 24, Dec. 15, 2017 (Dec. 15, 2017), pp. e01469-17.
Jinsheng Wen et al: "Identification of Zika virus epitopes reveals immunodominant and protective roles for dengue virus cross-reactive COB+ T cells", Nature Microbiology, vol. 2, Mar. 13, 2017 {Mar. 13, 2017), p. 17036.
Elong Ngono Annie et al: "Mapping and Role of the CDB+T Cell Response During Primary Zika Virus Infection in Mice", Cell Host & Microbe, Elsevier, NL, vol. 21, No. 1, Jan. 11, 2017 (Jan. 11, 2017), pp. 35-46.
Dar Hamza et al: "Prediction of promiscuous T-cell epitopes in the Zika virus polyprotein: Anin silicoapproach", Asian Pacific Journal of Tropical Medicine, Hainan Medical College, Singapore, vol. 9, No. 9, Jul. 26, 2016 (Jul. 26, 2016), pp. 844-850.
Pradhan Dibyabhaba et al: "Discovery of T-cell Driven Subunit Vaccines from Zika Virus Genome: An Immunoinformatics Approach", Interdisciplinary Sciences: Computational Life Sciences, International Association of Scientists in the Interdisciplinary Areas, CA, vol. 9, No. 4, Nov. 1, 2017 (Nov. 1, 2017), pp. 468-477.
Dikhit Manas R et al: "Computational prediction and analysis of potential antigenic CTL epitopes in Zika virus: A first step towards vaccine development", Infection, Genetics and Evolution, vol. 45, pp. 187-197.
Thomson S A et al: "Minimal epitopes expressed in a recombinant polyepitope protein are processed and presented to CDS+ cytotoxic T cells: implications for vaccine design", Proceedings National Academy of Sciences PNAS, National Academy of Sciences, US, vol. 92, Jun. 1, 1995 (Jun. 1, 1995), pp. 5845-5849.

(Continued)

*Primary Examiner* — Barry A Chestnut
(74) *Attorney, Agent, or Firm* — Arrigo, Lee, Guttman & Mouta-Bellum LLP

(57) ABSTRACT

The present invention is directed to a Zika virus (ZIKV) chimeric polyepitope comprising non-structural proteins and its use in an immunogenic composition. The present invention provides means, in particular polynucleotides, vectors and cells expressing said chimeric polyepitope. The present invention also relates to a composition or a vaccine comprising at least one of said polyepitope, polynucleotide, vector or host cell for use in the prevention of a ZIKV infection in a human subject, or for use in the prevention of ZIKV and dengue virus (DENV) infections in a human subject.

16 Claims, 5 Drawing Sheets

Specification includes a Sequence Listing.

(56) References Cited

OTHER PUBLICATIONS

Yun, T. et al., Identification and molecular characterization of a novel flavivirus isolated from Pekin ducklings in China, Veterinary Microbiology. 2012, 157, 3-4, 311-319.

Grard, G. et al., Genomics and evolution of Aedes-borne flaviviruses, Journal of General Virology. 2010, 91, 87-94.

Kuno, G. et al., Full-length sequencing and genomic characterization of Bagaza, Kedougou, and Zika viruses, Archives of Virology. 2007, 152, 687-696.

Jiangtao and Jianqiong. Research progress and application of the NS1 structure of the Zika Virus. Chinese Journal of Virology, 2017, 33(5), 791-797.

Fig. 4

SEQUENCE LISTING

```
<160> NUMBER OF SEQ ID NOS: 124

<210> SEQ ID NO 1
<211> LENGTH: 15
<212> TYPE: PRT
<213> ORGANISM: Artificial sequence
<220> FEATURE:
<223> OTHER INFORMATION: 15-mer epitope in the C protein of ZIKV
      (C-13-27)

<400> SEQUENCE: 1

Ile Val Asn Met Leu Lys Arg Gly Val Ala Arg Val Ser Pro Phe
1               5                   10                  15

<210> SEQ ID NO 2
<211> LENGTH: 9
<212> TYPE: PRT
<213> ORGANISM: Artificial sequence
<220> FEATURE:
<223> OTHER INFORMATION: 9-mer epitope in the C protein of ZIKV
      (C-13-27)

<400> SEQUENCE: 2

Leu Lys Arg Gly Val Ala Arg Val Ser
1               5

<210> SEQ ID NO 3
<211> LENGTH: 9
<212> TYPE: PRT
<213> ORGANISM: Artificial sequence
<220> FEATURE:
<223> OTHER INFORMATION: 9-mer predicted epitope in the C protein of
      ZIKV (C-13-27)

<400> SEQUENCE: 3

Met Leu Lys Arg Gly Val Ala Arg Val
1               5

<210> SEQ ID NO 4
<211> LENGTH: 15
<212> TYPE: PRT
<213> ORGANISM: Artificial sequence
<220> FEATURE:
<223> OTHER INFORMATION: 15-mer epitope in the C protein of ZIKV
      (C-85-99)
```

```
<400> SEQUENCE: 4

Lys Lys Asp Leu Ala Ala Met Leu Arg Ile Ile Asn Ala Arg Lys
1               5                   10                  15

<210> SEQ ID NO 5
<211> LENGTH: 9
<212> TYPE: PRT
<213> ORGANISM: Artificial sequence
<220> FEATURE:
<223> OTHER INFORMATION: 9-mer first epitope in the C protein of ZIKV
      (C-85-99)

<400> SEQUENCE: 5

Ala Ala Met Leu Arg Ile Ile Asn Ala
1               5

<210> SEQ ID NO 6
<211> LENGTH: 9
<212> TYPE: PRT
<213> ORGANISM: Artificial sequence
<220> FEATURE:
<223> OTHER INFORMATION: 9-mer second epitope in the C protein of ZIKV
      (C-85-99)

<400> SEQUENCE: 6

Lys Asp Leu Ala Ala Met Leu Arg Ile
1               5

<210> SEQ ID NO 7
<211> LENGTH: 15
<212> TYPE: PRT
<213> ORGANISM: Artificial sequence
<220> FEATURE:
<223> OTHER INFORMATION: 15-mer epitope in the E protein of ZIKV
      (E-455-469)

<400> SEQUENCE: 7

Gly Met Ser Trp Phe Ser Gln Ile Leu Ile Gly Thr Leu Leu Met
1               5                   10                  15

<210> SEQ ID NO 8
<211> LENGTH: 10
<212> TYPE: PRT
<213> ORGANISM: Artificial sequence
<220> FEATURE:
<223> OTHER INFORMATION: 10-mer predicted epitope in the E protein of
      ZIKV (E-455-469)

<400> SEQUENCE: 8

Gly Met Ser Trp Phe Ser Gln Ile Leu Ile
1               5                   10

<210> SEQ ID NO 9
<211> LENGTH: 9
<212> TYPE: PRT
<213> ORGANISM: Artificial sequence
<220> FEATURE:
<223> OTHER INFORMATION: 9-mer predicted epitope in the E protein of
      ZIKV (E-455-469)

<400> SEQUENCE: 9

Met Ser Trp Phe Ser Gln Ile Leu Ile
1               5

<210> SEQ ID NO 10
<211> LENGTH: 15
<212> TYPE: PRT
```

```
<213> ORGANISM: Artificial sequence
<220> FEATURE:
<223> OTHER INFORMATION: 15-mer epitope in the NS1 protein of ZIKV
      (NS1-63-77)

<400> SEQUENCE: 10

Met Glu Asn Ile Met Trp Arg Ser Val Glu Gly Glu Leu Asn Ala
1               5                   10                  15

<210> SEQ ID NO 11
<211> LENGTH: 9
<212> TYPE: PRT
<213> ORGANISM: Artificial sequence
<220> FEATURE:
<223> OTHER INFORMATION: 9-mer first epitope in the NS1 protein of ZIKV
      (NS1-63-77)

<400> SEQUENCE: 11

Ile Met Trp Arg Ser Val Glu Gly Glu
1               5

<210> SEQ ID NO 12
<211> LENGTH: 9
<212> TYPE: PRT
<213> ORGANISM: Artificial sequence
<220> FEATURE:
<223> OTHER INFORMATION: 9-mer second epitope in the NS1 protein of ZIKV
      (NS1-63-77)

<400> SEQUENCE: 12

Trp Arg Ser Val Glu Gly Glu Leu Asn
1               5

<210> SEQ ID NO 13
<211> LENGTH: 10
<212> TYPE: PRT
<213> ORGANISM: Artificial sequence
<220> FEATURE:
<223> OTHER INFORMATION: 10-mer predicted epitope in the NS1 protein of
      ZIKV (NS1-63-77)

<400> SEQUENCE: 13

Ile Met Trp Arg Ser Val Glu Gly Glu Leu
1               5                   10

<210> SEQ ID NO 14
<211> LENGTH: 15
<212> TYPE: PRT
<213> ORGANISM: Artificial sequence
<220> FEATURE:
<223> OTHER INFORMATION: 15-mer epitope in the NS1 protein of ZIKV
      (NS1-83-97)

<400> SEQUENCE: 14

Gly Val Gln Leu Thr Val Val Val Gly Ser Val Lys Asn Pro Met
1               5                   10                  15

<210> SEQ ID NO 15
<211> LENGTH: 9
<212> TYPE: PRT
<213> ORGANISM: Artificial sequence
<220> FEATURE:
<223> OTHER INFORMATION: 9-mer epitope in the NS1 protein of ZIKV
      (NS1-83-97)

<400> SEQUENCE: 15

Val Gln Leu Thr Val Val Val Gly Ser
1               5
```

```
<210> SEQ ID NO 16
<211> LENGTH: 10
<212> TYPE: PRT
<213> ORGANISM: Artificial sequence
<220> FEATURE:
<223> OTHER INFORMATION: 10-mer predicted epitope in the NS1 protein of
      ZIKV (NS1-83-97)

<400> SEQUENCE: 16

Val Gln Leu Thr Val Val Val Gly Ser Val
1               5                   10

<210> SEQ ID NO 17
<211> LENGTH: 15
<212> TYPE: PRT
<213> ORGANISM: Artificial sequence
<220> FEATURE:
<223> OTHER INFORMATION: 15-mer epitope in the NS1 protein of ZIKV
      (NS1-163-177)

<400> SEQUENCE: 17

Phe His Thr Ser Val Trp Leu Lys Val Arg Glu Asp Tyr Ser Leu
1               5                   10                  15

<210> SEQ ID NO 18
<211> LENGTH: 9
<212> TYPE: PRT
<213> ORGANISM: Artificial sequence
<220> FEATURE:
<223> OTHER INFORMATION: 9-mer first epitope in the NS1 protein of ZIKV
      (NS1-163-177)

<400> SEQUENCE: 18

Val Trp Leu Lys Val Arg Glu Asp Tyr
1               5

<210> SEQ ID NO 19
<211> LENGTH: 9
<212> TYPE: PRT
<213> ORGANISM: Artificial sequence
<220> FEATURE:
<223> OTHER INFORMATION: 9-mer second epitope in the NS1 protein of ZIKV
      (NS1-163-177)

<400> SEQUENCE: 19

Trp Leu Lys Val Arg Glu Asp Tyr Ser
1               5

<210> SEQ ID NO 20
<211> LENGTH: 12
<212> TYPE: PRT
<213> ORGANISM: Artificial sequence
<220> FEATURE:
<223> OTHER INFORMATION: 12-mer predicted epitope in the NS1 protein of
      ZIKV (NS1-163-177)

<400> SEQUENCE: 20

His Thr Ser Val Trp Leu Lys Val Arg Glu Asp Tyr
1               5                   10

<210> SEQ ID NO 21
<211> LENGTH: 9
<212> TYPE: PRT
<213> ORGANISM: Artificial sequence
<220> FEATURE:
<223> OTHER INFORMATION: 9-mer first predicted epitope in the NS1
      protein of ZIKV (NS1-163-177)
```

```
<400> SEQUENCE: 21

His Thr Ser Val Trp Leu Lys Val Arg
1               5

<210> SEQ ID NO 22
<211> LENGTH: 9
<212> TYPE: PRT
<213> ORGANISM: Artificial sequence
<220> FEATURE:
<223> OTHER INFORMATION: 9-mer second predicted epitope in the NS1
      protein of ZIKV (NS1-163-177)

<400> SEQUENCE: 22

Phe His Thr Ser Val Trp Leu Lys Val
1               5

<210> SEQ ID NO 23
<211> LENGTH: 15
<212> TYPE: PRT
<213> ORGANISM: Artificial sequence
<220> FEATURE:
<223> OTHER INFORMATION: 15-mer epitope in the NS1 protein of ZIKV
      (NS1-275-289)

<400> SEQUENCE: 23

Ile Arg Phe Glu Glu Cys Pro Gly Thr Lys Val His Val Glu Glu
1               5                   10                  15

<210> SEQ ID NO 24
<211> LENGTH: 9
<212> TYPE: PRT
<213> ORGANISM: Artificial sequence
<220> FEATURE:
<223> OTHER INFORMATION: 9-mer epitope in the NS1 protein of ZIKV
      (NS1-275-289)

<400> SEQUENCE: 24

Cys Pro Gly Thr Lys Val His Val Glu
1               5

<210> SEQ ID NO 25
<211> LENGTH: 15
<212> TYPE: PRT
<213> ORGANISM: Artificial sequence
<220> FEATURE:
<223> OTHER INFORMATION: 15-mer epitope in the NS2B protein of ZIKV
      (NS2B-117-131)

<400> SEQUENCE: 25

Ala Ala Gly Ala Trp Tyr Val Tyr Val Lys Thr Gly Lys Arg Ser
1               5                   10                  15

<210> SEQ ID NO 26
<211> LENGTH: 10
<212> TYPE: PRT
<213> ORGANISM: Artificial sequence
<220> FEATURE:
<223> OTHER INFORMATION: 10-mer predicted epitope in the NS2B protein of
      ZIKV (NS2B-117-131)

<400> SEQUENCE: 26

Ala Ala Gly Ala Trp Tyr Val Tyr Val Lys
1               5                   10

<210> SEQ ID NO 27
<211> LENGTH: 9
```

```
<212> TYPE: PRT
<213> ORGANISM: Artificial sequence
<220> FEATURE:
<223> OTHER INFORMATION: 9-mer predicted epitope in the NS2B protein of
      ZIKV (NS2B-117-131)

<400> SEQUENCE: 27

Tyr Val Tyr Val Lys Thr Gly Lys Arg
1               5

<210> SEQ ID NO 28
<211> LENGTH: 15
<212> TYPE: PRT
<213> ORGANISM: Artificial sequence
<220> FEATURE:
<223> OTHER INFORMATION: 15-mer epitope in the NS3 protein of ZIKV
      (NS3-219-233)

<400> SEQUENCE: 28

Thr Val Ile Leu Ala Pro Thr Arg Val Val Ala Ala Glu Met Glu
1               5                   10                  15

<210> SEQ ID NO 29
<211> LENGTH: 10
<212> TYPE: PRT
<213> ORGANISM: Artificial sequence
<220> FEATURE:
<223> OTHER INFORMATION: 10-mer epitope in the NS3 protein of ZIKV
      (NS3-219-233)

<400> SEQUENCE: 29

Ala Pro Thr Arg Val Val Ala Ala Glu Met
1               5                   10

<210> SEQ ID NO 30
<211> LENGTH: 10
<212> TYPE: PRT
<213> ORGANISM: Artificial sequence
<220> FEATURE:
<223> OTHER INFORMATION: 10-mer predicted epitope in the NS3 protein of
      ZIKV (NS3-219-233)

<400> SEQUENCE: 30

Ile Leu Ala Pro Thr Arg Val Val Ala Ala
1               5                   10

<210> SEQ ID NO 31
<211> LENGTH: 15
<212> TYPE: PRT
<213> ORGANISM: Artificial sequence
<220> FEATURE:
<223> OTHER INFORMATION: 15-mer epitope in the NS3 protein of ZIKV
      (NS3-271-285)

<400> SEQUENCE: 31

Leu Gln Pro Ile Arg Val Pro Asn Tyr Asn Leu Tyr Ile Met Asp
1               5                   10                  15

<210> SEQ ID NO 32
<211> LENGTH: 9
<212> TYPE: PRT
<213> ORGANISM: Artificial sequence
<220> FEATURE:
<223> OTHER INFORMATION: 9-mer predicted epitope in the NS3 protein of
      ZIKV (NS3-271-285)

<400> SEQUENCE: 32

Val Pro Asn Tyr Asn Leu Tyr Ile Met
```

<210> SEQ ID NO 33
<211> LENGTH: 15
<212> TYPE: PRT
<213> ORGANISM: Artificial sequence
<220> FEATURE:
<223> OTHER INFORMATION: 15-mer epitope in the NS3 protein of ZIKV
      (NS3-311-325)

<400> SEQUENCE: 33

Ala Ala Ile Phe Met Thr Ala Thr Pro Pro Gly Thr Arg Asp Ala
1               5                   10                  15

<210> SEQ ID NO 34
<211> LENGTH: 9
<212> TYPE: PRT
<213> ORGANISM: Artificial sequence
<220> FEATURE:
<223> OTHER INFORMATION: 9-mer first epitope in the NS3 protein of ZIKV
      (NS3-311-325)

<400> SEQUENCE: 34

Phe Met Thr Ala Thr Pro Pro Gly Thr
1               5

<210> SEQ ID NO 35
<211> LENGTH: 9
<212> TYPE: PRT
<213> ORGANISM: Artificial sequence
<220> FEATURE:
<223> OTHER INFORMATION: 9-mer second epitope in the NS3 protein of ZIKV
      (NS3-311-325)

<400> SEQUENCE: 35

Ile Phe Met Thr Ala Thr Pro Pro Gly
1               5

<210> SEQ ID NO 36
<211> LENGTH: 15
<212> TYPE: PRT
<213> ORGANISM: Artificial sequence
<220> FEATURE:
<223> OTHER INFORMATION: 15-mer epitope in the NS4A protein of ZIKV
      (NS4A-86-100)

<400> SEQUENCE: 36

Val Thr Leu Gly Ala Ser Ala Trp Leu Met Trp Leu Ser Glu Ile
1               5                   10                  15

<210> SEQ ID NO 37
<211> LENGTH: 10
<212> TYPE: PRT
<213> ORGANISM: Artificial sequence
<220> FEATURE:
<223> OTHER INFORMATION: 10-mer predicted epitope in the NS4A protein of
      ZIKV (NS4A-86-100)

<400> SEQUENCE: 37

Ser Ala Trp Leu Met Trp Leu Ser Glu Ile
1               5                   10

<210> SEQ ID NO 38
<211> LENGTH: 9
<212> TYPE: PRT
<213> ORGANISM: Artificial sequence
<220> FEATURE:
<223> OTHER INFORMATION: 9-mer first predicted epitope in the NS4A protein of ZIKV (NS4A-86-100)

<400> SEQUENCE: 38

Val Thr Leu Gly Ala Ser Ala Trp Leu
1               5

<210> SEQ ID NO 39
<211> LENGTH: 9
<212> TYPE: PRT
<213> ORGANISM: Artificial sequence
<220> FEATURE:
<223> OTHER INFORMATION: 9-mer second predicted epitope in the NS4A
      protein of ZIKV (NS4A-86-100)

<400> SEQUENCE: 39

Leu Gly Ala Ser Ala Trp Leu Met Trp
1               5

<210> SEQ ID NO 40
<211> LENGTH: 15
<212> TYPE: PRT
<213> ORGANISM: Artificial sequence
<220> FEATURE:
<223> OTHER INFORMATION: 15-mer epitope in the NS4B protein of ZIKV
      (NS4B-112-126)

<400> SEQUENCE: 40

Ala Ile Ile Leu Leu Val Ala His Tyr Met Tyr Leu Ile Pro Gly
1               5                   10                  15

<210> SEQ ID NO 41
<211> LENGTH: 9
<212> TYPE: PRT
<213> ORGANISM: Artificial sequence
<220> FEATURE:
<223> OTHER INFORMATION: 9-mer epitope in the NS4B protein of ZIKV
      (NS4B-112-126)

<400> SEQUENCE: 41

Ala Ile Ile Leu Leu Val Ala His Tyr
1               5

<210> SEQ ID NO 42
<211> LENGTH: 10
<212> TYPE: PRT
<213> ORGANISM: Artificial sequence
<220> FEATURE:
<223> OTHER INFORMATION: 10-mer epitope in the NS4B protein of ZIKV
      (NS4B-112-126)

<400> SEQUENCE: 42

Leu Leu Val Ala His Tyr Met Tyr Leu Ile
1               5                   10

<210> SEQ ID NO 43
<211> LENGTH: 8
<212> TYPE: PRT
<213> ORGANISM: Artificial sequence
<220> FEATURE:
<223> OTHER INFORMATION: 8-mer epitope in the NS4B protein of ZIKV
      (NS4B-112-126)

<400> SEQUENCE: 43

Leu Val Ala His Tyr Met Tyr Leu
1               5

<210> SEQ ID NO 44

```
<210> SEQ ID NO 44
<211> LENGTH: 9
<212> TYPE: PRT
<213> ORGANISM: Artificial sequence
<220> FEATURE:
<223> OTHER INFORMATION: 9-mer first predicted epitope in the NS4B
      protein of ZIKV (NS4B-112-126)

<400> SEQUENCE: 44

Leu Leu Val Ala His Tyr Met Tyr Leu
1               5

<210> SEQ ID NO 45
<211> LENGTH: 9
<212> TYPE: PRT
<213> ORGANISM: Artificial sequence
<220> FEATURE:
<223> OTHER INFORMATION: 9-mer second predicted epitope in the NS4B
      protein of ZIKV (NS4B-112-126)

<400> SEQUENCE: 45

Leu Val Ala His Tyr Met Tyr Leu Ile
1               5

<210> SEQ ID NO 46
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-13-27)

<400> SEQUENCE: 46

Lys Ala Arg Leu Asn Gln Met Ser Ala Leu Glu Phe Tyr Ser Tyr
1               5                   10                  15

<210> SEQ ID NO 47
<211> LENGTH: 9
<212> TYPE: PRT
<213> ORGANISM: Artificial sequence
<220> FEATURE:
<223> OTHER INFORMATION: 9-mer predicted epitope in the NS5 protein of
      ZIKV (NS5-13-27)

<400> SEQUENCE: 47

Met Ser Ala Leu Glu Phe Tyr Ser Tyr
1               5

<210> SEQ ID NO 48
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-293-307)

<400> SEQUENCE: 48

Trp Phe Phe Asp Glu Asn His Pro Tyr Arg Thr Trp Ala Tyr His
1               5                   10                  15

<210> SEQ ID NO 49
<211> LENGTH: 9
<212> TYPE: PRT
<213> ORGANISM: Artificial sequence
<220> FEATURE:
<223> OTHER INFORMATION: 9-mer first epitope in the NS5 protein of ZIKV
      (NS5-293-307)

<400> SEQUENCE: 49
```

```
His Pro Tyr Arg Thr Trp Ala Tyr His
1               5
```

<210> SEQ ID NO 50
<211> LENGTH: 9
<212> TYPE: PRT
<213> ORGANISM: Artificial sequence
<220> FEATURE:
<223> OTHER INFORMATION: 9-mer second epitope in the NS5 protein of ZIKV
      (NS5-293-307)

<400> SEQUENCE: 50

```
Phe Phe Asp Glu Asn His Pro Tyr Arg
1               5
```

<210> SEQ ID NO 51
<211> LENGTH: 8
<212> TYPE: PRT
<213> ORGANISM: Artificial sequence
<220> FEATURE:
<223> OTHER INFORMATION: 8-mer predicted epitope in the NS5 protein of
      ZIKV (NS5-293-307)

<400> SEQUENCE: 51

```
Phe Phe Asp Glu Asn His Pro Tyr
1               5
```

<210> SEQ ID NO 52
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-297-311)

<400> SEQUENCE: 52

```
Glu Asn His Pro Tyr Arg Thr Trp Ala Tyr His Gly Ser Tyr Glu
1               5                   10                  15
```

<210> SEQ ID NO 53
<211> LENGTH: 9
<212> TYPE: PRT
<213> ORGANISM: Artificial sequence
<220> FEATURE:
<223> OTHER INFORMATION: 9-mer first epitope in the NS5 protein of ZIKV
      (NS5-297-311)

<400> SEQUENCE: 53

```
Asn His Pro Tyr Arg Thr Trp Ala Tyr
1               5
```

<210> SEQ ID NO 54
<211> LENGTH: 9
<212> TYPE: PRT
<213> ORGANISM: Artificial sequence
<220> FEATURE:
<223> OTHER INFORMATION: 9-mer second epitope in the NS5 protein of ZIKV
      (NS5-297-311)

<400> SEQUENCE: 54

```
Tyr Arg Thr Trp Ala Tyr His Gly Ser
1               5
```

<210> SEQ ID NO 55
<211> LENGTH: 9
<212> TYPE: PRT
<213> ORGANISM: Artificial sequence
<220> FEATURE:

<223> OTHER INFORMATION: 9-mer third epitope in the NS5 protein of ZIKV
      (NS5-297-311)

<400> SEQUENCE: 55

Arg Thr Trp Ala Tyr His Gly Ser Tyr
1               5

<210> SEQ ID NO 56
<211> LENGTH: 10
<212> TYPE: PRT
<213> ORGANISM: Artificial sequence
<220> FEATURE:
<223> OTHER INFORMATION: 10-mer predicted epitope in the NS5 protein of
      ZIKV (NS5-297-311)

<400> SEQUENCE: 56

Tyr Arg Thr Trp Ala Tyr His Gly Ser Tyr
1               5                   10

<210> SEQ ID NO 57
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-345-359)

<400> SEQUENCE: 57

Thr Asp Thr Thr Pro Tyr Gly Gln Gln Arg Val Phe Lys Glu Lys
1               5                   10                  15

<210> SEQ ID NO 58
<211> LENGTH: 9
<212> TYPE: PRT
<213> ORGANISM: Artificial sequence
<220> FEATURE:
<223> OTHER INFORMATION: 9-mer epitope in the NS5 protein of ZIKV
      (NS5-345-359)

<400> SEQUENCE: 58

Thr Pro Tyr Gly Gln Gln Arg Val Phe
1               5

<210> SEQ ID NO 59
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-425-439)

<400> SEQUENCE: 59

Glu Ala Val Asn Asp Pro Arg Phe Trp Ala Leu Val Asp Lys Glu
1               5                   10                  15

<210> SEQ ID NO 60
<211> LENGTH: 9
<212> TYPE: PRT
<213> ORGANISM: Artificial sequence
<220> FEATURE:
<223> OTHER INFORMATION: 9-mer epitope in the NS5 protein of ZIKV
      (NS5-425-439)

<400> SEQUENCE: 60

Glu Ala Val Asn Asp Pro Arg Phe Trp
1               5

```
<210> SEQ ID NO 61
<211> LENGTH: 13
<212> TYPE: PRT
<213> ORGANISM: Artificial sequence
<220> FEATURE:
<223> OTHER INFORMATION: 13-mer predicted epitope in the NS5 protein of
      ZIKV (NS5-425-439)

<400> SEQUENCE: 61

Ala Val Asn Asp Pro Arg Phe Trp Ala Leu Val Asp Lys
1               5                   10

<210> SEQ ID NO 62
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-461-475)

<400> SEQUENCE: 62

Lys Lys Gln Gly Glu Phe Gly Lys Ala Lys Gly Ser Arg Ala Ile
1               5                   10                  15

<210> SEQ ID NO 63
<211> LENGTH: 12
<212> TYPE: PRT
<213> ORGANISM: Artificial sequence
<220> FEATURE:
<223> OTHER INFORMATION: 12-mer predicted epitope in the NS5 protein of
      ZIKV (NS5-461-475)

<400> SEQUENCE: 63

Gly Glu Phe Gly Lys Ala Lys Gly Ser Arg Ala Ile
1               5                   10

<210> SEQ ID NO 64
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-473-487)

<400> SEQUENCE: 64

Arg Ala Ile Trp Tyr Met Trp Leu Gly Ala Arg Phe Leu Glu Phe
1               5                   10                  15

<210> SEQ ID NO 65
<211> LENGTH: 9
<212> TYPE: PRT
<213> ORGANISM: Artificial sequence
<220> FEATURE:
<223> OTHER INFORMATION: 9-mer predicted epitope in the NS5 protein of
      ZIKV (NS5-473-487)

<400> SEQUENCE: 65

Tyr Met Trp Leu Gly Ala Arg Phe Leu
1               5

<210> SEQ ID NO 66
<211> LENGTH: 10
<212> TYPE: PRT
<213> ORGANISM: Artificial sequence
<220> FEATURE:
<223> OTHER INFORMATION: 10-mer predicted epitope in the NS5 protein of
      ZIKV (NS5-473-487)

<400> SEQUENCE: 66
```

```
Ala Ile Trp Tyr Met Trp Leu Gly Ala Arg
1               5                   10

<210> SEQ ID NO 67
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-546-560)

<400> SEQUENCE: 67

Arg Phe Asp Leu Glu Asn Glu Ala Leu Ile Thr Asn Gln Met Glu
1               5                   10                  15

<210> SEQ ID NO 68
<211> LENGTH: 9
<212> TYPE: PRT
<213> ORGANISM: Artificial sequence
<220> FEATURE:
<223> OTHER INFORMATION: 9-mer predicted epitope in the NS5 protein of
      ZIKV (NS5-546-560)

<400> SEQUENCE: 68

Asn Glu Ala Leu Ile Thr Asn Gln Met
1               5

<210> SEQ ID NO 69
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-565-579)

<400> SEQUENCE: 69

Leu Ala Leu Ala Ile Ile Lys Tyr Thr Tyr Gln Asn Lys Val Val
1               5                   10                  15

<210> SEQ ID NO 70
<211> LENGTH: 10
<212> TYPE: PRT
<213> ORGANISM: Artificial sequence
<220> FEATURE:
<223> OTHER INFORMATION: 10-mer predicted epitope in the NS5 protein of
      ZIKV (NS5-565-579)

<400> SEQUENCE: 70

Leu Ala Leu Ala Ile Ile Lys Tyr Thr Tyr
1               5                   10

<210> SEQ ID NO 71
<211> LENGTH: 9
<212> TYPE: PRT
<213> ORGANISM: Artificial sequence
<220> FEATURE:
<223> OTHER INFORMATION: 9-mer predicted epitope in the NS5 protein of
      ZIKV (NS5-565-579)

<400> SEQUENCE: 71

Ala Leu Ala Ile Ile Lys Tyr Thr Tyr
1               5

<210> SEQ ID NO 72
<211> LENGTH: 15
<212> TYPE: PRT
<213> ORGANISM: Artificial sequence
```

```
<220> FEATURE:
<223> OTHER INFORMATION: 15-mer epitope in the NS5 protein of ZIKV
      (NS5-605-619)

<400> SEQUENCE: 72

Gln Val Val Thr Tyr Ala Leu Asn Thr Phe Thr Asn Leu Val Val
1               5                   10                  15

<210> SEQ ID NO 73
<211> LENGTH: 9
<212> TYPE: PRT
<213> ORGANISM: Artificial sequence
<220> FEATURE:
<223> OTHER INFORMATION: 9-mer epitope in the NS5 protein of ZIKV
      (NS5-605-619)

<400> SEQUENCE: 73

Tyr Ala Leu Asn Thr Phe Thr Asn Leu
1               5

<210> SEQ ID NO 74
<211> LENGTH: 10
<212> TYPE: PRT
<213> ORGANISM: Artificial sequence
<220> FEATURE:
<223> OTHER INFORMATION: 10-mer predicted epitope in the NS5 protein of
      ZIKV (NS5-605-619)

<400> SEQUENCE: 74

Thr Tyr Ala Leu Asn Thr Phe Thr Asn Leu
1               5                   10

<210> SEQ ID NO 75
<211> LENGTH: 15
<212> TYPE: PRT
<213> ORGANISM: Artificial sequence
<220> FEATURE:
<223> OTHER INFORMATION: 15-mer epitope in the C protein of ZIKV
      (C-49-63)

<400> SEQUENCE: 75

Ala Ile Leu Ala Phe Leu Arg Phe Thr Ala Ile Lys Pro Ser Leu
1               5                   10                  15

<210> SEQ ID NO 76
<211> LENGTH: 15
<212> TYPE: PRT
<213> ORGANISM: Artificial sequence
<220> FEATURE:
<223> OTHER INFORMATION: 15-mer epitope in the E protein of ZIKV
      (E-67-81)

<400> SEQUENCE: 76

Asp Met Ala Ser Asp Ser Arg Cys Pro Thr Gln Gly Glu Ala Tyr
1               5                   10                  15

<210> SEQ ID NO 77
<211> LENGTH: 15
<212> TYPE: PRT
<213> ORGANISM: Artificial sequence
<220> FEATURE:
<223> OTHER INFORMATION: 15-mer epitope in the E protein of ZIKV
      (E-87-101)

<400> SEQUENCE: 77

Asp Thr Gln Tyr Val Cys Lys Arg Thr Leu Val Asp Arg Gly Trp
1               5                   10                  15
```

<210> SEQ ID NO 78
<211> LENGTH: 15
<212> TYPE: PRT
<213> ORGANISM: Artificial sequence
<220> FEATURE:
<223> OTHER INFORMATION: 15-mer epitope in the NS1 protein of ZIKV
      (NS1-19-33)

<400> SEQUENCE: 78

Val Phe Val Tyr Asn Asp Val Glu Ala Trp Arg Asp Arg Tyr Lys
1               5                   10                  15

<210> SEQ ID NO 79
<211> LENGTH: 15
<212> TYPE: PRT
<213> ORGANISM: Artificial sequence
<220> FEATURE:
<223> OTHER INFORMATION: 15-mer epitope in the NS1 protein of ZIKV
      (NS1-55-69)

<400> SEQUENCE: 79

Cys Gly Ile Ser Ser Val Ser Arg Met Glu Asn Ile Met Trp Arg
1               5                   10                  15

<210> SEQ ID NO 80
<211> LENGTH: 15
<212> TYPE: PRT
<213> ORGANISM: Artificial sequence
<220> FEATURE:
<223> OTHER INFORMATION: 15-mer epitope in the NS1 protein of ZIKV
      (NS1-91-105)

<400> SEQUENCE: 80

Gly Ser Val Lys Asn Pro Met Trp Arg Gly Pro Gln Arg Leu Pro
1               5                   10                  15

<210> SEQ ID NO 81
<211> LENGTH: 15
<212> TYPE: PRT
<213> ORGANISM: Artificial sequence
<220> FEATURE:
<223> OTHER INFORMATION: 15-mer epitope in the NS1 protein of ZIKV
      (NS1-107-121)

<400> SEQUENCE: 81

Pro Val Asn Glu Leu Pro His Gly Trp Lys Ala Trp Gly Lys Ser
1               5                   10                  15

<210> SEQ ID NO 82
<211> LENGTH: 15
<212> TYPE: PRT
<213> ORGANISM: Artificial sequence
<220> FEATURE:
<223> OTHER INFORMATION: 15-mer epitope in the NS1 protein of ZIKV
      (NS1-147-161)

<400> SEQUENCE: 82

His Arg Ala Trp Asn Ser Phe Leu Val Glu Asp His Gly Phe Gly
1               5                   10                  15

<210> SEQ ID NO 83
<211> LENGTH: 15
<212> TYPE: PRT
<213> ORGANISM: Artificial sequence
<220> FEATURE:
<223> OTHER INFORMATION: 15-mer epitope in the NS1 protein of ZIKV
      (NS1-195-209)

```
<400> SEQUENCE: 83

His Ser Asp Leu Gly Tyr Trp Ile Glu Ser Glu Lys Asn Asp Thr
1               5                   10                  15

<210> SEQ ID NO 84
<211> LENGTH: 15
<212> TYPE: PRT
<213> ORGANISM: Artificial sequence
<220> FEATURE:
<223> OTHER INFORMATION: 15-mer epitope in the NS3 protein of ZIKV
      (NS3-131-145)

<400> SEQUENCE: 84

Pro Ala Gly Thr Ser Gly Ser Pro Ile Leu Asp Lys Cys Gly Arg
1               5                   10                  15

<210> SEQ ID NO 85
<211> LENGTH: 15
<212> TYPE: PRT
<213> ORGANISM: Artificial sequence
<220> FEATURE:
<223> OTHER INFORMATION: 15-mer epitope in the NS3 protein of ZIKV
      (NS3-143-157)

<400> SEQUENCE: 85

Cys Gly Arg Val Ile Gly Leu Tyr Gly Asn Gly Val Val Ile Lys
1               5                   10                  15

<210> SEQ ID NO 86
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-325-339)

<400> SEQUENCE: 86

Val Val Arg Leu Leu Ser Lys Pro Trp Asp Val Val Thr Gly Val
1               5                   10                  15

<210> SEQ ID NO 87
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-373-387)

<400> SEQUENCE: 87

Gln Val Met Ser Met Val Ser Ser Trp Leu Trp Lys Glu Leu Gly
1               5                   10                  15

<210> SEQ ID NO 88
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-465-479)

<400> SEQUENCE: 88

Glu Phe Gly Lys Ala Lys Gly Ser Arg Ala Ile Trp Tyr Met Trp
1               5                   10                  15

<210> SEQ ID NO 89
<211> LENGTH: 15
<212> TYPE: PRT
```

```
<213> ORGANISM: Artificial sequence
<220> FEATURE:
<223> OTHER INFORMATION: 15-mer epitope in the NS5 protein of ZIKV
      (NS5-481-495)

<400> SEQUENCE: 89

Gly Ala Arg Phe Leu Glu Phe Glu Ala Leu Gly Phe Leu Asn Glu
1               5                   10                  15

<210> SEQ ID NO 90
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-573-586)

<400> SEQUENCE: 90

Thr Tyr Gln Asn Lys Val Val Lys Val Leu Arg Pro Ala Glu Lys
1               5                   10                  15

<210> SEQ ID NO 91
<211> LENGTH: 15
<212> TYPE: PRT
<213> ORGANISM: Artificial sequence
<220> FEATURE:
<223> OTHER INFORMATION: 15-mer epitope in the NS5 protein of ZIKV
      (NS5-849-863)

<400> SEQUENCE: 91

Cys Gly Ser Leu Ile Gly His Arg Pro Arg Thr Thr Trp Ala Glu
1               5                   10                  15

<210> SEQ ID NO 92
<211> LENGTH: 15
<212> TYPE: PRT
<213> ORGANISM: Artificial sequence
<220> FEATURE:
<223> OTHER INFORMATION: 15-mer epitope in the C protein of ZIKV
      (C-21-35)

<400> SEQUENCE: 92

Val Ala Arg Val Ser Pro Phe Gly Gly Leu Lys Arg Leu Pro Ala
1               5                   10                  15

<210> SEQ ID NO 93
<211> LENGTH: 11
<212> TYPE: PRT
<213> ORGANISM: Artificial sequence
<220> FEATURE:
<223> OTHER INFORMATION: 11-mer epitope in the C protein of ZIKV
      (C-25-35)

<400> SEQUENCE: 93

Ser Pro Phe Gly Gly Leu Lys Arg Leu Pro Ala
1               5                   10

<210> SEQ ID NO 94
<211> LENGTH: 9
<212> TYPE: PRT
<213> ORGANISM: Artificial sequence
<220> FEATURE:
<223> OTHER INFORMATION: 9-mer epitope in the NS3 protein of ZIKV

<400> SEQUENCE: 94

Phe Pro Asp Ser Asn Ser Pro Ile Met
1               5
```

<210> SEQ ID NO 95
<211> LENGTH: 15
<212> TYPE: PRT
<213> ORGANISM: Artificial sequence
<220> FEATURE:
<223> OTHER INFORMATION: 15-mer epitope in the NS4B protein of ZIKV

<400> SEQUENCE: 95

Arg Gly Ser Tyr Leu Ala Gly Ala Ser Leu Ile Tyr Thr Val Thr
1               5                   10                  15

<210> SEQ ID NO 96
<211> LENGTH: 11
<212> TYPE: PRT
<213> ORGANISM: Artificial sequence
<220> FEATURE:
<223> OTHER INFORMATION: 11-mer epitope in the NS5 protein

<400> SEQUENCE: 96

Asn Gln Met Ser Ala Leu Glu Phe Tyr Ser Tyr
1               5                   10

<210> SEQ ID NO 97
<211> LENGTH: 9
<212> TYPE: PRT
<213> ORGANISM: Artificial sequence
<220> FEATURE:
<223> OTHER INFORMATION: 9-mer epitope contained in the NS5 protein
      (NS5-331-339)

<400> SEQUENCE: 97

Lys Pro Trp Asp Val Val Thr Gly Val
1               5

<210> SEQ ID NO 98
<211> LENGTH: 9
<212> TYPE: PRT
<213> ORGANISM: Artificial sequence
<220> FEATURE:
<223> OTHER INFORMATION: 9-mer epitope in the NS5 protein

<400> SEQUENCE: 98

Lys Pro Trp Asp Val Ile Pro Met Val
1               5

<210> SEQ ID NO 99
<211> LENGTH: 962
<212> TYPE: PRT
<213> ORGANISM: Artificial sequence
<220> FEATURE:
<223> OTHER INFORMATION: Amino acid sequence of a chimeric polyepitope
      of ZIKV

<400> SEQUENCE: 99

Gly Gly Phe Arg Ile Val Asn Met Leu Lys Arg Gly Val Ala Arg Val
1               5                   10                  15

Ser Pro Phe Gly Gly Leu Lys Arg Leu Pro Ala Gly Leu Leu Leu Gly
                20                  25                  30

His Gly Pro Ile Arg Met Val Leu Ala Ile Leu Ala Phe Leu Arg Phe
            35                  40                  45

Thr Ala Ile Lys Pro Ser Leu Gly Leu Ile Asn Arg Trp Gly Ser Val
        50                  55                  60

Gly Lys Lys Glu Ala Met Glu Ile Ile Lys Lys Phe Lys Lys Asp Leu
65                  70                  75                  80

```
Ala Ala Met Leu Arg Ile Ile Asn Ala Arg Lys Glu Lys Val Phe Val
                85                  90                  95

Tyr Asn Asp Val Glu Ala Trp Arg Asp Arg Tyr Lys Tyr His Pro Asp
            100                 105                 110

Ser Pro Arg Arg Leu Ala Ala Val Lys Gln Ala Trp Glu Asp Gly
        115                 120                 125

Ile Cys Gly Ile Ser Ser Val Ser Arg Met Glu Asn Ile Met Trp Arg
    130                 135                 140

Ser Val Glu Gly Glu Leu Asn Ala Ile Leu Glu Glu Asn Gly Val Gln
145                 150                 155                 160

Leu Thr Val Val Gly Ser Val Lys Asn Pro Met Trp Arg Gly Pro
                165                 170                 175

Gln Arg Leu Pro Val Pro Val Asn Glu Leu Pro His Gly Trp Lys Ala
            180                 185                 190

Trp Gly Lys Ser Tyr Phe Val Arg Ala Ala Lys Thr Asn Asn His Arg
        195                 200                 205

Ala Trp Asn Ser Phe Leu Val Glu Asp His Gly Phe Gly Val Phe His
    210                 215                 220

Thr Ser Val Trp Leu Lys Val Arg Glu Asp Tyr Ser Leu Glu Cys Asp
225                 230                 235                 240

Pro Ala Val Ile Gly Thr Ala Val Lys Gly Lys Glu Ala Val His Ser
                245                 250                 255

Asp Leu Gly Tyr Trp Ile Glu Ser Glu Lys Asn Asp Thr Trp Ile Arg
            260                 265                 270

Phe Glu Glu Cys Pro Gly Thr Lys Val His Val Glu Glu Thr Ile Phe
        275                 280                 285

Lys Thr Lys Asp Gly Asp Ile Gly Ala Val Ala Leu Asp Tyr Pro Ala
    290                 295                 300

Gly Thr Ser Gly Ser Pro Ile Leu Asp Lys Cys Gly Arg Val Ile Gly
305                 310                 315                 320

Leu Tyr Gly Asn Gly Val Val Ile Lys Asn Gly Lys Thr Arg Arg Val
                325                 330                 335

Leu Pro Glu Ile Val Arg Glu Ala Ile Lys Thr Arg Leu Arg Thr Val
            340                 345                 350

Ile Leu Ala Pro Thr Arg Val Val Ala Ala Glu Met Glu Glu Ala Leu
        355                 360                 365

Arg Gly Leu Pro Val Arg Tyr Met Thr Thr Ala Val Asn Val Thr His
    370                 375                 380

Ser Gly Thr Glu Ile Val Asp Leu Met Cys His Ala Thr Phe Thr Ser
385                 390                 395                 400

Arg Leu Leu Gln Pro Ile Arg Val Pro Asn Tyr Asn Leu Tyr Ile Met
                405                 410                 415

Asp Glu Ala His Phe Thr Asp Pro Ser Ser Ile Ala Ala Arg Gly Tyr
            420                 425                 430

Ile Ser Thr Arg Val Glu Met Gly Glu Ala Ala Ile Phe Met Thr
        435                 440                 445

Ala Thr Pro Pro Gly Thr Arg Asp Ala Phe Pro Asp Ser Asn Ser Pro
    450                 455                 460

Ile Met Asp Thr Glu Val Glu Val Pro Gln Ala Gly Val Leu Phe Gly
465                 470                 475                 480

Met Gly Lys Gly Met Pro Phe Tyr Ala Trp Asp Phe Gly Val Pro Leu
                485                 490                 495

Leu Met Ile Gly Cys Tyr Ser Gln Leu Thr Pro Leu Thr Leu Ile Val
```

```
            500                 505                 510
Ala Ile Ile Leu Leu Val Ala His Tyr Met Tyr Leu Ile Pro Gly Leu
            515                 520                 525
Gln Ala Ala Ala Ala Arg Ala Ala Gln Lys Arg Thr Ala Ala Gly Ile
            530                 535                 540
Met Lys Asn Ile Ile Gly Asn Arg Ile Glu Arg Ile Arg Ser Glu His
545                 550                 555                 560
Ala Glu Thr Trp Phe Phe Asp Glu Asn His Pro Tyr Arg Thr Trp Ala
            565                 570                 575
Tyr His Gly Ser Tyr Glu Ala Pro Thr Gln Gly Ser Ala Ser Ser Leu
            580                 585                 590
Ile Asn Gly Val Val Arg Leu Leu Ser Lys Pro Trp Asp Val Val Thr
            595                 600                 605
Gly Val Thr Gly Ile Ala Met Thr Asp Thr Thr Pro Tyr Gly Gln Gln
            610                 615                 620
Arg Val Phe Lys Glu Lys Val Asp Thr Arg Val Pro Asp Pro Gln Glu
625                 630                 635                 640
Gly Thr Arg Gln Val Met Ser Met Val Ser Ser Trp Leu Trp Lys Glu
            645                 650                 655
Leu Gly Lys His Lys Arg Pro Arg Val Cys Thr Lys Glu Glu Phe Ile
            660                 665                 670
Asn Lys Val Arg Ser Asn Ala Ala Leu Gly Ala Ile Phe Glu Glu Glu
            675                 680                 685
Lys Glu Trp Lys Thr Ala Val Glu Ala Val Asn Asp Pro Arg Phe Trp
            690                 695                 700
Ala Leu Val Asp Lys Glu Arg Glu His His Leu Arg Gly Glu Cys Gln
705                 710                 715                 720
Ser Cys Val Tyr Asn Met Met Gly Lys Arg Glu Lys Lys Gln Gly Glu
            725                 730                 735
Phe Gly Lys Ala Lys Gly Ser Arg Ala Ile Trp Tyr Met Trp Leu Gly
            740                 745                 750
Ala Arg Phe Leu Glu Phe Glu Ala Leu Gly Phe Leu Asn Glu Arg Phe
            755                 760                 765
Asp Leu Glu Asn Glu Ala Leu Ile Thr Asn Gln Met Glu Lys Gly His
            770                 775                 780
Arg Ala Leu Ala Leu Ala Ile Ile Lys Tyr Thr Tyr Gln Asn Lys Val
785                 790                 795                 800
Val Lys Val Leu Arg Pro Ala Glu Lys Gly Lys Thr Val Met Asp Ile
            805                 810                 815
Ile Ser Arg Gln Asp Met Glu Ala Glu Glu Val Leu Glu Met Gln Asp
            820                 825                 830
Leu Trp Leu Leu Arg Arg Ser Lys Pro Ser Thr Gly Trp Asp Asn Trp
            835                 840                 845
Glu Glu Val Pro Phe Cys Ser His His Phe Asn Lys Leu His Leu Lys
            850                 855                 860
Asp Gly Arg Ser Ile Val Val Pro Cys Arg His Gln Asp Glu Leu Ile
865                 870                 875                 880
Gly Arg Ala Arg Val Ser Pro Gly Ala Gly Trp Ser Ile Arg Glu Thr
            885                 890                 895
Ala Cys Leu Ala Lys Ser Tyr Ala Gln Met Trp Gln Leu Leu Tyr Phe
            900                 905                 910
His Arg Arg Asp Leu Arg Leu Met Ala Asn Ala Ile Cys Ser Ser Val
            915                 920                 925
```

```
Pro Val Asp Trp Val Pro Thr Gly Arg Thr Thr Trp Ser Ile His Gly
    930                 935                 940

Lys Gly Glu Trp Met Thr Thr Glu Asp Met Leu Val Val Trp Asn Arg
945                 950                 955                 960

Val Trp

<210> SEQ ID NO 100
<211> LENGTH: 2886
<212> TYPE: DNA
<213> ORGANISM: Artificial sequence
<220> FEATURE:
<223> OTHER INFORMATION: Native nucleotide sequence of the
      polynucleotide encoding a chimeric polyepitope of ZIKV

<400> SEQUENCE: 100
ggaggattcc ggattgtcaa tatgctaaaa cgcggagtag cccgtgtgag cccctttggg    60
ggcttgaaga ggctgccagc cggacttctg ctgggtcatg gcccatcag gatggtcttg    120 gcgattctag ccttttgag attcacggca atcaagccat cactgggtct catcaataga    180 tgggttcag tgggaaaaa agaggctatg gaaataataa agaagttcaa gaaagatctg    240
gctgccatgc tgagaataat caatgctagg aaggagaagg tgttcgtcta acgacgtt    300 gaagcctgga gggacaggta caagtaccat cctgactccc ccgtagatt ggcagcagca    360 gtcaagcaag cctgggaaga tggtatctgc gggatctcct ctgtttcaag aatggaaaac    420
atcatgtgga gatcagtaga aggggagctc aacgcaatcc tggaagagaa tggagttcaa    480
ctgacggtcg ttgtgggatc tgtaaaaac cccatgtgga gaggtccaca gagattgccc    540
gtgcctgtga acgagctgcc ccacggctgg aaggcttggg ggaaatcgta cttcgtcaga    600
gcagcaaaga caaataacca tagagcatgg aacagctttc ttgtgggagg tcatgggttc    660
ggggtatttc acactagtgt ctggctcaag gttagagaag attattcatt agagtgtgat    720
ccagccgtta ttggaacagc tgttaaggga aaggaggctg tacacagtga tctaggctac    780
tggattgaga gtgagaagaa tgacacatgg attcggtttg aggaatgccc aggcactaag    840
gtccacgtgg aggaaacaat atttaagaca aaggatgggg acattggagc ggttgcgctg    900
gattacccag caggaacttc aggatctcca atcctagaca gtgtgggag agtgatagga    960 ctttatggca atgggtcgt gatcaaaaat gggaaaacca ggagagttct tcctgaaata    1020
gtccgtgaag ccataaaaac aagactccgt actgtgatct agctccaac cagggttgtc    1080 gctgctgaaa tggaggaagc ccttagaggg cttccagtgc gttatatgac aacagcagtc    1140
aatgtcaccc actctggaac agaaatcgtc gacttaatgt gccatgccac cttcacttca    1200
cgtctactac agccaatcag agtccccaac tataatctgt atattatgga tgaggcccac    1260
ttcacagatc cctcaagtat agcagcaaga ggatacattt caacaagggt tgagatgggc    1320
gaggcggctg ccatcttcat gaccgccacg ccaccaggaa cccgtgacgc atttccggac    1380
tccaactcac caattatgga caccgaagtg gaagtcccac aagctggagt gttgtttggt    1440
atgggcaaag gatgccatt ctacgcatgg gactttggag tcccgctgct aatgataggt    1500
tgctactcac aattaacacc cctgacccta atagtggcca tcattttgct cgtggcgcac    1560
tacatgtact tgatcccagg gctgcaggca gcagctgcgc gtgctgccca gaagagaacg    1620
gcagctggca tcatgaagaa catcattggt aaccgcattg aaaggatccg cagtgagcac    1680
gcggaaacgt ggttctttga cgagaaccac ccatatagga catgggctta ccatggaagc    1740
tatgaggccc ccacacaagg gtcagcgtcc tctctaataa acggggttgt caggctcctg    1800
```

```
tcaaaaccct gggatgtggt gactggagtc acaggaatag ccatgaccga caccacaccg   1860
tatggtcagc aaagagtttt caaggaaaaa gtggacacta gggtgccaga cccccaagaa   1920
ggcactcgtc aggttatgag catggtctct tcctggttgt ggaaagagct aggcaaacac   1980
aaacggccac gagtctgtac caaagaagag ttcatcaaca aggttcgtag caatgcagca   2040 ttagggcaa tatttgaaga ggaaaaagag tggaagactg cagtggaagc tgtgaacgat    2100
ccaaggttct gggctctagt ggacaaggaa agagagcacc acctgagagg agagtgccag   2160
agttgtgtgt acaacatgat gggaaaaaga gaaagaaac aaggggaatt tggaaaggcc    2220
aagggcagcc gcgccatctg gtatatgtgg ctaggggcta gatttctaga gttcgaagcc   2280
cttggattct tgaacgagag gtttgatctg gagaatgaag ctctaatcac caaccaaatg   2340
gagaaagggc acagggcctt ggcattggcc ataatcaagt acacatacca aaacaaagtg   2400
gtaaaggtcc ttagaccagc tgaaaaaggg aaaacagtta tggacattat tcgagacaa   2460 gacatggagg ctgaggaagt tctagagatg caagacttgt ggctgctgcg gaggtcaaaa   2520
ccctcaactg gatgggacaa ctgggaagaa gttccgtttt gctcccacca cttcaacaag   2580
ctccatctca aggacgggag gtccattgtg gttccctgcc gccaccaaga tgaactgatt   2640
ggccgggccc gcgtctctcc aggggcggga tgagcatcc gggagactgc ttgcctagca    2700
aaatcatatg cgcaaatgtg gcagctcctt tatttccaca aagggaccct ccgactgatg   2760
gccaatgcca tttgttcatc tgtgccagtt gactgggttc aactgggag aactacctgg    2820 tcaatccatg gaaagggaga atggatgacc actgaagaca tgcttgtggt gtggaacaga   2880
gtgtgg                                                                2886
```

<210> SEQ ID NO 101
<211> LENGTH: 2886
<212> TYPE: DNA
<213> ORGANISM: Artificial sequence
<220> FEATURE:
<223> OTHER INFORMATION: Optimised nucleotide sequence of the
      polynucleotide encoding a chimeric polyepitope of ZIKV

<400> SEQUENCE: 101

```
ggcggcttca gaatcgtgaa catgctgaag cgcggcgtgg ccagagtgtc tccatttggc     60
ggactgaaga gactgcctgc cggactgctt ctcggacacg gccctattag aatggtgctg   120
gccatcctgg cctttctgcg gttcacagcc atcaagccta gcctgggcct gatcaacaga   180
tggggcagcg tgggcaagaa gaagccatg gaaatcatca gaagttcaa gaaagacctg    240 gccgccatgc tgcggatcat caacgcccgg aaagaaaagg tgttcgtgta caacgacgtg   300
gaagcctggc gggacagata caagtatcac cctgacagcc ccagacggct ggccgctgct   360
gtgaaacaag cttgggagga tggcatctgc ggcatcagca gcgtgtcccg gatggaaaac   420
atcatgtggc ggagcgtgga aggcgagctg aacgccattc tggaagagaa cggcgtgcag   480
ctgacagtgg ttgtgggctc cgtgaagaac cctatgtggc gggacctca gagactcccc   540 gtgcctgtta atgagctgcc tcacggatgg aaggcctggg gcaagagcta ttttgtgcgg   600
gctgccaaga ccaacaacca cagagcctgg aacagcttcc tggtggaaga tcacggcttc   660
ggcgtgttcc acacaagcgt gtggctgaaa gtgcgcgagg actacagcct ggaatgcgac   720
cctgccgtga ttggcacagc cgtgaaggga aagaagccg tgcacagcga tctcggctac   780
tggatcgaga gcgagaagaa cgacacctgg atcagattcg aggaatgccc cggcaccaag   840
gtgcacgtgg aagagacaat cttcaagacc aaggacggcg acatcggcgc cgtggctctt   900
```

```
gattatcctg ccggcacatc tggcagcccc atcctggata agtgcggcag agtgatcggc    960
ctgtacggca atggcgtcgt gatcaagaac ggcaagacca gaagagtgct gcccgagatt   1020
gtgcgggaag ccattaagac ccggctgcgg acagtgattc tggcccctac aagagtggtg   1080
gccgccgaga tggaagaagc cctgagagga ctgcctgtgc ggtacatgac aaccgccgtg   1140
aatgtgaccc cagcggcac cgaaatcgtg acctgatgt gccacgccac cttcacctct   1200
agactgctgc agcccatcag agtgcccaac tacaacctgt acatcatgga cgaggcccac   1260
ttcacagacc ccagctctat tgccgccaga ggctacatca gcaccagagt ggaaatgggc   1320
gaagccgccg ctatcttcat gaccgctaca ccacctggca ccagggacgc ctttccagac   1380
agcaacagcc ctatcatgga caccgaggtg gaagtgcctc aggccggcgt tctgtttggc   1440
atgggaaagg gcatgccatt ctacgcctgg gatttcggcg tgcccctgct gatgatcggc   1500
tgttactctc agctgacccc tctgacactg atcgtggcca tcattctgct ggtggcccac   1560
tacatgtatc tgatccctgg actgcaggcc gctgccgcta gagctgctca gaaaagaaca   1620
gccgccggaa tcatgaagaa catcatcggc aaccggatcg agcggatcag aagcgagcac   1680
gccgagacat ggttcttcga cgagaatcac ccctaccgga cctgggccta ccacggctct   1740
tatgaagctc ctacacaggg cagcgccagc agcctgatta acggcgttgt cagactgctg   1800
agcaagccct gggatgtcgt gacaggcgtg accggaatcg ccatgaccga cacaacacct   1860
tacggccagc agcgggtgtt caaagaaaaa gtggacacca gggtgcccga tcctcaagag   1920
ggcaccagac aagtgatgag catggtgtcc agctggctgt ggaaagagct gggcaagcac   1980
aagaggccca gagtgtgcac aaaagaggaa ttcatcaaca aagtgcggag caacgccgct   2040
ctgggcgcca tctttgagga agagaaagaa tggaaaaccg ccgtcgaggc cgtgaacgac   2100
cctagatttt gggccctcgt ggacaaagag agagcacc acctgagagg cgagtgccag   2160
agctgcgtgt acaatatgat gggcaaacgc gagaaaaagc agggcgagtt cggcaaggcc   2220
aagggcagta gagccatctg gtacatgtgg ctgggagcca gattcctgga attcgaggcc   2280
ctgggcttcc tgaacgagag attcgacctg gaaaatgagg ccctgatcac caaccagatg   2340
gaaaagggac acagagccct ggctctggcc attatcaagt acacctacca gaacaaggtg   2400
gtcaaggtgc tgcggcctgc cgagaagggc aagacagtga tggacatcat ctcccggcag   2460
gacatggaag ccgaagaggt gctggaaatg caggacctgt ggctgctgag aagaagcaag   2520
ccaagcaccg gctgggacaa ctgggaagaa gtgcccttct gcagccacca cttcaacaag   2580
ctgcacctga aggacggccg gtccatcgtg gtgccttgta gacaccagga cgagctgatc   2640
ggcagagcta gagtttctcc tggcgccgga tggtccatca gagagacagc ctgtctggcc   2700
aagagctacg cccagatgtg gcagctgctg tacttccaca cagggacct gagactgatg   2760 gccaacgcca tctgtagcag cgtgccagtg gattgggtgc aaccggcag aaccacctgg   2820 tccattcatg gcaaaggcga gtggatgacc accgaggaca tgctggtcgt gtggaataga   2880
gtgtgg                                                              2886
```

<210> SEQ ID NO 102
<211> LENGTH: 93
<212> TYPE: PRT
<213> ORGANISM: Artificial sequence
<220> FEATURE:
<223> OTHER INFORMATION: Amino acid sequence of a fragment of the C protein in the chimeric polyepitope of ZIKV

<400> SEQUENCE: 102

```
Gly Gly Phe Arg Ile Val Asn Met Leu Lys Arg Gly Val Ala Arg Val
1               5                   10                  15

Ser Pro Phe Gly Gly Leu Lys Arg Leu Pro Ala Gly Leu Leu Leu Gly
            20                  25                  30

His Gly Pro Ile Arg Met Val Leu Ala Ile Leu Ala Phe Leu Arg Phe
            35                  40                  45

Thr Ala Ile Lys Pro Ser Leu Gly Leu Ile Asn Arg Trp Gly Ser Val
        50                  55                  60

Gly Lys Lys Glu Ala Met Glu Ile Ile Lys Lys Phe Lys Lys Asp Leu
65                  70                  75                  80

Ala Ala Met Leu Arg Ile Ile Asn Ala Arg Lys Glu Lys
                85                  90
```

<210> SEQ ID NO 103
<211> LENGTH: 279
<212> TYPE: DNA
<213> ORGANISM: Artificial sequence
<220> FEATURE:
<223> OTHER INFORMATION: Native nucleotide sequence of the
      polynucleotide encoding a fragment of the C protein in the
      chimeric polyepitope of ZIKV

<400> SEQUENCE: 103

```
ggaggattcc ggattgtcaa tatgctaaaa cgcggagtag cccgtgtgag cccctttggg      60
ggcttgaaga ggctgccagc cggacttctg ctgggtcatg ggcccatcag gatggtcttg     120
gcgattctag cctttttgag attcacggca atcaagccat cactgggtct catcaataga     180
tggggttcag tggggaaaaa agaggctatg gaaataataa agaagttcaa gaaagatctg     240
gctgccatgc tgagaataat caatgctagg aaggagaag                            279
```

<210> SEQ ID NO 104
<211> LENGTH: 113
<212> TYPE: PRT
<213> ORGANISM: Artificial sequence
<220> FEATURE:
<223> OTHER INFORMATION: Amino acid sequence of a fragment of the NS1
      protein in the chimeric polyepitope of ZIKV

<400> SEQUENCE: 104

```
Val Phe Val Tyr Asn Asp Val Glu Ala Trp Arg Asp Arg Tyr Lys Tyr
1               5                   10                  15

His Pro Asp Ser Pro Arg Arg Leu Ala Ala Ala Val Lys Gln Ala Trp
            20                  25                  30

Glu Asp Gly Ile Cys Gly Ile Ser Ser Val Ser Arg Met Glu Asn Ile
            35                  40                  45

Met Trp Arg Ser Val Glu Gly Glu Leu Asn Ala Ile Leu Glu Glu Asn
        50                  55                  60

Gly Val Gln Leu Thr Val Val Gly Ser Val Lys Asn Pro Met Trp
65                  70                  75                  80

Arg Gly Pro Gln Arg Leu Pro Val Pro Val Asn Glu Leu Pro His Gly
                85                  90                  95

Trp Lys Ala Trp Gly Lys Ser Tyr Phe Val Arg Ala Ala Lys Thr Asn
            100                 105                 110

Asn
```

<210> SEQ ID NO 105
<211> LENGTH: 339
<212> TYPE: DNA

<213> ORGANISM: Artificial sequence
<220> FEATURE:
<223> OTHER INFORMATION: Native nucleotide sequence of the
      polynucleotide encoding a fragment of the NS1 protein in the
      chimeric polyepitope of ZIKV

<400> SEQUENCE: 105

```
gtgttcgtct ataacgacgt tgaagcctgg agggacaggt acaagtacca tcctgactcc      60
ccccgtagat tggcagcagc agtcaagcaa gcctgggaag atggtatctg cgggatctcc     120
tctgtttcaa gaatggaaaa catcatgtgg agatcagtag aaggggagct caacgcaatc     180
ctggaagaga atggagttca actgacggtc gttgtgggat ctgtaaaaaa ccccatgtgg     240
agaggtccac agagattgcc cgtgcctgtg aacgagctgc cccacggctg gaaggcttgg     300
gggaaatcgt acttcgtcag agcagcaaag acaaataac                            339
```

<210> SEQ ID NO 106
<211> LENGTH: 64
<212> TYPE: PRT
<213> ORGANISM: Artificial sequence
<220> FEATURE:
<223> OTHER INFORMATION: Amino acid sequence of a second fragment of the
      NS1 protein in the chimeric polyepitope of ZIKV

<400> SEQUENCE: 106

```
His Arg Ala Trp Asn Ser Phe Leu Val Glu Asp His Gly Phe Gly Val
1               5                   10                  15

Phe His Thr Ser Val Trp Leu Lys Val Arg Glu Asp Tyr Ser Leu Glu
                20                  25                  30

Cys Asp Pro Ala Val Ile Gly Thr Ala Val Lys Gly Lys Glu Ala Val
            35                  40                  45

His Ser Asp Leu Gly Tyr Trp Ile Glu Ser Glu Lys Asn Asp Thr Trp
        50                  55                  60
```

<210> SEQ ID NO 107
<211> LENGTH: 192
<212> TYPE: DNA
<213> ORGANISM: Artificial sequence
<220> FEATURE:
<223> OTHER INFORMATION: Native nucleotide sequence of the
      polynucleotide encoding a second fragment of the NS1 protein in
      the chimeric polyepitope of ZIKV

<400> SEQUENCE: 107

```
catagagcat ggaacagctt tcttgtggag gatcatgggt tcggggtatt tcacactagt      60
gtctggctca aggttagaga agattattca ttagagtgtg atccagccgt tattggaaca     120
gctgttaagg gaaaggaggc tgtacacagt gatctaggct actggattga gagtgagaag     180
aatgacacat gg                                                         192
```

<210> SEQ ID NO 108
<211> LENGTH: 16
<212> TYPE: PRT
<213> ORGANISM: Artificial sequence
<220> FEATURE:
<223> OTHER INFORMATION: Amino acid sequence of a third fragment of the
      NS1 protein in the chimeric polyepitope of ZIKV

<400> SEQUENCE: 108

```
Ile Arg Phe Glu Glu Cys Pro Gly Thr Lys Val His Val Glu Glu Thr
1               5                   10                  15
```

<210> SEQ ID NO 109

-continued

```
<211> LENGTH: 48
<212> TYPE: DNA
<213> ORGANISM: Artificial sequence
<220> FEATURE:
<223> OTHER INFORMATION: Native nucleotide sequence of the
      polynucleotide encoding a third fragment of the NS1 protein in the
      chimeric polyepitope of ZIKV

<400> SEQUENCE: 109
attcggtttg aggaatgccc aggcactaag gtccacgtgg aggaaaca                      48

<210> SEQ ID NO 110
<211> LENGTH: 45
<212> TYPE: PRT
<213> ORGANISM: Artificial sequence
<220> FEATURE:
<223> OTHER INFORMATION: Amino acid sequence of a fragment of the NS3
      protein in the chimeric polyepitope of ZIKV

<400> SEQUENCE: 110

Ile Phe Lys Thr Lys Asp Gly Asp Ile Gly Ala Val Ala Leu Asp Tyr
 1               5                  10                  15

Pro Ala Gly Thr Ser Gly Ser Pro Ile Leu Asp Lys Cys Gly Arg Val
                20                  25                  30

Ile Gly Leu Tyr Gly Asn Gly Val Val Ile Lys Asn Gly
            35                  40                  45

<210> SEQ ID NO 111
<211> LENGTH: 135
<212> TYPE: DNA
<213> ORGANISM: Artificial sequence
<220> FEATURE:
<223> OTHER INFORMATION: Native nucleotide sequence of the
      polynucleotide encoding a fragment of the NS3 protein in the
      chimeric polyepitope of ZIKV

<400> SEQUENCE: 111
atatttaaga caaaggatgg ggacattgga gcggttgcgc tggattaccc agcaggaact         60
tcaggatctc caatcctaga caagtgtggg agagtgatag gactttatgg caatggggtc        120
gtgatcaaaa atggg                                                         135

<210> SEQ ID NO 112
<211> LENGTH: 142
<212> TYPE: PRT
<213> ORGANISM: Artificial sequence
<220> FEATURE:
<223> OTHER INFORMATION: Amino acid sequence of a second fragment of the
      NS3 protein in the chimeric polyepitope of ZIKV

<400> SEQUENCE: 112

Lys Thr Arg Arg Val Leu Pro Glu Ile Val Arg Glu Ala Ile Lys Thr
 1               5                  10                  15

Arg Leu Arg Thr Val Ile Leu Ala Pro Thr Arg Val Val Ala Ala Glu
                20                  25                  30

Met Glu Glu Ala Leu Arg Gly Leu Pro Val Arg Tyr Met Thr Thr Ala
            35                  40                  45

Val Asn Val Thr His Ser Gly Thr Glu Ile Val Asp Leu Met Cys His
         50                 55                  60

Ala Thr Phe Thr Ser Arg Leu Leu Gln Pro Ile Arg Val Pro Asn Tyr
 65              70                  75                  80

Asn Leu Tyr Ile Met Asp Glu Ala His Phe Thr Asp Pro Ser Ser Ile
                85                  90                  95
```

```
Ala Ala Arg Gly Tyr Ile Ser Thr Arg Val Glu Met Gly Glu Ala Ala
            100                 105                 110

Ala Ile Phe Met Thr Ala Thr Pro Pro Gly Thr Arg Asp Ala Phe Pro
        115                 120                 125

Asp Ser Asn Ser Pro Ile Met Asp Thr Glu Val Glu Val Pro
    130                 135                 140

<210> SEQ ID NO 113
<211> LENGTH: 426
<212> TYPE: DNA
<213> ORGANISM: Artificial sequence
<220> FEATURE:
<223> OTHER INFORMATION: Native nucleotide sequence of the
      polynucleotide encoding a second fragment of the NS3 protein in
      the chimeric polyepitope of ZIKV

<400> SEQUENCE: 113
aaaaccagga gagttcttcc tgaaatagtc cgtgaagcca taaaaacaag actccgtact      60
gtgatcttag ctccaaccag ggttgtcgct gctgaaatgg aggaagccct tagagggctt    120
ccagtgcgtt atatgacaac agcagtcaat gtcacccact ctggaacaga aatcgtcgac    180
ttaatgtgcc atgccacctt cacttcacgt ctactacagc caatcagagt ccccaactat    240
aatctgtata ttatggatga ggcccacttc acagatccct caagtatagc agcaagagga    300
tacatttcaa caagggttga gatgggcgag gcggctgcca tcttcatgac cgccacgcca    360
ccaggaaccc gtgacgcatt tccggactcc aactcaccaa ttatggacac cgaagtggaa    420
gtccca                                                                426

<210> SEQ ID NO 114
<211> LENGTH: 74
<212> TYPE: PRT
<213> ORGANISM: Artificial sequence
<220> FEATURE:
<223> OTHER INFORMATION: Amino acid sequence of a fragment of the NS4B
      protein in the chimeric polyepitope of ZIKV

<400> SEQUENCE: 114

Gln Ala Gly Val Leu Phe Gly Met Gly Lys Gly Met Pro Phe Tyr Ala
1               5                   10                  15

Trp Asp Phe Gly Val Pro Leu Leu Met Ile Gly Cys Tyr Ser Gln Leu
            20                  25                  30

Thr Pro Leu Thr Leu Ile Val Ala Ile Ile Leu Leu Val Ala His Tyr
        35                  40                  45

Met Tyr Leu Ile Pro Gly Leu Gln Ala Ala Ala Arg Ala Ala Gln
    50                  55                  60

Lys Arg Thr Ala Ala Gly Ile Met Lys Asn
65                  70

<210> SEQ ID NO 115
<211> LENGTH: 222
<212> TYPE: DNA
<213> ORGANISM: Artificial sequence
<220> FEATURE:
<223> OTHER INFORMATION: Native nucleotide sequence of the
      polynucleotide encoding a fragment of the NS4B protein in the
      chimeric polyepitope of ZIKV

<400> SEQUENCE: 115
caagctggag tgttgtttgg tatgggcaaa gggatgccat tctacgcatg ggactttgga      60
gtcccgctgc taatgatagg ttgctactca caattaacac ccctgaccct aatagtggcc    120
```

```
atcattttgc tcgtggcgca ctacatgtac ttgatcccag ggctgcaggc agcagctgcg      180
cgtgctgccc agaagagaac ggcagctggc atcatgaaga ac                        222
```

<210> SEQ ID NO 116
<211> LENGTH: 219
<212> TYPE: PRT
<213> ORGANISM: Artificial sequence
<220> FEATURE:
<223> OTHER INFORMATION: Amino acid sequence of a fragment of the NS5
      protein in the chimeric polyepitope of ZIKV

<400> SEQUENCE: 116

```
Ile Ile Gly Asn Arg Ile Glu Arg Ile Arg Ser Glu His Ala Glu Thr
1               5                   10                  15

Trp Phe Phe Asp Glu Asn His Pro Tyr Arg Thr Trp Ala Tyr His Gly
            20                  25                  30

Ser Tyr Glu Ala Pro Thr Gln Gly Ser Ala Ser Ser Leu Ile Asn Gly
        35                  40                  45

Val Val Arg Leu Leu Ser Lys Pro Trp Asp Val Val Thr Gly Val Thr
    50                  55                  60

Gly Ile Ala Met Thr Asp Thr Thr Pro Tyr Gly Gln Gln Arg Val Phe
65                  70                  75                  80

Lys Glu Lys Val Asp Thr Arg Val Pro Asp Pro Gln Glu Gly Thr Arg
                85                  90                  95

Gln Val Met Ser Met Val Ser Ser Trp Leu Trp Lys Glu Leu Gly Lys
            100                 105                 110

His Lys Arg Pro Arg Val Cys Thr Lys Glu Glu Phe Ile Asn Lys Val
        115                 120                 125

Arg Ser Asn Ala Ala Leu Gly Ala Ile Phe Glu Glu Glu Lys Glu Trp
    130                 135                 140

Lys Thr Ala Val Glu Ala Val Asn Asp Pro Arg Phe Trp Ala Leu Val
145                 150                 155                 160

Asp Lys Glu Arg Glu His His Leu Arg Gly Glu Cys Gln Ser Cys Val
                165                 170                 175

Tyr Asn Met Met Gly Lys Arg Glu Lys Lys Gln Gly Glu Phe Gly Lys
            180                 185                 190

Ala Lys Gly Ser Arg Ala Ile Trp Tyr Met Trp Leu Gly Ala Arg Phe
        195                 200                 205

Leu Glu Phe Glu Ala Leu Gly Phe Leu Asn Glu
    210                 215
```

<210> SEQ ID NO 117
<211> LENGTH: 657
<212> TYPE: DNA
<213> ORGANISM: Artificial sequence
<220> FEATURE:
<223> OTHER INFORMATION: Native nucleotide sequence of the
      polynucleotide encoding a fragment of the NS5 protein in the
      chimeric polyepitope of ZIKV

<400> SEQUENCE: 117

```
atcattggta accgcattga aaggatccgc agtgagcacg cggaaacgtg gttctttgac      60
gagaaccacc catataggac atgggcttac atggaagct atgaggcccc cacacaaggg     120
tcagcgtcct ctctaataaa cggggttgtc aggctcctgt caaaaccctg ggatgtggtg    180
actggagtca caggaatagc catgaccgac accacaccgt atggtcagca aagagttttc    240
aaggaaaaag tggacactag ggtgccagac ccccaagaag cactcgtca ggttatgagc     300
```

```
atggtctctt cctggttgtg aaagagcta ggcaaacaca acggccacg agtctgtacc    360 aaagaagagt tcatcaacaa ggttcgtagc aatgcagcat tagggggcaat atttgaagag    420 gaaaagagt ggaagactgc agtggaagct gtgaacgatc caaggttctg ggctctagtg     480
gacaaggaaa gagagcacca cctgagagga gagtgccaga gttgtgtgta caacatgatg    540
ggaaaaagag aaaagaaaca aggggaattt ggaaaggcca agggcagccg cgccatctgg    600
tatatgtggc taggggctag atttctagag ttcgaagccc ttggattctt gaacgag       657
```

```
<210> SEQ ID NO 118
<211> LENGTH: 55
<212> TYPE: PRT
<213> ORGANISM: Artificial sequence
<220> FEATURE:
<223> OTHER INFORMATION: Amino acid sequence of a second fragment of the
      NS5 protein in the chimeric polyepitope of ZIKV

<400> SEQUENCE: 118
```

Arg Phe Asp Leu Glu Asn Glu Ala Leu Ile Thr Asn Gln Met Glu Lys
1               5                   10                  15

Gly His Arg Ala Leu Ala Leu Ala Ile Ile Lys Tyr Thr Tyr Gln Asn
                20                  25                  30

Lys Val Val Lys Val Leu Arg Pro Ala Glu Lys Gly Lys Thr Val Met
        35                  40                  45

Asp Ile Ile Ser Arg Gln Asp
    50                  55

```
<210> SEQ ID NO 119
<211> LENGTH: 165
<212> TYPE: DNA
<213> ORGANISM: Artificial sequence
<220> FEATURE:
<223> OTHER INFORMATION: Native nucleotide sequence of the
      polynucleotide encoding a second fragment of the NS5 protein in
      the chimeric polyepitope of ZIKV

<400> SEQUENCE: 119
aggtttgatc tggagaatga agctctaatc accaaccaaa tggagaaagg gcacagggcc    60
ttggcattgg ccataatcaa gtacacatac caaaacaaag tggtaaaggt ccttagacca   120
gctgaaaaag ggaaaacagt tatggacatt atttcgagac aagac                   165
```

```
<210> SEQ ID NO 120
<211> LENGTH: 18
<212> TYPE: PRT
<213> ORGANISM: Artificial sequence
<220> FEATURE:
<223> OTHER INFORMATION: Amino acid sequence of a third fragment of the
      NS5 protein in the chimeric polyepitope of ZIKV

<400> SEQUENCE: 120
```

Met Glu Ala Glu Glu Val Leu Glu Met Gln Asp Leu Trp Leu Leu Arg
1               5                   10                  15

Arg Ser

```
<210> SEQ ID NO 121
<211> LENGTH: 54
<212> TYPE: DNA
<213> ORGANISM: Artificial sequence
<220> FEATURE:
<223> OTHER INFORMATION: Native nucleotide sequence of the
      polynucleotide encoding a third fragment of the NS5 protein in the
      chimeric polyepitope of ZIKV
```

<400> SEQUENCE: 121
atggaggctg aggaagttct agagatgcaa gacttgtggc tgctgcggag gtca            54

<210> SEQ ID NO 122
<211> LENGTH: 123
<212> TYPE: PRT
<213> ORGANISM: Artificial sequence
<220> FEATURE:
<223> OTHER INFORMATION: Amino acid sequence of a fourth fragment of the
    NS5 protein in the chimeric polyepitope of ZIKV

<400> SEQUENCE: 122

Lys Pro Ser Thr Gly Trp Asp Asn Trp Glu Glu Val Pro Phe Cys Ser
1               5                   10                  15

His His Phe Asn Lys Leu His Leu Lys Asp Gly Arg Ser Ile Val Val
            20                  25                  30

Pro Cys Arg His Gln Asp Glu Leu Ile Gly Arg Ala Arg Val Ser Pro
        35                  40                  45

Gly Ala Gly Trp Ser Ile Arg Glu Thr Ala Cys Leu Ala Lys Ser Tyr
    50                  55                  60

Ala Gln Met Trp Gln Leu Leu Tyr Phe His Arg Arg Asp Leu Arg Leu
65                  70                  75                  80

Met Ala Asn Ala Ile Cys Ser Ser Val Pro Val Asp Trp Val Pro Thr
                85                  90                  95

Gly Arg Thr Thr Trp Ser Ile His Gly Lys Gly Glu Trp Met Thr Thr
            100                 105                 110

Glu Asp Met Leu Val Val Trp Asn Arg Val Trp
        115                 120

<210> SEQ ID NO 123
<211> LENGTH: 369
<212> TYPE: DNA
<213> ORGANISM: Artificial sequence
<220> FEATURE:
<223> OTHER INFORMATION: Native nucleotide sequence of the
    polynucleotide encoding a fourth fragment of the NS5 protein in
    the chimeric polyepitope of ZIKV

<400> SEQUENCE: 123
aaaccctcaa ctggatggga caactgggaa gaagttccgt tttgctccca ccacttcaac      60
aagctccatc tcaaggacgg gaggtccatt gtggttccct gccgccacca agatgaactg     120
attggccggg cccgcgtctc tccaggggcg ggatggagca tccgggagac tgcttgccta     180
gcaaaatcat atgcgcaaat gtggcagctc ctttatttcc acagaaggga cctccgactg     240
atggccaatg ccatttgttc atctgtgcca gttgactggg ttccaactgg agaactacc      300 tggtcaatcc atgaaaggg agaatggatg accactgaag acatgcttgt ggtgtggaac     360
agagtgtgg                                                            369

<210> SEQ ID NO 124
<211> LENGTH: 2886
<212> TYPE: DNA
<213> ORGANISM: Artificial sequence
<220> FEATURE:
<223> OTHER INFORMATION: Nucleotide sequence of the polynucleotide
    encoding a chimeric epitope of ZIKV

<400> SEQUENCE: 124
ggcggcttcc ggatcgtgaa tatgctgaag agaggcgtgg ccagagtcag ccctttttggc    60 ggactgaaaa gactgcctgc cggactgctt ctcggccacg gacctattag aatggtgctg    120

```
gccatcctgg cctttctgcg gtttacagcc atcaagccta gcctgggcct gatcaataga   180
tggggcagcg tgggcaagaa agaagccatg gaaatcatca agaagttcaa gaaagacctg   240
gccgccatgc tgcggatcat caacgcccgg aaagaaaagg tgttcgtgta caacgacgtc   300
gaggcctggc gggacagata caagtatcac cctgacagcc ctagaaggct ggccgctgct   360
gtgaaacagg cctgggagga tggcatctgt ggcatcagca gcgtgtcccg gatggaaaac   420
atcatgtggc ggagcgtgga aggcgagctg aacgccattc tggaagaaaa cggcgtgcag   480
ctgacagtgg tcgtgggctc cgtgaagaat cctatgtggc gaggacctca gagactgccc   540
gtgcctgtga atgaactgcc tcatggatgg aaggcctggg gcaagagcta ttttgtgcgg   600
gctgccaaga ccaacaacca cagagcctgg aacagcttcc tggtggaaga tcacggcttc   660
ggcgtgttcc acaccagcgt gtggctgaaa gtgcgcgagg attacagcct ggaatgcgat   720
cctgccgtga tcggaacagc cgtgaaggga aagaagccg tgcacagcga tctcggctac   780
tggatcgaga gcgagaagaa cgacacctgg atcagattcg aggaatgccc cggcaccaag   840
gtgcacgtgg aagagacaat cttcaagacc aaggacggcg acatcggcgc cgtggctctt   900
gattatcctg ccggaacaag cggcagcccc atcctggata gtgtggcag agtgatcggc   960 ctgtacggca acggcgttgt gatcaagaac ggcaagacca aagagtgct gcccgagatc   1020 gtgcgggaag ccattaagac ccggctgaga acagtgattc tggcccctac aagagtggtg   1080
gccgccgaaa tggaagaagc cctgagaggc ctgcctgtgc ggtacatgac aaccgccgtg   1140
aatgtgacac acagcggcac agagatcgtg gacctgatgt gtcacgccac cttcacctct   1200
agactgctgc agcccatcag agtgcccaac tacaacctgt acatcatgga cgaggcccac   1260
ttcacagacc ccagctctat tgccgccaga ggctacatca gcaccagagt ggaaatgggc   1320
gaagccgccg ctatcttcat gacagccaca cctccaggca ccagggacgc ctttccagac   1380
agcaacagcc ctatcatgga caccgaggtg gaagtgcctc aggctggcgt tctgtttggc   1440
atgggcaagg gcatgccttt ctacgcctgg gattttggcg tgcccctgct gatgatcggc   1500
tgctactctc agctgacccc tctgacactg atcgtggcca ttattctgct ggtgccccac   1560
tacatgtatc tgatccctgg actgcaggcc gctgcagcca gagctgctca aaaaagaaca   1620
gccgccggaa tcatgaagaa catcatcggc aaccggatcg agcggatcag aagcgagcac   1680
gccgagacat ggttcttcga cgagaatcac ccctaccgga catgggccta ccacggatct   1740
tatgaagccc ctacacaggg cagcgccagc agccttatca atggcgttgt gcggctgctg   1800
agcaagccct gggatgttgt tacaggcgtg accggaatcg ccatgaccga tacaacaccc   1860
tacggccagc agcgggtgtt caaagaaaaa gtggacacca gggtgcccga tcctcaagag   1920
ggcacaagac aagtgatgag catggtgtcc agctggctgt ggaaagagct gggcaagcac   1980
aagaggccca gagtgtgcac caaagaggaa ttcatcaaca agtgcggag caacgccgct   2040 ctgggcgcca tctttgagga agagaaagaa tggaaaactg ccgttgaggc cgtgaacgac   2100
cctagatttt gggccctcgt ggacaaagag agagagcacc atctgagagg cgagtgccag   2160
tcctgcgtgt acaatatgat gggcaaacgc gagaaaaagc agggcgagtt cggcaaggcc   2220
aagggaagca gagccatctg gtatatgtgg ctggagccag attcctgga attcgaggcc   2280 ctgggcttcc tgaacgagag attcgacctg gaaaatgagg ccctgatcac caaccagatg   2340
gaaaagggac acagagccct ggctctggcc atcatcaagt acaccttacca gaacaaggtg   2400 gtcaaggtgc tgaggccagc cgagaagggc aagactgtga tggacatcat cagccggcag   2460
```

-continued

```
gacatggaag ccgaagaggt gctggaaatg caggatctgt ggctgctgcg gagaagcaag    2520
ccttccacag gctgggacaa ctgggaagaa gtgcccttct gcagccacca cttcaacaag    2580
ctgcacctga aggacggcag atccatcgtg gtgccttgca gacaccagga cgaactgatc    2640
ggcagagcta gagtttctcc tggcgccgga tggtccatca gagaaacagc ctgtctggcc    2700
aagagctacg cccagatgtg gcagctgctg tacttccaca gacgggacct gagactgatg    2760
gccaatgcca tctgtagcag cgtgccagtg gattgggtgc caaccggcag aaccacatgg    2820
tctatccacg gcaaaggcga gtggatgacc accgaggata tgctggtcgt gtggaataga    2880
gtttgg                                                                2886
```

ZIKA VIRUS CHIMERIC POLYEPITOPE COMPRISING NON-STRUCTURAL PROTEINS AND ITS USE IN AN IMMUNOGENIC COMPOSITION

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Mar. 14, 2022, is named B12633A_ST25.txt and is 62,876 bytes in size.

CROSS REFERENCE TO RELATED APPLICATIONS

This application is a continuation of U.S. application Ser. No. 16/762,849, filed May 8, 2020, which is the U.S. Natl. Stage of International Appln. PCT/EP2018/080677, filed Nov. 8, 2018, which claims the benefit of EP application 17306553.3 filed Nov. 7, 2017, all of which are herein incorporated by reference in their entirety.

FIELD OF THE INVENTION

The present invention is directed to a Zika virus (ZIKV) chimeric polyepitope comprising non-structural proteins and its use in an immunogenic composition. The present invention provides means, in particular polynucleotides, vectors and cells expressing said chimeric polyepitope. The present invention also relates to a composition or a vaccine comprising at least one of said polyepitope, polynucleotide, vector or host cell for use in the prevention of a ZIKV infection in a human subject, or for use in the prevention of ZIKV and dengue virus (DENV) infections in a human subject.

Zika virus (ZIKV) is a flavivirus transmitted by *Aedes* species mosquitoes. It is a single positive-stranded RNA virus closely related to yellow fever virus, dengue virus (DENV) and West Nile virus (Kuno G et al., 1998, *J Virol.* 72(1):73-83). Initially isolated in the Zika forest in Uganda in 1947 (Dick G W et al., 1952, *Transactions of the Royal Society of Tropical Medicine and Hygiene* 46(5):509-520), it caused an explosive outbreak for the first time in Yap Island, Federated States of Micronesia (Duffy M R, et al. 2009, *The New England journal of medicine* 360(24):2536-2543). Subsequent outbreaks with higher number of cases occurred in 2013-2014 in French Polynesia and other South Pacific Islands and more recently in the Americas (Cao-Lormeau V M, et al. 2014, *Emerging infectious diseases* 20(6):1085-1086; Campos G S, et al. 2015, *Emerging infectious diseases* 21(10):1885-1886; Dupont-Rouzeyrol M, et al. 2015, *Emerging infectious diseases* 21(2):381-382; Zanluca C, et al. 2015, *Mem Inst Oswaldo Cruz* 110(4):569-572; Pacheco O, et al. 2016, *Zika Virus Disease in Colombia—Preliminary Report. The New England journal of medicine*). Although initially believed to only cause mild, self-limiting disease, a causal relationship between ZIKV and neurological complications, such as Guillain-Barré syndrome or congenital malformations was established only recently, with the 2013 and 2015 outbreaks in French Polynesia and Brazil (Oehler E, et al. 2014 *Euro Surveill* 19(9); Cao-Lormeau V M, et al. 2016, *Lancet* 387(10027):1531-1539; Cauchemez S, et al. 2016, *Lancet* 387 (10033): 2125-2132; Soares de Araujo J S, et al. 2016, *Bull World Health Organ* 94(11):835-840).

In addition to an enhanced infectivity of the Asian lineage of ZIKV due to a spontaneous mutation in NS1 (Liu Y, et al. 2017, *Nature* 545 (7655): 482-486), which could explain its recent re-emergence in the Americas (Enfissi A et al., *Lancet* 387(10015):227-228), one of the most important concerns today is related to the high level of DENV seroprevalence in areas where ZIKV is circulating (Katzelnick L C, et al., *The Lancet. Infectious diseases* 17(3):e88-e100). Indeed, recent studies have shown that anti-DENV pre-existing antibodies may enhance ZIKV infection and increase disease severity (Dejnirattisai W, et al. 2016 *Nat Immunol* 17(9):1102-1108; Stettler K, et al. 2016 *Science* 353(6301):823-826; Paul L M, et al. 2016 *Dengue Virus Antibodies Enhance Zika Virus Infection. BioRxiv*; Priyamvada L, et al. 2016, *Proc Natl Acad Sci USA* 113(28):7852-7857; Bardina S V, et al. 2017, *Science* 356(6334):175-180). Given these constraints, and the lack of appropriate treatment for ZIKV infection, there is an urgent need to develop a vaccine against this infectious disease.

While antibodies against the E protein of DENV or ZIKV were shown to be highly cross-reactive, T cells can be cross-reactive or not, depending on the targeted peptides. A low degree of CD4 T-cell cross-reactivity between DENV and ZIKV was indeed observed in human donors immune to one of these viruses (Stettler K, et al. 2016, *Science* 353 (6301):823-826), whereas DENV/ZIKV cross-reactive and protective CD8 T cells were identified in DENV-immune mice after challenge with ZIKV (Wen J, et al. 2017, *Nat Microbiol* 2:17036). Considering the sequence identity between DENV and ZIKV for the capsid and envelop structural proteins, and the non-structural proteins NS3 and NS5, that represent the main targets of DENV-specific CD4 and CD8 T cells, respectively, and the protective role of DENV-specific T cells (Weiskopf D et al., *Proc Natl Acad Sci USA* 2013, 110(22):E2046-2053; Weiskopf D et al., *Proc Natl Acad Sci USA* 2015, 112(31):E4256-4263, Rivino L & Lim M Q, 2016, *Immunology* 150(2):146-154), efforts are thus currently directed towards the mapping of T-cell epitopes to design new and more effective vaccines against ZIKV. Predictions of T-cell antigens were conducted by modelling potential epitopes that could bind to different HLA class I or class II alleles, from the ZIKV proteome and by analyzing ex vivo T-cell responses in transgenic mice expressing human HLA-B*0702 and HLA-A*0101 molecules (Wen J, et al. 2017, *Nat Microbiol* 2:17036, 23-25). Strikingly, DENV/ZIKV cross-reactive T cells were identified in these DENV-immune mice, which could mediate protection against ZIKV infection (Wen J, et al. 2017, *Nat Microbiol* 2:17036, 23-25). This result is in agreement with concomitant studies demonstrating a protective role for CD8+ T cells in immune protection against ZIKV in mice (Elong Ngono A, et al. 2017, *Cell host & microbe* 21(1): 35-46). However, while these studies have demonstrated a protective role for CD8+ T cells against ZIKV infection in mice, and while several peptides derived from ZIKV have been identified in DENV-naïve and DENV-pre-exposed donors (Grifoni A, et al. 2017, *J. Virol. DOI:* 10.1128/ JVI.01469-17, posted online on 4 Oct. 2017), the precise identification of the human T-cell epitopes that are unique to ZIKV or shared with DENV is still incomplete. In the present study, the inventors identified these epitopes from blood donors with a history of only ZIKV infection or both DENV and ZIKV infections.

Using PBMCs from Colombian blood donors with previous ZIKV infection, the inventors established the first map of the distribution of ZIKV T-cell epitopes, by quantifying ex vivo IFNγ responses against peptides covering the whole ZIKV proteomic sequence by enzyme-linked immunosorbent spot (ELISPOT) assay. Measurement of the magnitude of T-cell responses (mediated by CD4 and/or CD8 T cells) against these peptides allowed the identification of immunodominant epitopes that induced strong responses in donors carrying specific HLA alleles. More specifically, the inventors showed that the structural proteins C and E and the non-structural (NS) proteins NS1, NS3, NS4B and NS5, in particular the non-structural proteins NS1, NS3 and NS5, contained most of the immunodominant epitopes that induced a strong T-cell response. In donors with a history of DENV infection, the strongest T-cell responses were directed against peptides with a high level of amino acid identity with the four serotypes of DENV, and some matched previously described DENV CD8+ T-cell epitopes, suggesting the activation of cross-reactive T cells. The results of the inventors provided new insights into T-cell responses to ZIKV and identified for the first time in immune individuals, T-cell epitopes that could be used for future ZIKV and DENV vaccine candidates.

The invention thus relates to a chimeric polyepitope comprising (i) at least the following T-cell epitopes of (a) and (b), or (ii) at least the following T-cell epitopes of (a) and (c), or (iii) at least the following T-cell epitopes of (b) and (c):
(a) a T-cell epitope of the non-structural (NS) NS1 protein of a Zika virus (ZIKV) comprising or consisting of an amino acid sequence selected from the group consisting of SEQ ID NOs: 10-12, 14, 15, 17-19, 23, 24 and 78-83,
(b) a T-cell epitope of the NS3 protein of a ZIKV comprising or consisting of an amino acid sequence selected from the group consisting of SEQ ID NOs: 28, 29, 31, 33-35, 84 and 85,
(c) a T-cell epitope of the NS5 protein of a ZIKV comprising or consisting of an amino acid sequence selected from the group consisting of SEQ ID NOs: 46, 48-50, 52-55, 57-60, 62, 64, 67, 69, 72, 73 and 86-91,
or a T-cell epitope variant thereof, which differs from the original amino acid sequence of the T-cell epitope of (a), (b) or (c) by point mutation of one or more amino acid residues and which has at least 90% sequence identity or more than 95% sequence identity or 99% sequence identity with said original sequence.

In a particular embodiment of the invention, the chimeric polyepitope comprises (i) at least the following T-cell epitopes of (a) and (b), or (ii) at least the following T-cell epitopes of (a) and (c), or (iii) at least the following T-cell epitopes of (b) and (c):
(a) a T-cell epitope of the NS1 protein of a ZIKV comprising or consisting of an amino acid sequence selected from the group consisting of SEQ ID NOs: 10-12, 14, 15, 17-19, 23, 24 and 78-83,
(b) a T-cell epitope of the NS3 protein of a ZIKV comprising or consisting of an amino acid sequence selected from the group consisting of SEQ ID NOs: 28, 31, 33-35, 84 and 85,
(c) a T-cell epitope of the NS5 protein of a ZIKV comprising or consisting of an amino acid sequence selected from the group consisting of SEQ ID NOs: 46, 52-55, 57, 59, 60, 62, 64, 67, 69, 72, 73 and 86, 87, 89-91,
or a T-cell epitope variant thereof, which differs from the original amino acid sequence of the T-cell epitope of (a), (b) or (c) by point mutation of one or more amino acid residues and which has at least 90% sequence identity or more than 95% sequence identity or 99% sequence identity with said original sequence.

As defined herein, the term "polyepitope" refers to a chimeric or recombinant molecule, in particular a chimeric or recombinant polypeptide with at least 2, in particular at least 3, preferably at least 5, and more preferably 10 or more than 10, or 15 or more than 15 T-cell epitopes identified in ZIKV proteins with the exception of full-length or native ZIKV proteins, in particular in the non-structural proteins NS1, NS3 or NS5 of ZIKV with the exception of full-length or native NS1, NS3 or NS5 proteins of ZIKV.

As defined herein, an "epitope" is a peptide or polypeptide which is an antigenic determinant, i.e. the peptide site recognized by cells of the immune system (immune cells) and especially the site necessary to elicit an immune response. The term epitope encompasses both linear epitope for which the consecutive amino acids (from 9 to 15, in particular, 8, 9, 10 or 15, more preferably 9 or 15) are recognized by immune cells and, conformational epitope for which immune cells recognize amino acids to the extent they adopt a proper configuration or conformation. Consequently, in some epitopes, the conformation (three dimensional structure) is as important as the amino acid sequence (primary structure).

As defined herein, a "T-cell epitope" is any peptide or polypeptide involved in the induction of a T cell immune response against a ZIKV, or a ZIKV and a DENV, in particular against anyone of DENV1, DENV2, DENV3, DENV4 or against multiple, in particular all DENV serotypes. In particular, said T-cell epitopes are recognized in association with class I MHC (Major Histocompatibility Complex) molecules, such as epitopes which target cells are CD8+T lymphocytes or T epitopes recognized in association with class II MHC molecules, such as those which target cells are CD4+T lymphocytes.

As defined herein, the term "variant thereof" refers to a T-cell epitope which differs from the original amino acid sequence of the T-cell epitope of (a), (b) or (c) by point mutation of one or more amino acid residues, in particular by 1, 2, 3, 4, 5, 6, 7, 8, 9 or 10 amino acid residues, and which has at least 90% sequence identity or more than 95% sequence identity or 99% sequence identity with said original sequence. The mutation(s) defining the variant of the T-cell epitope can be deletion(s), including especially point deletion(s) of 1, 2, 3, 4, 5, 6, 7, 8, 9, 10 or more amino acid residue(s) or can be substitution(s), especially conservative substitution(s) of 1, 2, 3, 4, 5, 6, 7, 8, 9, 10 or more amino acid residue(s). Said variant of the T-cell epitope can have an amino acid sequence which has the same length as the original amino acid sequence of the T-cell epitope of (a), (b) or (c).

As defined herein, the term "chimeric polyepitope" means any polyepitopic polypeptide comprising sub-portions or fragments of different ZIKV proteins, in particular different ZIKV NS proteins, preferably different ZIKV NS proteins selected among NS1, NS3 and NS5 proteins. Said chimeric polyepitope does not comprise full-length or native ZIKV proteins, in particular does not comprise full-length or native ZIKV NS proteins, preferably does not comprise full-length or native ZIKV NS proteins selected among NS1, NS3 and NS5 proteins.

In a particular embodiment of the invention, the chimeric polyepitope comprises less than 30 ZIKV T-cell epitopes, in particular less than 25 ZIKV T-cell epitopes, preferably less than 20 ZIKV T-cell epitopes.

In a particular embodiment of the invention, the amino acid sequences of the T-cell epitopes of a ZIKV protein taken as a whole are different from the amino acid sequences of any other epitopes of another ZIKV protein, in particular any other ZIKV T-cell epitopes of another ZIKV protein.

In another particular embodiment of the invention, the amino acid sequences of the ZIKV T-cell epitopes may differ by one or more amino acids from the amino acid sequences of other epitopes, in particular other ZIKV T-cell epitopes, and/or may have overlapping sequences, and accordingly share some amino acids.

The chimeric polyepitope of the invention comprises at least T-cell epitopes of the NS1 and NS3 proteins of a ZIKV, or at least T-cell epitopes of the NS1 and NS5 proteins of a ZIKV, or at least T-cell epitopes of the NS3 and NS5 proteins of a ZIKV, with the exception of full-length or native ZIKV proteins. Preferably, the chimeric polyepitope of the invention consists of T-cell epitopes of the NS1 and NS3 proteins of a ZIKV, or T-cell epitopes of the NS1 and NS5 proteins of a ZIKV, or T-cell epitopes of the NS3 and NS5 proteins of a ZIKV, with the exception of full-length or native ZIKV proteins.

In a preferred embodiment of the invention, the chimeric polyepitope comprises at least T-cell epitopes of the NS1, NS3 and NS5 proteins of a ZIKV, with the exception of full-length or native ZIKV proteins.

In another preferred embodiment of the invention, the chimeric polyepitope consists of T-cell epitopes of the NS1, NS3 and NS5 proteins of a ZIKV, with the exception of full-length or native ZIKV proteins.

In a particular embodiment of the invention, the chimeric polyepitope comprises sub-portions or fragments of different polyepitopes from the same ZIKV protein, in particular a NS protein of a ZIKV, preferably a NS1, NS3 or NS5 protein of a ZIKV, or even from the same polyepitopes from different ZIKV proteins, in particular NS proteins of a ZIKV, preferably NS1, NS3 and NS5 proteins of a ZIKV. The polyepitope of the invention includes the polyepitope variant. Accordingly each definition or embodiment disclosed herein applies to the variant polyepitope unless it is technically irrelevant.

As defined herein, the term "fragment" refers to a part or a portion of a ZIKV protein, preferably of a NS protein (i.e. NS1, NS3 or NS5 protein) of a ZIKV, which is shorter in length than the protein, preferably the NS protein (i.e. NS1, NS3 or NS5 protein), from which it originates. Each fragment can comprise a plurality of epitopes suitable for elicitation of an immune response, especially an immune T-cell response against a ZIKV infection or against ZIKV and DENV infections. Each fragment corresponds to a sequence of consecutive amino acids.

In a preferred embodiment of the invention, the chimeric polyepitope comprises at least the T-cell epitopes of (a), (b) and (c) as defined above, or the T-cell epitope variant thereof.

In another preferred embodiment of the invention, the chimeric polyepitope consists of (i) the T-cell epitopes of (a) and (b) as defined above, or (ii) the T-cell epitopes of (a) and (c) as defined above, or (iii) the T-cell epitopes of (b) and (c) as defined above, or (iv) the T-cell epitopes of (a), (b) and (c) as defined above, or the T-cell epitope variant thereof.

In another preferred embodiment of the invention, the T-cell epitope of (a) comprises or consists of the amino acid sequence selected from the group consisting of SEQ ID NOs: 17, 23 and 78-83, the T-cell epitope of (b) comprises or consists of the amino acid sequence selected from the group consisting of SEQ ID NOs: 31, 33, 84 and 85, and the T-cell epitope of (c) comprises or consists of the amino acid sequence selected from the group consisting of SEQ ID NOs: 46, 48, 52, 57, 62, 64, 67 and 86-91, preferably of SEQ ID NOs: 46, 52, 57, 62, 64, 67, 86, 87 and 89-91. Each of said T-cell epitope sequences contains 15 amino acid residues, i.e. is a 15-mer epitope that induces individually and/or collectively a T cell immune response. Each of these 15-mer epitopes includes individually and/or collectively at least a 9-mer epitope that also induces a T cell immune response. For example, the sequence of the 15-mer epitope in the NS1 protein of ZIKV (NS1$_{163-177}$) of SEQ ID NO: 17 (FHTSVWLKVREDYSL) includes the sequence of the 9-mer epitope of SEQ ID NO: 18 (VWLKVREDY) and the sequence of the 9-mer epitope of SEQ ID NO: 19 (WLKVREDYS). This suggests that the above-mentioned 15-mer epitopes comprise at least a 9-mer epitope but can also comprise other epitopes of 9-mer or more.

In another preferred embodiment of the invention, the T-cell epitope of (a) comprises or consists of the amino acid sequence of SEQ ID NOs: 11, 12, 17-19, 23, 24, 78, 80 and 83, the T-cell epitope of (b) comprises or consists of the amino acid sequence of SEQ ID NOs: 28, 31, 33, 34, 84 and 85, and the T-cell epitope of (c) comprises or consists of the amino acid sequence of SEQ ID NOs: 48-50, 52-55, 57, 58, 60, 62, 67, 88, 89 and 90, preferably of SEQ ID NOs: 52-55, 57, 60, 62, 67, 89 and 90.

In another particular embodiment of the invention, the chimeric polyepitope further comprises at least one T-cell epitope of a ZIKV protein selected from the group consisting of:

(i) a T-cell epitope of the capsid (C) protein of a ZIKV comprising or consisting of an amino acid sequence selected from the group consisting of SEQ ID NOs: 1, 2, 4-6 and 75, (ii) a T-cell epitope of the E protein of a ZIKV comprising or consisting of an amino acid sequence selected from the group consisting of SEQ ID NOs: 7, 76 and 77, (iii) a T-cell epitope of the NS2B protein of a ZIKV comprising or consisting of the amino acid sequence of SEQ ID NO: 25, (iv) a T-cell epitope of the NS4A protein of a ZIKV comprising or consisting of the amino acid sequence of SEQ ID NO: 36, and (v) a T-cell epitope of the NS4B protein of a ZIKV comprising or consisting of the amino acid sequence selected from the group consisting of SEQ ID NOs: 40-43.

In a preferred embodiment of the invention, the chimeric polyepitope comprises T-cell epitopes of at least 2, preferably at least 3 or 4, more preferably at least 5, 6, 7, 8, 9, 10 or 11 different ZIKV proteins.

In another preferred embodiment of the invention, the chimeric polyepitope further comprises a T-cell epitope of the C protein of a ZIKV comprising or consisting of an amino acid sequence selected from the group consisting of SEQ ID NOs: 1, 2, 4-6 and 75, and a T-cell epitope of the NS4B protein of a ZIKV comprising or consisting of the amino acid sequence selected from the group consisting of SEQ ID NOs: 40-43.

Thus, the chimeric polyepitope comprises at least T-cell epitopes of the C, NS1, NS3, NS4B and NS5 proteins of a ZIKV, with the exception of said full-length or native ZIKV proteins. In particular, the chimeric polyepitope comprises at least the following T-cell epitopes:

(i) a T-cell epitope of the C protein of a ZIKV comprising or consisting of an amino acid sequence selected from the group consisting of SEQ ID NOs: 1, 2, 4-6 and 75, preferably of SEQ ID NOs: 1, 4 and 75, (ii) a T-cell epitope of the NS1 protein of a ZIKV comprising or consisting of an amino acid sequence selected from the group consisting of SEQ ID NOs: 10-12, 14, 15, 17-19, 23, 24 and 78-83, preferably of SEQ ID NOs: 17, 23 and 78-83, (iii) a T-cell epitope of the NS3 protein of a ZIKV comprising or consisting of an amino acid sequence selected from the group consisting of SEQ ID NOs: 28, 29, 31, 33-35, 84 and 85, preferably of SEQ ID NOs: 28, 31, 33-35, 84 and 85, more preferably of SEQ ID NOs: 31, 33, 84 and 85, (iv) a T-cell epitope of the NS4B protein of a ZIKV comprising or consisting of an amino acid sequence selected from the group consisting of SEQ ID NOs: 40-43, (v) a T-cell epitope of the NS5 protein of a ZIKV comprising or consisting of an amino acid sequence selected from the group consisting of SEQ ID NOs: 46, 48-50, 52-55, 57-60, 62, 64, 67, 69, 72, 73 and 86-91, preferably of SEQ ID NOs: 46, 52-55, 57, 59, 60, 62, 64, 67, 69, 72, 73 and 86, 87 and 89-91, or comprising or consisting of an amino acid sequence selected from the group consisting of SEQ ID NOs: 46, 48, 52, 57, 62, 64, 67 and 86-91, preferably of SEQ ID NOs: 46, 52, 57, 62, 64, 67, 86, 87 and 89-91, or a T-cell epitope variant thereof, which differs from the original amino acid sequence of the T-cell epitope of (i), (ii), (iii), (iv) or (v) by point mutation of one or more amino acid residues and which has at least 90% sequence identity or more than 95% sequence identity or 99% sequence identity with said original sequence.

In another preferred embodiment of the invention, in the above-mentioned chimeric polyepitope:

(i) the T-cell epitope of the C protein of a ZIKV comprises or consists of the amino acid sequence of SEQ ID NOs: 4, 5, 6 and 75, (ii) the T-cell epitope of the NS1 protein of a ZIKV comprises or consists of the amino acid sequence of SEQ ID NOs: 11, 12, 17-19, 23, 24, 78, 80 and 83, (iii) the T-cell epitope of the NS3 protein of a ZIKV comprises or consists of the amino acid sequence of SEQ ID NOs: 28, 31, 33, 34, 84 and 85, (iv) the T-cell epitope of the NS4B protein of a ZIKV comprises or consists of the amino acid sequence of SEQ ID NOs: 40 and 41, and (v) the T-cell epitope of the NS5 protein of a ZIKV comprises or consists of the amino acid sequence of SEQ ID NOs: 48-50, 52-55, 57, 58, 60, 62, 67, 88, 89 and 90, preferably of SEQ ID NOs: 52-55, 57, 60, 62, 67, 89 and 90.

In another preferred embodiment of the invention, the chimeric polyepitope consists of T-cell epitopes of the C, NS1, NS3, NS4B and NS5 proteins of a ZIKV, with the exception of full-length or native ZIKV proteins.

All the definitions directed to the NS1, NS3 and NS5 proteins of a ZIKV mentioned above also apply to other proteins of a ZIKV, in particular to the C, E, NS1, NS2B, NS3, NS4A, NS4B and NS5 proteins of a ZIKV.

In a preferred embodiment of the invention, the chimeric polyepitope is (i) for use in the prevention of a ZIKV infection in a human subject or (ii) for use in the prevention of ZIKV and Dengue virus (DENV) infections in a human subject.

As defined herein, the term "prevention" refers to primary, secondary and tertiary preventions. Prevention of a ZIKV infection or ZIKV and DENV infections means that said infection(s) and associated risk factors are minimized, i.e. are obstructed or delayed. In particular, said infection(s) may be prevented before it occurs or identified at an early stage so that the symptoms of said infection(s) may be reduced.

In a more preferred embodiment of the invention, when the polyepitope is used in the prevention of a ZIKV infection in a human subject, the T-cell epitopes are ZIKV-specific epitopes comprising or consisting of an amino acid sequence selected from the group consisting of SEQ ID NOs: 1, 2, 5, 10, 11, 19, 27, 31, 40-43, 46, 72, 73, 75, 78-80, 82, 84, 85, 87 and 91.

In another more preferred embodiment of the invention, when the polyepitope is used in the prevention of ZIKV and DENV infections in a human subject, the T-cell epitopes are ZIKV-DENV cross-reactive epitopes comprising or consisting of an amino acid sequence selected from the group consisting of SEQ ID NOs: 1, 5, 6, 12, 14, 15, 17-19, 23, 24, 27, 28, 33-35, 40, 41, 46, 48-50, 52-55, 57, 59, 60, 62, 64, 67, 69, 72, 73, 84, 85 and 86-91, preferably of SEQ ID NOs: 1, 5, 6, 12, 14, 15, 17-19, 23, 24, 27, 28, 33-35, 40, 41, 46, 52-55, 57, 59, 60, 62, 64, 67, 69, 72, 73, 84, 85, 86, 87 and 89-91.

To be noted that T-cell epitopes comprising or consisting of an amino acid sequence selected from the group consisting of SEQ ID NOs: 1, 5, 19, 27, 40, 41, 46, 72, 73, 84, 85, 87 and 91 are both capable of inducing a T cell immune response in ZIKV donors and in DENV/ZIKV donors.

A non-exhaustive list of ZIKV T-cell epitopes, in particular ZIKV-specific T-cell epitopes and/or ZIKV-DENV cross-reactive T-cell epitopes, is provided in Tables 2 and 3 below. Said ZIKV T-cell epitopes comprise amino acid sequences defined as SEQ ID NOs: 1-91.

In a particular embodiment of the invention, the chimeric polyepitope comprises human leukocyte antigen (HLA)-restricted epitopes. The expression "HLA-restricted" refers to the capacity for a particular epitope to have an affinity for this type of HLA molecule. The HLA molecules used in the invention encompass either class I molecules (designated HLA-A, B or C) or class II molecules (designated DRB).

In another particular embodiment of the invention, the chimeric polyepitope elicits a human leukocyte antigen (HLA)-restricted CD8$^+$ and/or CD4$^+$ T cell response (i) against ZIKV, or (ii) against ZIKV and DENV, in particular DENV serotype 1 (DENV1), DENV serotype 2 (DENV2), DENV serotype 3 (DENV3) and DENV serotype 4 (DENV4), preferably against DENV serotype 1 (DENV1).

Complete nucleotide sequences of the reference genomes of the 4 dengue virus serotypes can be accessed from the Genbank database under accession numbers NC_001477.1, NC_001474.2, NC_001475.2 and NC_002640.1 respectively.

In a particular embodiment of the invention, said DENV is from the following strains: GenBank KDH0026A (DENV1), GenBank R0712259 (DENV2), GenBank KDH0010A (DENV3) and GenBank CRBIP10.4VIMFH4 (DENV4).

In a particular embodiment of the invention, the polyepitope elicits antigenic responses with HLA restriction such as HLA-A*0201, HLA-A*2402, HLA-B*0702, HLA-B*3501, HLA-B*4002, preferably HLA-A*0201, HLA-A*2402, HLA-B*0702 and HLA-B*3501.

In a particular embodiment of the invention, (i) at least T-cell epitopes of the NS1 and NS3 proteins of a ZIKV, or (ii) at least T-cell epitopes of the NS1 and NS5 proteins of a ZIKV, or (iii) at least T-cell epitopes of the NS3 and NS5 proteins of a ZIKV, or (iv) at least T-cell epitopes of the NS1, NS3 and NS5 proteins of a ZIKV, or (v) at least T-cell epitopes of the C, NS1, NS3, NS4B and NS5 proteins of a ZIKV, with the exception of full-length or native ZIKV proteins, are assembled in a unique polypeptide, preferably in a fusion polypeptide. Preferably, the above-defined T-cell epitopes are assembled in a fusion polypeptide.

Said T-cell epitopes can be directly or indirectly fused to each other.

According to a particular embodiment of the invention, one T-cell epitope is fused "directly" with another T-cell epitope, i.e. the 3' end of the T-cell epitope is directly linked to the 5' end of the second T-cell epitope (and so on), corresponding to a chimeric polyepitope composed of consecutive T-cell epitopes from at least two different ZIKV proteins, in particular the ZIKV C protein and the ZIKV NS proteins chosen among NS1, NS3, NS4B and NS5, in particular originating from a consensus sequence of ZIKV. According to an alternative embodiment, the fusion of the at least two T-cell epitopes, in particular the at least three T-cell epitopes, is "indirect" and accordingly involves the presence of other, in particular non-NS, amino acid residues segment(s), in particular comprising from 1 to 15 amino acid residues, which do not form human T-cell epitopes.

The chimeric polyepitope of the invention comprises or consists of one or more antigenic regions, in particular between 2 and 15 antigenic regions, preferably between 10 and 15 antigenic regions, more preferably 11, 12, 13 or 14 antigenic regions.

As defined herein, the term "antigenic region" refers to a region comprising one or more ZIKV T-cell epitopes, i.e. a group of ZIKV T-cell epitopes. The amino acid sequences of said ZIKV T-cell epitopes may differ by one or more amino acid residues from the amino acid sequences of other ZIKV T-cell epitopes, and/or may have overlapping sequences, and accordingly share some amino acids. In a determined antigenic region, said ZIKV T-cell epitopes are of the same ZIKV protein, in particular are of the C, NS1, NS3, NS4B and NS5 proteins of the ZIKV, preferably are of the NS1, NS3, and NS5 proteins of the ZIKV. The chimeric polyepitope of the invention may comprise one or more different antigenic regions of the same ZIKV protein.

In a particular embodiment of the invention, it is necessary to check that the adjacent amino acid sequences located on both sides of the junction between 2 contiguous antigenic regions do not form new epitopes, in particular new strong human T-cell epitopes. As a consequence, said amino acid sequences consist of no more than 15 amino acid residues and are selected on the basis of the their low binding prediction to the HLA-A*01:01, HLA-A*02:01, HLA-A*03:01, HLA-A*11:01, HLA-A*24:02, HLA-B*07:02, HLA-B*35:01 and HLA-B*40:03, alleles, according to the Immuno Epitope Database (IEDB) analysis resource (http://tools.immuneepitope.org/mhci/). For example, in the fusion between two ZIKV protein fragments, in particular between two ZIKV protein fragments selected from the group consisting of the C, NS1, NS3, NS4B and NS5 proteins of a ZIKV, or between two antigenic regions, the region surrounding the fusion junction comprises a peptide sequence consisting of no more than 15 amino acid residues and which does not form a strong epitope. Thus the junctional peptide may comprise 14 amino acid residues of a first ZIKV protein and 1 amino acid residue of a second ZIKV protein, or 13 amino acid residues of a first ZIKV protein and 2 amino acid residues of a second ZIKV protein, or 12 amino acid residues of a first ZIKV protein and 3 amino acid residues of a second ZIKV protein, or 11 amino acid residues of a first ZIKV protein and 4 amino acid residues of a second ZIKV protein, or 10 amino acid residues of a first ZIKV protein and 5 amino acid residues of a second ZIKV protein, or 9 amino acid residues of a first ZIKV protein and 6 amino acid residues of a second ZIKV protein, or 8 amino acid residues of a first ZIKV protein and 7 amino acid residues of a second ZIKV protein, or 7 amino acid residues of a first ZIKV protein and 8 amino acid residues of a second ZIKV protein, or 6 amino acid residues of a first ZIKV protein and 9 amino acid residues of a second ZIKV protein, or 5 amino acid residues of a first ZIKV protein and 10 amino acid residues of a second ZIKV protein, or 4 amino acid residues of a first ZIKV protein and 11 amino acid residues of a second ZIKV protein, or 3 amino acid residues of a first ZIKV protein and 12 amino acid residues of a second ZIKV protein, or 2 amino acid residues of a first ZIKV protein and 13 amino acid residues of a second ZIKV protein, or 1 amino acid residue of a first ZIKV protein and 14 amino acid residues of a second ZIKV protein. Said first and second ZIKV proteins may be different or identical.

In a particular embodiment of the invention, the chimeric polyepitope has less than 1500 amino acid residues, in particular less than 1000 amino acid residues.

An example of a chimeric polyepitope that can be used in the present invention has an amino acid sequence of SEQ ID NO: 99 consisting of 962 amino acid residues. Said chimeric polyepitope consists of 11 antigenic regions, wherein the first antigenic region is located from amino acid residues 1 to 93 (SEQ ID NO: 102), the second antigenic region is located from amino acid residues 94 to 206 (SEQ ID NO: 104), the third antigenic region is located from amino acid residues 207 to 270 (SEQ ID NO: 106), the fourth antigenic region is located from amino acid residues 271 to 286 (SEQ ID NO: 108), the fifth antigenic region is located from amino acid residues 287 to 331 (SEQ ID NO: 110), the sixth antigenic region is located from amino acid residues 332 to 473 (SEQ ID NO: 112), the seventh antigenic region is located from amino acid residues 474 to 547 (SEQ ID NO: 114), the eighth antigenic region is located from amino acid residues 548 to 766 (SEQ ID NO: 116), the ninth antigenic region is located from amino acid residues 767 to 821 (SEQ ID NO: 118), the tenth antigenic region is located from amino acid residues 822 to 839 (SEQ ID NO: 120) and the eleventh antigenic region is located from amino acid residues 840 to 962 (SEQ ID NO: 122).

The native and optimized sequences of the polynucleotide encoding said chimeric polyepitope are as defined in SEQ ID NOs: 100 and 101 respectively.

Another nucleotide sequence of the polynucleotide encoding said chimeric polyepitope is as defined in SEQ ID NO: 124.

The first antigenic region of said chimeric polyepitope comprises T-cell epitopes of the C protein of ZIKV. The native sequence of the polynucleotide encoding said first antigenic region is as defined in SEQ ID NO: 103.

The second antigenic region of said chimeric polyepitope comprises T-cell epitopes of the NS1 protein of ZIKV. The native sequence of the polynucleotide encoding said second antigenic region is as defined in SEQ ID NO: 105.

The third antigenic region of said chimeric polyepitope comprises T-cell epitopes of the NS1 protein of ZIKV. The native sequence of the polynucleotide encoding said third antigenic region is as defined in SEQ ID NO: 107.

The fourth antigenic region of said chimeric polyepitope comprises T-cell epitopes of the NS1 protein of ZIKV. The native sequence of the polynucleotide encoding said fourth antigenic region is as defined in SEQ ID NO: 109.

The fifth antigenic region of said chimeric polyepitope comprises T-cell epitopes of the NS3 protein of ZIKV. The native sequence of the polynucleotide encoding said fifth antigenic region is as defined in SEQ ID NO: 111.

The sixth antigenic region of said chimeric polyepitope comprises T-cell epitopes of the NS3 protein of ZIKV. The native sequence of the polynucleotide encoding said sixth antigenic region is as defined in SEQ ID NO: 113.

The seventh antigenic region of said chimeric polyepitope comprises T-cell epitopes of the NS4B protein of ZIKV. The native sequence of the polynucleotide encoding said seventh antigenic region is as defined in SEQ ID NO: 115.

The eighth antigenic region of said chimeric polyepitope comprises T-cell epitopes of the NS5 protein of ZIKV. The native sequence of the polynucleotide encoding said eighth antigenic region is as defined in SEQ ID NO: 117.

The ninth antigenic region of said chimeric polyepitope comprises T-cell epitopes of the NS5 protein of ZIKV. The native sequence of the polynucleotide encoding said ninth antigenic region is as defined in SEQ ID NO: 119.

The tenth antigenic region of said chimeric polyepitope comprises T-cell epitopes of the NS5 protein of ZIKV. The native sequence of the polynucleotide encoding said tenth antigenic region is as defined in SEQ ID NO: 121.

The eleventh antigenic region of said chimeric polyepitope comprises T-cell epitopes of the NS5 protein of ZIKV. The native sequence of the polynucleotide encoding said tenth antigenic region is as defined in SEQ ID NO: 123.

The present invention also relates to an association of the chimeric polyepitope of the invention, with a distinct immunogenic polypeptide comprising other ZIKV antigens. Said association of polypeptides may be achieved as a result of expression of the polynucleotides encoding each of said chimeric polyepitope and distinct immunogenic polypeptide, from a vector as disclosed herein. Alternatively, said association may result from an amino acid construct encompassing said chimeric polyepitope and distinct immunogenic polypeptide.

The chimeric polyepitope of the invention can be synthesized chemically, or produced either in vitro (cell free system) or in vivo after expression of the nucleic acid molecule encoding the chimeric polyepitope in a cell system.

To check the correct expression of the chimeric polyepitope of the invention in an in vitro cell system, said chimeric polyepitope may comprise a tag sequence in its 3' end.

In the present invention, the ZIKV protein, in particular the C, NS1, NS3, NS4B or NS5 protein of ZIKV, preferably the NS1, NS3 or NS5 protein of ZIKV, is in particular an antigen designed using a consensus sequence for the ZIKV. In particular, said antigen is designed using the consensus amino acid sequence of Zika viruses as observed circulating from 2013 and onward.

In a particular embodiment of the invention, said ZIKV is from the African lineage, in particular from the African strain ArD158084 (GenBank: KF383119) or African strain ArD128000 (GenBank: KF383117), or African isolate ARB13565 (GenBank: KF268948), or from the Asian lineage, in particular from the Asian strain FLR (GenBank: KX087102), or Asian isolate SSABR1 (GenBank: KU707826), or Asian isolate Z1106031 (GenBank: KU312314), or Asian isolate Bahia07 (GenBank: KU940228), or Asian strain FVM00318/VEN/Maracay/2016 (GenBank: KY693680), or Asian isolate FLR (GenBank: KU820897).

In another particular embodiment of the invention, said ZIKV corresponds to various lineages of ZIK viruses including strains that circulated in the Pacific and Americas since 2013.

In a preferred embodiment of the invention, the C, NS1, NS3, NS4B or NS5 protein of the ZIKV has an amino acid sequence which is a consensus amino acid sequence representative of the C, NS1, NS3, NS4B or NS5 sequences of a selection of various strains of ZIKV including from the Asian lineage, in particular is from the ZIKV strains (GenBank: KX087102, KU707826, KU312314, KU940228, KY693680, KU820897).

The invention also relates to an isolated or purified polynucleotide encoding the chimeric polyepitope according to the invention.

The invention also relates to an isolated or purified polynucleotide encoding the chimeric polyepitope according to the invention, in a nucleic acid construct further comprising a polynucleotide encoding other ZIKV antigens.

As defined herein, the term "isolated or purified" means molecules which have been altered by man from their native state, i.e. if the molecules exist in nature, they have been changed and/or withdrawn from their initial environment. As an example, a polynucleotide naturally present and found in the biological environment of a living organism which naturally expresses it is not "isolated" in this context. However, the same polynucleotide when separated from its natural environment and/or obtained by cloning, amplification and/or chemical synthesis is considered in the present invention to be "isolated". Further, a polynucleotide which is introduced into an organism by transformation, gene manipulation or any other recombination method is "isolated" even if it is present in said organism.

As defined herein, the term "encoding" defines the ability of the nucleic acid molecules to be transcribed and where appropriate translated for product expression into selected cells or cell lines, when said molecule is placed under expression control sequences including promoter for transcription. Accordingly a "polynucleotide encoding" according to the invention is either limited to the nucleic acid having the sequence translated into the amino acid sequence or alternatively when specified comprises also the expression control sequences.

The present invention also relates to a vector, in particular a non-replicating vector, suitable for the delivery of the chimeric polyepitope according to the invention, wherein said vector is a recombinant molecule carrying the polyepitope, or is a viral vector expressing the polyepitope, or a mammalian expression vector expressing the polyepitope such as the pcDNA3 vector, the pcDNA5 vector, the pcDNA6 vector, the pCI vector and the pCMV vector.

The present invention also relates to a vector comprising the polynucleotide according to the invention.

As defined herein, the term "vector" refers to a polynucleotide construct designed for transduction/transfection of one or more cell types. Vectors may be, for example, "cloning vectors" which are designed for isolation, propagation and replication of inserted polynucleotides (designated as the insert), "expression vectors" which are designed for expression of a polynucleotide molecule especially for expression of the insert in a host cell, or a "viral vector" which is designed to result in the production of recombinant virus particles or virus-like particles, or "shuttle vectors", which comprise the attributes of more than one type of vector.

A number of vectors suitable for transduction or for transfection of cells, in particular for stable transfection of cells and bacteria are available to the public (e.g. plasmids, viruses), as are methods for constructing such cell lines. It will be understood that the present invention encompasses any type of vector comprising any of the polynucleotides of the invention.

In a particular embodiment of the invention, the present invention relates to an expression vector, which may be a plasmid comprising as polynucleotide insert(s), one or a plurality of the nucleic acid molecules defined herein. In a particular embodiment, the plasmid comprises as an insert a polynucleotide encoding the chimeric polyepitope of the invention as defined herein and optionally comprises the polynucleotide encoding other ZIKV antigens.

Vectors well known to the skilled person that can be used in the present invention encompass the measles virus vector, in particular live-attenuated measles virus vector (for example, as disclosed in Combredet, C. et al., 2003, *J Virol*, 77(21): 11546-11554, in the European patent application EP17305676.3 and in the international applications WO2004/000876, WO2004/001051, WO2014/049094, WO2015/197565), lentiviral vectors (for example, as disclosed in the international applications WO2005/111221, WO2007/052165, WO2008/078198, WO2009/019612 and WO2016/091836), or mRNA (for example, Moderna's mRNA Therapeutics™ platform; as disclosed in the international applications WO2012135805, WO2013039861 and WO2015/085318 or in Expert Opinion by Youn H. and Chung J K. Expert Opin Biol Ther. 2015 Sep. 2; 15(9): 1337-1348 published online 2015 Jun. 30. doi: 10.1517/14712598.2015.1057563).

The present invention also relates to a host cell transformed with the polynucleotide according to the invention or the vector according to the invention.

The host cell may be genetically transformed with the polynucleotide encoding the chimeric polyepitope of the invention and optionally with the polynucleotide encoding other ZIKV antigens. A particular host cell may thus be genetically transformed with a vector of the invention.

The host cell of the invention may be transfected with a genome vector by methods well known to the man skilled in the art, i.e. by chemical transfection (calcium phospate, lipofectamine), lipid-based techniques (liposome), electroporation, photoporation, use of viral vectors . . . .

In a particular embodiment of the invention, a cell is transformed or transduced with a polynucleotide of the invention, in a way enabling integration of the polynucleotide in the cell genome either by a recombination with the homologous cellular sequence or by insertion in the cellular genome. The transfection, infection or transduction can occur ex vivo, i.e. in an artificial environment outside the living organism.

As used herein, the terms "transfected", "transformed" or "infected" refer to a cell comprising a vector of the invention (transient expression), whereas the term "genetically transformed" refers to a cell whose genome has been definitively modified by a polynucleotide of the invention (permanent expression).

Said transitory or stably transformed cells can be any prokaryotic (bacteria) or eukaryotic (yeast, insect or animal including mammal especially human) cells. In an embodiment, cells are non-human cells. In a particular embodiment, cells of the invention are isolated human cells, "isolated" meaning outside of their natural environment.

In a particular embodiment of the invention, the host cell is an eukaryotic cell, such as an avian cell, in particular a CEF (chick embryo fibroblast) cell, a mammalian cell, in particular HEK-293 (human embryonic kidney) cells, which cell line 293 is deposited with the ATCC under No. CRL-1573 (as disclosed in the international application WO2008/078198), or a yeast cell.

The present invention also relates to an immunogenic composition comprising at least one component selected from the group consisting of:
(i) the chimeric polyepitope according to the invention,
(ii) the polynucleotide according to the invention,
(iii) the vector according to the invention, and
(iv) the host cell according to the invention.

In a particular embodiment of the invention, the immunogenic composition further comprises an adjuvant and/or a pharmaceutically acceptable vehicle.

In another particular embodiment of the invention, the immunogenic composition further comprises a polynucleotide encoding other ZIKV antigens.

In a particular embodiment of the invention, the immunogenic composition does not comprise an adjuvant and/or a pharmaceutically acceptable vehicle.

As defined herein, a pharmaceutically acceptable vehicle encompasses any substance that enables the formulation of the polyepitope, the polynucleotide, the vector according to the invention within a composition. A vehicle is any substance or combination of substances physiologically acceptable i.e., appropriate for its use in a composition in contact with a host, especially a human, and thus non-toxic. Examples of such vehicles are phosphate buffered saline solutions, distilled water, emulsions such as oil/water emulsions, various types of wetting agents sterile solutions and the like.

As defined herein, an adjuvant includes, for example, liposomes, oily phases, such as Freund type adjuvants, generally used in the form of an emulsion with an aqueous phase or can comprise water-insoluble inorganic salts, such as aluminium hydroxide, zinc sulphate, colloidal iron hydroxide, calcium phosphate or calcium chloride.

In another particular embodiment of the invention, the immunogenic composition is formulated for an administration through parenteral route such as subcutaneous (s.c.), intradermal (i.d.), intramuscular (i.m.), intraperitoneal (i.p.) or intravenous (i.v.) injection.

In another particular embodiment of the invention, the immunogenic composition is administered in one or multiple administration dose(s), in particular in a prime-boost administration regime.

The quantity to be administered (dosage) depends on the subject to be treated, including the condition of the patient, the state of the individual's immune system, the route of administration and the size of the host. Suitable dosages range from $10^3$ TCID50 to $10^7$ TCID50 for a viral vector or 100 micrograms of the plasmid DNA, and can be modified by one skilled in the art, depending on circumstances.

The present invention also relates to a vaccine composition comprising at least one component selected from the group consisting of:
(i) the chimeric polyepitope according to the invention,
(ii) the polynucleotide according to the invention,
(iii) the vector according to the invention, and
(iv) the host cell according to the invention.

In a preferred embodiment of the invention, the immunogenic or vaccine composition is for use in the prevention of a ZIKV infection in a human subject or (ii) for use in the prevention of ZIKV and Dengue virus (DENV) infections in a human subject.

The present invention also relates to the induction of immune responses in vivo against the epitopes of the ZIKV polyepitope, in mice expressing the human HLA class I alleles: HLA-A*02:01, or HLA-A*24:02, or HLA-B*07:02 or HLA-B*35:01. The immunization of mice is performed following a prime boost administration regimen, with a first intradermal injection of plasmid DNA encoding the ZIKV polyepitope (2 simultaneous intradermal injections of 50 micrograms plasmid DNA in the lower back, followed by in vivo electroporation, using a pre-defined procedure), followed by a boost immunization 3 weeks later (2 intradermal injections of 50 micrograms plasmid DNA in the lower back, and electroporation, using the same pre-defined procedure). The electroporation settings, using the AgilePulse apparatus (BTX, Harvard apparatus) consist of 3 Voltage groups: including the first one with 450V, a pulse length of 50 microseconds, a pulse interval of 0.2 microseconds and 1 pulse, the second one with 450V, a pulse length of 50 microseconds, a pulse interval of 50 microseconds and 1 pulse, and a third one with 110V, a pulse length of 10 milliseconds, a pulse interval of 20 milliseconds and 8 pulses. Ten days after the boost immunization, the spleen of the immunized mice are taken and spleen cells are tested for their ability to secrete Interferon gamma in response to in vitro stimulation with the specific peptides derived from the ZIKV polyepitope, according to the ELISPOT assay.

Other features and advantages of the invention will be apparent from the examples which follow and will also be illustrated in the figures.

BRIEF DESCRIPTION OF THE DRAWINGS

Figure 4:
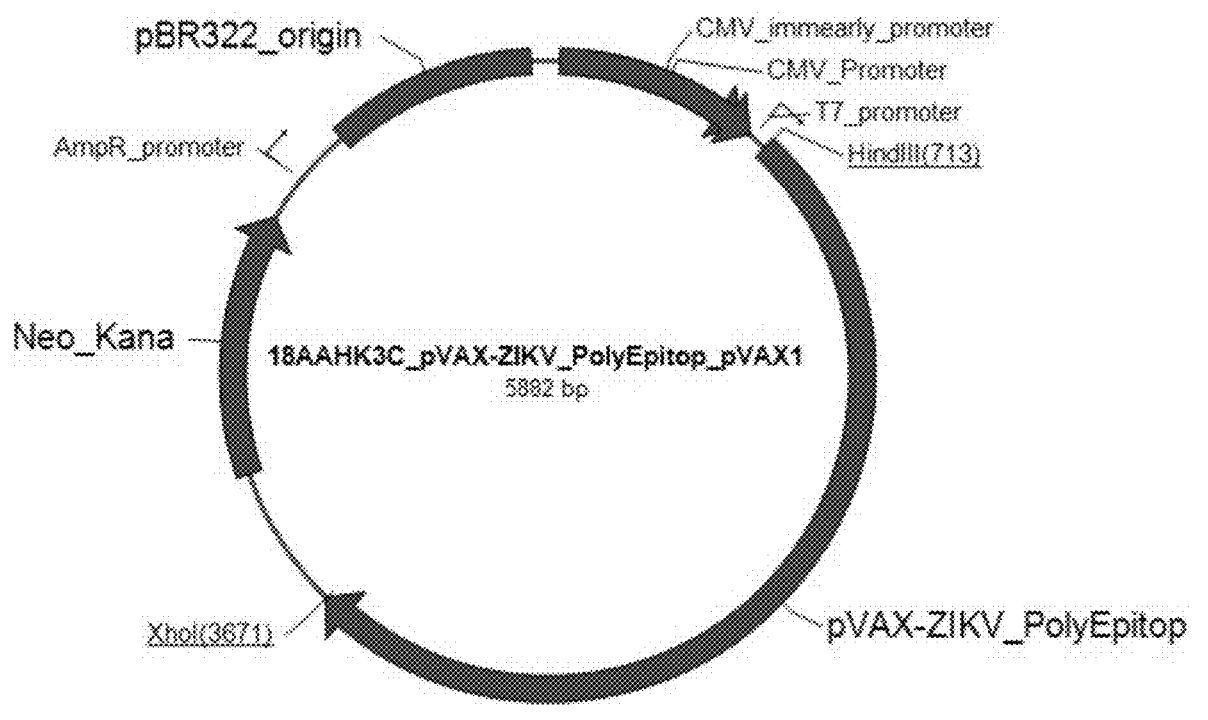

FIG. 4. Schematic representation of the 18AAHK3C_pVAX-ZIKV_PolyEpitop_pVAX1 plasmid. The inventors used the pVAX1 plasmid commercialized by Thermo Fisher Scientific. The polynucleotide encoding a chimeric polyepitope of ZIKV as defined in SEQ ID NO: 124 was inserted in said plasmid.

EXAMPLES

Ethics Statement

Figure 1A:
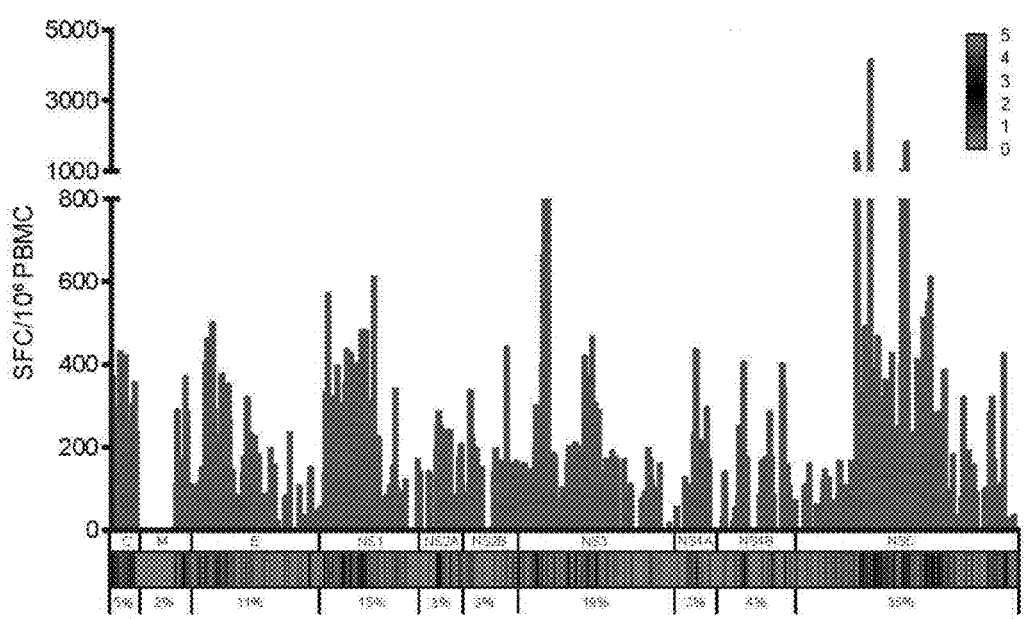
FIG. 1A-C. ZIKV-specific response magnitude and frequency of responding donors. Cumulative IFN-γ responses (as spot-forming cells (SFCs) per million cells) for each overlapping peptide spanning the ZIKV proteome is shown for (1A) all donors, (1B) ZIKV donors or (1C) DENV/ZIKV donors. The heat map indicates the number of donors with a positive IFN-γ response to each peptide within each protein (C, capsid; M, membrane; E, envelope, NS1, NS2A, NS2B, NS3, NS4A, NS4B, and NS5). The numbers below each graph represent percentages of the total response for each protein.

Human blood samples were obtained from healthy adult donors from the Fundación Hematologica Colombia (Bogota D.C., Colombia) in an anonymous manner. All protocols described in this study were approved by the institutional review board (IRB) of the EL Bosque University (Colombia).

Human Blood Samples

Donors were of both sexes and between 20 and 60 years of age. A total of 82 samples were obtained from different ZIKV-endemic areas near Bogota D.C. (mainly from Villavicencio, Meta) over a time course of three months between October and December 2016. PBMCs were purified by density gradient centrifugation (Lymphoprep™; Stemcell technologies) and resuspended in FBS (Gibco) containing 10% dimethyl sulfoxide and cryopreserved in liquid nitrogen. Eleven of the 82 blood samples obtained had to be excluded from the study due to poor viability of cells.

Viruses and Cell Lines

The in vitro assays were conducted using the DENV1 KDH0026A (provided by Dr L. Lambrecht, Institut Pasteur, Paris), DENV2 R0712259 (provided by Dr. A. Failloux, Institut Pasteur, Paris), DENV3 KDH0010A (provided by Dr. L. Lambrecht, Institut Pasteur, Paris), DENV4 CRBIP10.4VIMFH4 (from the Institut Pasteur Collection) and ZIKV KU312312 (provided by Dr. Dominique Rousset, Institut Pasteur. Cayenne). All viruses were grown using the Aedes Albopictus mosquito cell line C6/36 cultured in Leibovitz's L-15 medium supplemented with 10% fetal bovine serum containing 0.1 mM non-essential amino acids and 1× tryptose phosphate broth. Vero-E6 cells and DC-SIGN-expressing U937 were kindly provided by Dr M. Flamand and Dr B. Jacquelin (Institut Pasteur, Paris), respectively.

HLA Typing

Genomic DNA isolated from PBMCs of the study subjects by standard techniques (QIAmp; Qiagen) was used for HLA typing. High resolution Luminex-based typing for HLA class I (alleles A, B and C) and HLA class II (allele DRB1) was used according to the manufacturer's protocol (Sequence-Specific Oligonucleotides (SSO) typing; Immucor, Lifecodes).

Serology

ZIKV seropositivity was determined using a recombinant antigen-based (EDIII antigen) indirect ELISA, as previously described (Aubry M, et al. 2017, Emerging infectious diseases 23(4):669-672). Briefly, 96-well plates (Nunc, Life Technologies, Rochester, NY) were coated overnight at 4° C. with 50 ng of antigen in PBS. After washing, 200 µl PBS containing 3% skimmed milk and 0.1% Tween-20 were added for 1 hr at 37°. The blocking solution was replaced by 100 µl of plasma diluted 1:500 in PBS containing 1.5% BSA and 0.1% Tween-20, and plates were incubated at 37° C. for 60 min. After three washes, bound antibodies were detected with a horseradish peroxidase-conjugated goat anti-human IgG immunoglobulin (ROCKLAND). Following incubation at 37° C. for 1 hr and three washes, 100 µl of a substrate solution containing TMB (KPL, Eurobio) were added. After 15 min incubation, the optical density (OD) was determined at 650 nm with an automated plate reader (Tecan infinite 200 pro). Each plasma sample was tested in duplicate. Plasma samples obtained from individuals with positive DENV IgG serology collected before the ZIKV outbreak were used as negative controls. The cut-off was calculated from the negative controls and was 0.196. DENV seropositivity was determined by indirect ELISA for IgGs (Panbio; Alere) and by capture ELISA for IgM (Tecnosuma) following the manufacturer's instructions. For further characterization of seropositive donors, and to confirm the specificity of the ELISA, a flow cytometry-based neutralization assay was performed as described previously (Andreatta M, et al. 2015, *Immunogenetics* 67(11-12):641-650; Nielsen M & Andreatta M 2016, *Genome Med* 8(1):33). Briefly, 10-fold serial dilutions of plasma samples were incubated at 37° C. for 1 hour with a dilution of virus inducing 7-15% infection. Virus-antibody mixture was then added to U937-DC-SIGN cells for neutralization of DENV1-4 infection, or to Vero cells for neutralization of ZIKV infection, for 2 hours at 37° C. after which cells were washed 2 times with fresh medium and then incubated for 24 h. The cells were then fixed with 4% paraformaldehyde, stained with 4G2 antibody conjugated to Alexa-488, and the percentage of infected cells was measured by flow cytometry. The neutralization titer of antibodies was expressed as the reciprocal dilution of plasma at which 50% of the virus was inhibited. Plasma samples from donors collected before ZIKV outbreak or from negative samples provided from the Kits to detect anti-DENV antibodies did not reveal any neutralization activity against ZIKV or DENV infection, respectively. Following the ELISA and neutralization assays, from the 71 plasma samples selected for this study, a total of nine samples from ZIKV-seropositive individuals and eleven samples from DENV/ZIKV-seropositive individuals were further selected for ELISPOT analysis. The full list of the twenty blood donors included in this study is listed in Table 1.

Viral Sequences

The identical amino acid sequence of ZIKV from Colombia (GenBank KX087102 and KU820897) was used as a reference for the set of overlapping 15-mer peptides.

A total of 50 full length protein coding DENV sequences from Colombia (serotype 1: 14 sequences; serotype 2: 16 sequences; serotype 3: 13 sequences; serotype 4: 7 sequences) were retrieved from GenBank and used for pairwise sequence identity comparisons.

Peptides

All peptides were synthesized by Mimotopes (Victoria, Australia). A total of 853 15-mer peptides overlapping by 11 amino acids and 197 9-mer peptides overlapping by eight amino acids were tested by ELISPOT assay. For the identification of T-cell epitopes, 15-mer peptides were combined into pools of 12 peptides, and individual peptides from the positive pools were tested in a second ELISPOT assay. Following the identification of the positive 15-mer peptides, and according to their HLA class I or class II restriction potential (predicted or shared between at least two donors), 9-mer peptides were synthesized and tested individually.

Ex Vivo IFN-γ ELISPOT Assay

PBMCs ($2 \times 10^5$) were incubated in 96-well flat bottom plates (MSIPS 4510, Millipore, Bedford, Mass.) coated with anti-IFN-γ mAb (clone 1-D1K, Mabtech, Sweden) with 0.2 ml of complete RPMI containing 10% human AB serum with pools of 12 peptides (2 µg/ml, final concentration) or individual peptides (1 µg/ml, final concentration) for 20 hours. Following a 20h-incubation at 37° C., the wells were washed with PBS/0.05% Tween 20 and then incubated with biotinylated anti-IFN-γ mAb (clone 7-B6-1, Mabtech) for 1 h 30 mn. The spots were developed using Streptavidin-alkaline phosphatase (Mabtech) and BCIP/NBT substrate (Promega, France) and counted using an automated ELISPOT reader (Immunospot, Cellular Technology Limited, Germany). The number of IFN-γ-producing cells was expressed as spot forming cells (SFC) relative to $1 \times 10^6$ PBMCs. Values were calculated by subtracting the number of spots detected in the non-stimulated control wells. Values were considered positive if they were equal to or greater than 20 spots and at least three times above the means of the unstimulated control wells. As a positive control, cells were stimulated with CEF peptide pool (Mabtech).

Immunogenicity and HLA Restrictions Prediction

The evaluation of binding possibilities of peptides to MHC class I and class II alleles was analyzed using the NetMHCpan3.0 and NetMHCIIpan3.1 servers, respectively (Andreatta M, et al. 2015, *Immunogenetics* 67(11-12):641-650; Nielsen M & Andreatta M 2016, *Genome Med* 8(1):33).

Statistics

All data were analyzed with Prism software version 7.0 (GraphPad Software). Statistical significance was determined using the nonparametric two-tailed Mann-Whitney test to compare two independent groups. Differences were considered significant at $P<0.05$.

Results

Identification of Immunodominant Regions of the ZIKV Proteome

Figure 1B:
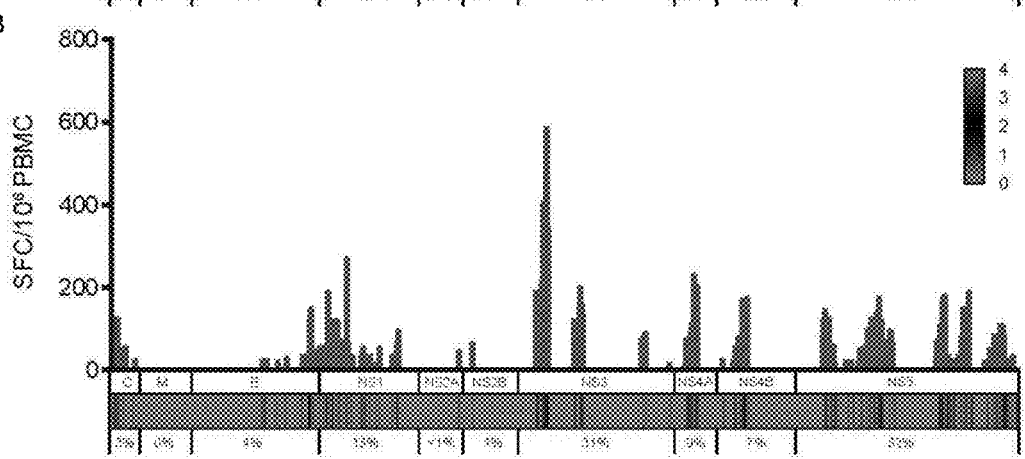
Figure 1C:
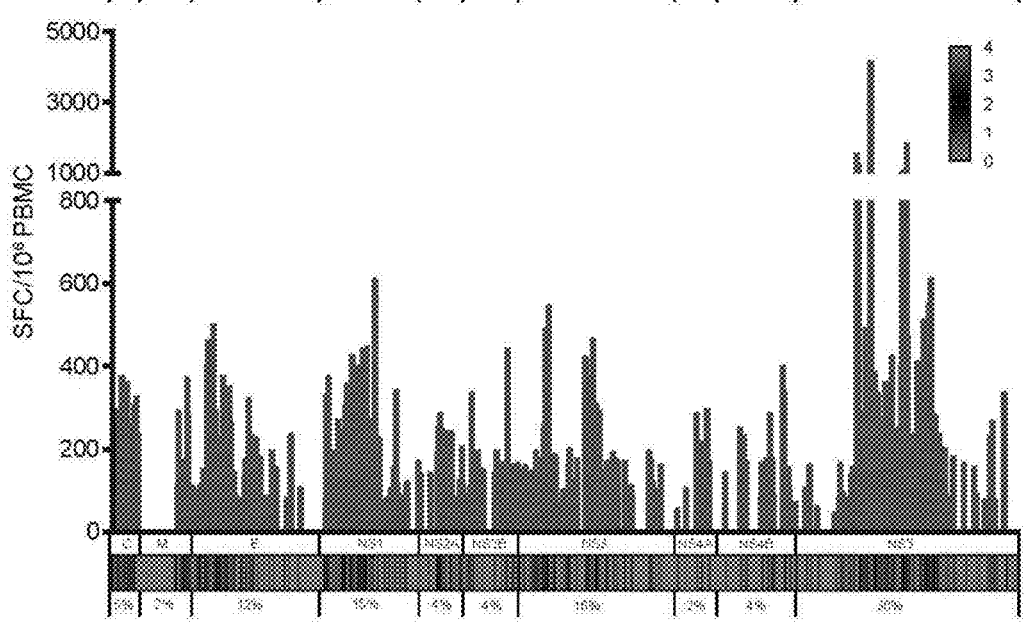

To investigate T-cell immunity induced after ZIKV infection, the inventors examined responses from blood donors living in a ZIKV endemic area in gamma interferon (IFN-γ)-specific enzyme-linked immunosorbent spot (ELISPOT) assays. Blood samples from all study participants were tested for the presence of ZIKV IgG and DENV IgM and IgG by ELISA, and for the presence of virus-specific antibodies by flow cytometry-based neutralization assay against ZIKV and the 4 DENV serotypes, and PBMCs from ZIKV-seropositive individuals were HLA-typed. Details of the blood donors included in this study are listed in Table 1. PBMCs from 20 ZIKV-seropositive donors were screened for T-cell reactivity against pools of 15-mer peptides (overlapping by 11 amino acids) spanning the entire ZIKV proteome. Analysis of the response magnitude (as spot forming cells (SFC) per $10^6$ cells) and frequency of responding donors revealed that the non-structural (NS) proteins NS1, NS3 and NS5 were the most vigorously and frequently recognized proteins, and accounted for 69% of the total response (FIG. 1A). Strikingly, these NS1, NS3 and NS5 proteins represented 15%, 19% and 35% of the total response, respectively, in ZIKV donors, whereas the NS3, NS4B and NS5 proteins have been reported to account for 31%, 15% and 22% of the DENV-specific T-cell response, respectively (Simmons C P, et al. 2005, *J. Virol.* 79(9):5665-5675; Duangchinda T, et al. 2010, *Proc Natl Acad Sci USA* 107(39):16922-16927; Rivino L, et al. 2013, *J. Virol.* 87(5):2693-2706; Weiskopf D, et al. 2013, *Proc Natl Acad Sci USA* 110(22):E2046-2053). As these donors were selected in DENV- and ZIKV-endemic areas, and as these viruses share an overall 43% protein sequence identity (with up to 68% for the non-structural proteins), the inventors sought to distinguish between the ZIKV-specific epitopes and those shared by both viruses. Among the 20 ZIKV-seropositive blood donors, 11 individuals had both anti-DENV and anti-ZIKV IgG antibodies and 9 individuals did not reveal any detectable anti-DENV antibodies (Table 1). The inventors thus analyzed separately T-cell responses from donors having only a history of ZIKV infection (ZIKV donors) and those from donors having a history of DENV and ZIKV infections (DENV/ZIKV donors). As shown in FIGS. 1B and 1C, the NS1, NS3 and NS5 proteins accounted for 13%, 31% and 32% of the responses in ZIKV donors, respectively, whereas they accounted for 15%, 16% and 36% of the responses in DENV/ZIKV donors. These results confirmed that NS1, NS3 and NS5 were the main targets for T cells in ZIKV-infected donors, regardless of a previous infection with DENV, and revealed an increase in the frequency and magnitude of the response against NS5 in donors previously infected with DENV, in comparison with donors infected with ZIKV only.

From the 853 peptides spanning the entire ZIKV proteome, 410 peptides elicited a significant T-cell response, some of which being recognized by multiple donors. For most antigenic peptides, the HLA class I and class II alleles of the responding donors coincided with the alleles predicted to bind to this epitope (Andreatta M, et al. 2015, *Immunogenetics* 67(11-12):641-650; Nielsen M & Andreatta M 2016, *Genome Med* 8(1):33). Among the epitopes inducing a strong response in ZIKV and DENV/ZIKV donors, several 15-mer peptides contained short sequences predicted to bind strongly to at least one allele expressed by the responding donors (Table 2). For instance, the $NS2B_{117-131}$ peptide (having the amino acid sequence as defined in SEQ ID NO: 25) contained a 10-mer sequence (having the amino acid sequence as defined in SEQ ID NO: 26) predicted to bind strongly to the HLA-A*0301 and -A*1101 molecules expressed by the responding donor 55. In other cases, multiple responding donors expressed at least one common allele with strong potential for binding to the stimulating peptide. This hold for the $E_{455-469}$ peptide (having the amino

TABLE 1

Characteristics of the ZIKV patient cohort used for the epitope reactivity study.

| Donor[a] | Age (yr) | Gender | HLA Genotyping | | | | Serological test | | | Neutralizing activity (Neut50)[c] | | | | |
|---|---|---|---|---|---|---|---|---|---|---|---|---|---|---|
| | | | HLA-A | HLA-B | HLA-C | DRB1 | DENV IgM | DENV IgG | ZIKV IgG | DENV1 | DENV2 | DENV3 | DENV4 | ZIKV |
| 1 | 41 | Male | 02:01:01 | 35:43:01 | 01:02:01 | 04:07:01 | − | − | + | 17 | 23 | 16 | 25 | 311 |
| | | | 24:02:01 | 51:01:01 | 01:02:01 | 12:01:01 | | | | | | | | |
| 16 | 20 | Female | 01:01:01 | 15:17:01 | 07:01:01 | 13:01:01 | − | + | + | 158 | 79 | 47 | 357 | 2270 |
| | | | 03:01:01 | 38:01:01 | 12:03:01 | 13:02:01 | | | | | | | | |
| 20 | 28 | Female | 01:01:01 | 07:02:01 | 07:02:01 | 04:11:01 | + | + | + | 2049 | 452 | 214 | 438 | 2470 |
| | | | 31:01:02 | 39:05:01 | 07:02:01 | 15:01:01 | | | | | | | | |
| 21 | 26 | Male | 31[b] | 35:01 | 01[b] | 04:01:01 | − | − | + | 13 | 13 | 19 | 14 | 566 |
| | | | 03:01 | 18:01 | 17:02 | 03:01 | | | | | | | | |
| 26 | 29 | Male | 02:01:01 | 07:02:01 | 01:02:01 | 14:02:01 | − | + | + | 5397 | 601 | 735 | 235 | 2476 |
| | | | 24:02:01 | 48:01:01 | 07:02:57 | 15:01:01 | | | | | | | | |
| 28 | 35 | Female | 02:17:01 | 40:02:01 | 03:05 | 04:11:01 | − | + | + | 75 | 39 | 24 | 67 | 5587 |
| | | | 29:02:01 | 44:03:01 | 16:01:01 | 07:01:01 | | | | | | | | |
| 33 | 32 | Female | 24:02:01 | 15:46 | 01:02:01 | 04:07:01 | − | + | + | 306 | 114 | 63 | 51 | 829 |
| | | | 24:02:01 | 35:31 | 03:05 | 04:07:01 | | | | | | | | |
| 35 | 39 | Female | 24:02:01 | 14:01:01 | 03:05 | 01:03 | − | − | + | 11 | 13 | 10 | <10 | 340 |
| | | | 68:01:02 | 40:02:01 | 05:129 | 08:02:01 | | | | | | | | |
| 37 | 34 | Male | 02:45 | 35:01:01 | 04:01:01 | 01:03 | − | − | + | 18 | 12 | 35 | 12 | 280 |
| | | | 11:01:01 | 50:01:01 | 06:02:01 | 13:01:01 | | | | | | | | |
| 42 | 40 | Male | 26:01:01 | 35:01:01 | 04:01:01 | 04:02:01 | − | − | + | 11 | 12 | 25 | 12 | 1689 |
| | | | 26:01:01 | 38:01:01 | 06:76:02 | 11:04:01 | | | | | | | | |
| 46 | 25 | Male | 32:01:01 | 39:01:01 | 06:02:01 | 04:07:01 | − | − | + | 14 | 11 | 12 | 11 | 903 |
| | | | 68:01:02 | 50:01:01 | 07:02:01 | 07:01:01 | | | | | | | | |
| 53 | 54 | Female | 23:01:01 | 40:02:01 | 01:10 | 07:01:01 | − | + | + | 464 | 116 | 29 | 543 | 3081 |
| | | | 31:01:02 | 44:03:01 | 04:01:01 | 08:02:01 | | | | | | | | |
| 55 | 23 | Male | 03:01:01 | 35:01:01 | 04:11:01 | 01:01:01 | − | + | + | 2395 | 612 | 222 | 301 | 3196 |
| | | | 11:01:01 | 51:01:01 | 15:02:01 | 07:01:01 | | | | | | | | |
| 56 | 28 | Female | 02:01:01 | 15:17:01 | 05:01:01 | 03:01:01 | − | + | + | 215 | 55 | <10 | 156 | 110 |
| | | | 02:01:01 | 18:01:01 | 07:01:01 | 11:01:01 | | | | | | | | |
| 59 | 26 | Male | 03:01:01 | 35:43:01 | 01:02:01 | 04:01:01 | − | − | + | 31 | 30 | 16 | 24 | 194 |
| | | | 24:02:01 | 40:01:01 | 03:04:01 | 04:07:01 | | | | | | | | |
| 60 | 20 | Female | 02:05:01 | 55:01:01 | 01:02:01 | 11:01:01 | − | − | + | 11 | <10 | 10 | 10 | 514 |
| | | | 69:01 | 58:01:01 | 07:01:01 | 13:03:01 | | | | | | | | |
| 63 | 24 | Female | 02:01:01 | 07:02:01 | 07:02:01 | 15:01:01 | − | + | + | 999 | 187 | 126 | 144 | 4057 |
| | | | 23:01:01 | 51:08:01 | 17:02:01 | 15:03:01 | | | | | | | | |
| 66 | 21 | Female | 02:01:01 | 39:01:01 | 03:02:01 | 08:02:01 | − | + | + | 2572 | 471 | 1386 | 167 | 2905 |
| | | | 03:01:01 | 40:02:01 | 07:29:01 | 15:01:01 | | | | | | | | |
| 69 | 25 | Male | 01:01:01 | 35:01:01 | 01:02:01 | 04:07:01 | + | + | + | 749 | 463 | 961 | 92 | 1205 |
| | | | 24:02:01 | 35:43:01 | 04:01:01 | 13:05:01 | | | | | | | | |
| 77 | 18 | Female | 02:01:01 | 40:02:01 | 04:01:01 | 13:01:01 | − | − | + | 17 | 12 | 15 | 33 | 110 |
| | | | 02:01:01 | 51:01:01 | 07:01:01 | 14:02:01 | | | | | | | | |

[a]Donors 16, 20, 26, 28, 33, 53, 55, 56, 63, 66, and 69 had previous DENV infection
[b]Allelic variant was not determined
[c]The values in each cell are the 50% neutralization titers determined from two replicates of one experiment. The highest titers for each sample is indicated in boldface acid sequence as defined in SEQ ID NO: 7) in the envelope that contained the 9-mer (having the amino acid sequence as defined in SEQ ID NO: 9) and the 10-mer (having the amino acid sequence as defined in SEQ ID NO: 8) sequences predicted to bind to the HLA-B*5101 and HLA-A*0201 alleles, both alleles being expressed by the responding donors 1 and 77. This also applied to the $NS5_{13-27}$ peptide (having the amino acid sequence as defined in SEQ ID NO: 46), which induced a strong response in donors 55 and 69 that shared the HLA-B*3501 allele, this allele being predicted to bind to the 9-mer peptide MSALEFYSY (having the amino acid sequence as defined in SEQ ID NO: 47) with a high affinity. Interestingly, this epitope was also shown to induce a significant response in transgenic mice carrying the HLA-A*0101 molecule, which was expressed by donor 69 (Wen J, et al. 2017, Nat Microbiol 2:17036). Similarly, a strong T-cell response was observed against the $NS5_{546-560}$ peptide (having the amino acid sequence as defined in SEQ ID NO: 67) in donors 28, 53, and 66 that expressed the HLA-B*4002 and -B*4403 alleles and against the $NS5_{605-619}$ peptide (having the amino acid sequence as defined in SEQ ID NO: 72) in donors 33 and 59 that shared the predicted HLA-A*2402 allele. Finally, the inventors also identified several 9-mer immunodominant epitopes in the NS4B and NS5 proteins, included in the $NS4B_{112-126}$ (having the amino acid sequence as defined in SEQ ID NO: 41), the $NS5_{293-307}$ (having the amino acid sequences as defined in SEQ ID NOs: 49 and 50), $NS5_{297-311}$ (having the amino acid sequences as defined in SEQ ID NOs: 53-55) and $NS5_{345-359}$ (having the amino acid sequence as defined in SEQ ID NO: 58) peptides, which induced substantial T-cell responses in donors that shared one or several alleles with a strong potential for binding to these peptides.

Remarkably, among the NS3 and NS5 proteins, several epitopes have been already described as immunodominant epitopes, either predicted or validated experimentally after DENV infection or vaccination in humans or after ZIKV infection in mice (Wen J, et al. 2017, Nat Microbiol 2:17036; Dar H, et al. 2016, Asian Pac J Trop Med 9(9):844-850; Weiskopf D, et al. 2015, J. Virol. 89(1):120-128; Dikhit M R, et al. 2016, Infection, genetics and evolution: journal of molecular epidemiology and evolutionary genetics in infectious diseases 45:187-197). Indeed, among the 9-mer peptides identified in DENV/ZIKV donors, the $NS5_{293-307}$ (having the amino acid sequences as defined in SEQ ID NOs: 49 and 50), $NS5_{297-311}$ (having the amino acid sequences as defined in SEQ ID NOs: 53-55) and $NS5_{345-359}$ (having the amino acid sequence as defined in SEQ ID NO: 58) have been already detected in PBMCs from HLA-B*3501 individuals, after infection with DENV1, DENV2, or vaccination with DENV live attenuated vaccine (DLAV), with a lysine-to-arginine and a phenylalanine-to-tyrosine amino acid substitution at residues 302 and 350 in the $NS5_{297-311}$ (having the amino acid sequences as defined in SEQ ID NOs: 53-55) and $NS5_{345-359}$ (having the amino acid sequence as defined in SEQ ID NO: 58) peptides from ZIKV, respectively (Rivino L, et al. 2013, J. Virol. 87(5):2693-2706; Weiskopf D, et al. 2015, J. Virol. 89(1):120-128; Imrie A, et al. 2007, J. Virol. 81(18):10081-10091) (Table 2). These results obtained from DENV/ZIKV donors thus confirmed that these NS5 peptides contained nested epitopes restricted by the HLA-B*3501 molecule. Yet the 15-mer $NS3_{219-233}$ peptide (having the amino acid sequence as defined in SEQ ID NO: 28), which contained the APTRVVAAEM epitope (having the amino acid sequence as defined in SEQ ID NO: 29), induced a substantial response in 2 DENV/ZIKV donors that expressed neither HLA-B*0702 nor B*3501, although these alleles were expressed in responding donors vaccinated with DLAV or in ifnar-/- HLA-B*0702 transgenic mice after ZIKV infection (Wen J, et al. 2017, Nat. Microbiol. 2:17036; Weiskopf D, et al. 2015, J. Virol. 89(1):120-128). This suggested that the $NS3_{219-233}$ peptide (having the amino acid sequence as defined in SEQ ID NO: 28) contained another epitope or a promiscuous epitope that bound to other HLA alleles, besides HLA-B*0702 or B*3501.

TABLE 2

Characteristics of antigenic peptides from ZIKV (having the amino acid sequences as defined in SEQ ID NOs: 1-75) identified in this study.

| Peptide[a] | Sequence[b] | Donors | HLA[c] | SFC/million PBMC[d] 15-mer | SFC/million PBMC[d] 9-mer | Predicted epitope | Predicted HLA | Score (rank)[e] |
|---|---|---|---|---|---|---|---|---|
| $C_{13-27}$ | IVNMLKRGVARVSPF | 28 | A02,29; B40,44; C03,16; DRB104,07 | 170 | <20 | MLKRGVARV | A0217 | 1.9 |
| | | 60 | A02,69; B55,58; C01,07; DRB111,13 | 50 | 60 | | A0205 | 1.3 |
| $C_{85-99}$ | KKDIAAMLRIINARK | 26 | A02,24; B07,48; C01,07; DRB114,15 | 100 | <20 | AAMLRIINA | A0201 | 4.5 |
| | | 60 | A02,69; B55,58; C01,07; DRB111,13 | <20 | 75 | KDLAAMLRI | B5501 | 1.4 |
| | KKDLAAMLRIINARK | 28 | A02,29; B40,44; C03,16; DRB104,07 | 230 | 65 | | B4002 | 2.0 |
| $E_{455-469}$ | GMSWFSQILIGTLLM | 1 | A02,24; B35,51; C01,01; DRB104,12 | 120 | NT | GMSWFSQILI | A0201 | 0.9 |
| | | 77 | A02.02; B40,51; C04,07; DRB113,14 | 35 | NT | MSWFSQILI | B5101 | 0.12 |
| $NS1_{63-77}$ | MENIMWRSVEGELNA | 21 | A31,03; B35,18; C01,17; DRB104,03 | 65 | 50 | MENIMWRSVEGELNA | DRB10405 | 50 |
| | MENIMWRSVEGELNA | 28 | A02,29; B40,44; C03,16; DRB104,07 | 245 | 58 | IMWRSVEGEL | A0217 | 0.5 |
| | | 56 | A02.02; B15,18; C05,07; DRB103,11 | 70 | 148 | | A0201 | 1.2 |

TABLE 2-continued

Characteristics of antigenic peptides from ZIKV (having the amino acid sequences as defined in SEQ ID NOs: 1-75) identified in this study.

| Peptide[a] | Sequence[b] | Donors | HLA[c] | SFC/million PBMC[d] 15-mer | SFC/million PBMC[d] 9-mer | Predicted epitope | Predicted HLA | Score (rank)[e] |
|---|---|---|---|---|---|---|---|---|
| $NS1_{83-97}$ | GVQLTVVVGSVKNPM | 26 | A02,24; B07,48; C01,07; DRB114,15 | 145 | 23 | VQLTVVVGSV | A0201 | 1.7 |
|  |  | 28 | A02,29; B40,44; C03,16; DRB104,07 | 165 | 35 |  | A0217 | 3 |
| $NS1_{163-177}$ | FHTSVWLKVREDYSL | 28 | A02,29; B40,44; C03,16; DRB104,07 | 230 | 75 | HTSVWLKVREDY | A0101 | 0.4 |
|  | FHTSVLKVREDYSL | 55 | A03,11; B35,51; C04,15; DRB101,07 | 110 | 125 | HTSVWLKVR | A3101 | 0.4 |
|  |  | 46 | A32,68; B39,50; C06,07; DRB104,07 | 50 | 32 |  | A6801 | 0.6 |
|  |  | 20 | A01,31; B07,39; C07,07; DRB104,15 | 310 | 105 | VWLKVREDY | A2902 | 1.3 |
|  |  |  |  |  |  | FHTSVWLKV | B3905 | 0.4 |
|  |  |  |  |  |  |  | B3901 | 0.4 |
| $NS1_{275-289}$ | IRFEEPGTKVHVEE | 33 | A24,24; B15,35; C01,03; DRB104,04 | 215 | 55 | CPGTKVHVE | B3501 | 8.5 |
|  |  | 55 | A03,11; B35,51; C04,15; DRB101,07 | 130 | 115 |  | B3531 | 6.5 |
| $NS2B_{117-131}$ | AAGAWYVYVKTGKRS | 55 | A03,11; B35,51; C04,15; DRB101,07 | 445 | NT | AAGAWYVYVK | A0301 | 0.6 |
|  |  |  |  |  |  |  | A1101 | 0.12 |
|  |  |  |  |  |  | YVYVKTGKR | A0301 | 1.8 |
| $NS3_{219-233}$ | TVILAPTRVVAAEME | 53 | A23,31; B40,44; C01,04; DRB107,08 | 100 | NT | TVILAPTRVVAAEME | DRB10802 | 1.5 |
|  |  | 66 | A02,03; B39,40; C03,07; DRB108,15 | 65 | NT | ILAPTRVVAA | A0201 | 1.6 |
| $NS3_{271-285}$ | LQPIRVPNYNLYIMD | 42 | A26,26; B35,38; C05,06; DRB104,11 | 165 | NT | VPNYNLYIM | B3501 | 0.06 |
| $NS3_{311-325}$ | AAIMTATPPGTRDA | 28 | A02,29; B40,44; C03,16; DRB104,07 | 255 | 85 | AAIFMTATPPGTRDA | DRB10401 | 4 |
|  | AAIFMTATPPGTRDA | 33 | A24,24; B15,35; C01,03; DRB104,04 | 215 | 30 | FMTATPPGT | A0217 | 5.5 |
|  |  |  |  |  |  | IFMTATPPG | A2402 | 5 |
| $NS4A_{86-100}$ | VTLGASAWLMWLSEI | 55 | A03,11; B35,51; C04,15; DRB101,07 | 178 | NT | SAWLMWLSEI | B5101 | 0.9 |
|  |  | 60 | A02,69; B55,58; C01,07; DRB111,13 | 125 | NT | VTLGASAWL | A6901 | 1.3 |
|  |  |  |  |  |  | LGASAWLMW | B5801 | 0.07 |
| $NS4B_{112-126}$ | AIILLVAHYMYLIPG | 28 | A02,29; B40,44; C03,16; DRB104,07 | 60 | 58 | AIILLVAHY | A2902 | 0.6 |
|  |  | 37 | A02,11; B35,50; C04,06; DRB101,07 | 75 | 30 |  | A1101 | 3.5 |
|  | AIILLVAHYMYLPG | 60 | A02,69; B55,58; C01,07; DRB111,13 | 100 | 68 | LLVAHYMYL | A0205 | 0.3 |
|  | AIILLVAHYMYLIPG | 60 | A02,69; B55,58; C01,07; DRB111,13 | 100 | 35 | LVAHYMYLI | A6901 | 0.15 |
|  |  |  |  |  |  |  | A0205 | 0.2 |
| $NS5_{13-27}$ | KARLNQMSALEFYSY | 55 | A03,11; B35,51; C04,15; DRB101,07 | 260 | NT | MSALEFYSY | B3501 | 0.15 |
|  |  | 69 | A01,24; B35,35; C01,04; DRB104,13 | 145 | NT |  | A0101 | 0.09 |
| $NS5_{293-307}$ | WFFDENPYRTWAYH | 55 | A03,11; B35,51; C04,15; DRB101,07 | 1580 | 308 | HPYRTWAYH | B3501 | 0.4 |
|  | WFFDENHPYRTWAYH | 69 | A01,24; B35,35; C01,04; DRB104,13 | 40 | 218 | FFDENHPY | A0101 | 1.6 |
| $NS5_{297-311}$ | ENHPYRTWAYHGSYE | 55 | A03,11; B35,51; C04,15; DRB101,07 | 1280 | 358 | NHPYRTWAY | B3501 | 3 |
|  | ENHPYRTWAYHGSYE | 69 | A01,24; B35,35; C01,04; DRB104,13 | 75 | 188 | YRTWAYHGSY | B3501 | 1.7 |
|  |  |  |  |  |  |  | A0101 | 0.3 |

TABLE 2-continued

Characteristics of antigenic peptides from ZIKV (having the amino acid sequences as defined in SEQ ID NOs: 1-75) identified in this study.

| Peptide[a] | Sequence[b] | Donors | HLA[c] | SFC/million PBMC[d] 15-mer | 9-mer | Predicted epitope | Predicted HLA | Score (rank)[e] |
|---|---|---|---|---|---|---|---|---|
| | ENHPyRTWAYHGSYe | 69 | A01,24; B35,35; C01,04; DRB104,13 | 75 | 205 | RTWAYHGSY | A0101 | 0.5 |
| NS5$_{345-359}$ | TDTTPYGQQRVFKEK | 33 | A24,24; B15,35; C01,03; DRB104,04 | 1315 | 395 | TPYGQQRVF | B3531 | 0.7 |
| | | 55 | A03,11; B35,51; C04,15; DRB101,07 | 2095 | 523 | | B3501 | 0.3 |
| | | 69 | A01,24; B35,35; C01,04; DRB104,13 | 785 | 763 | | | |
| NS5$_{425-439}$ | AVNDPRFWALVDKE | 28 | A02,29; B40,44; C03,16; DRB104,07 | 150 | 100 | AVNDPRFWALVDK | A0301 | 1.1 |
| | | 55 | A03,11; B35,51; C04,15; DRB101,07 | 120 | 125 | | A1101 | 0.6 |
| | | 56 | A02,02; B15,18; C05,07; DRB103,11 | 90 | 240 | | | |
| NS5$_{461-475}$ | KKQGEFGKAKGSRAI | 28 | A02,29; B40,44; C03,16; DRB104,07 | 300 | NT | KKQGEFGKAKGSRAI | DRB10701 | 32 |
| | | 53 | A23,31; B40,44; C01,04; DRB107,08 | 105 | NT | GEFGKAKGSRAI | B4002 | 0.7 |
| NS5$_{473-487}$ | RAIWYMWLGARFLEF | 28 | A02,29; B40,44; C03,16; DRB104,07 | 210 | NT | YMWLGARFL | A0217 | 0.03 |
| | | 55 | A03,11; B35,51; C04,15; DRB101,07 | 295 | NT | AIWYMWLGAR | A0301 | 1.3 |
| | | | | | | RAIWYMWLGARFLEF | DRB10701 | 16 |
| NS5$_{546-560}$ | RFDLENEALITNQME | 28 | A02,29; B40,44; C03,16; DRB104,07 | 245 | NT | NEALITNQM | B4002 | 0.8 |
| | | 53 | A23,31; B40,44; C01,04; DRB107,08 | 190 | NT | | B4403 | 0.6 |
| | | 66 | A02,03; B39,40; C03,07; DRB108,15 | 80 | NT | | B3901 | 1.8 |
| NS5$_{565-579}$ | LALAIIKYTYQNKVV | 28 | A02,29; B40,44; C03,16; DRB104,07 | 240 | NT | LALAIIKYTY | A2902 | 0.5 |
| | | 53 | A23,31; B40,44; C01,04; DRB107,08 | 120 | NT | ALAIIKYTY | A2902 | 0.25 |
| | | 56 | A02,02; B15,18; C05,07; DRB103,11 | 150 | NT | LALAIIKYTY | B1517 | 1.2 |
| NS5$_{605-619}$ | QVVTYALNTFTNLVV | 33 | A24,24; B15,35; C01,03; DRB104,04 | 240 | NT | TYALNTFTNL | A24:02 | 0.09 |
| | | 59 | A03,24; B35,40; C01,03; DRB104,04 | 50 | 42 | YALNTFTNL | B35:43 | 0.4 |
| | | | | | | | B35:31 | 0.25 |

\* The position of peptides were determined according to NCBI Reference Sequence YP_002790881.1;
† The underlined and in bold sequence correspond to the 9-mer peptide tested;
‡ The common alleles between donors are underlined and in bold;
§ Cumulative SFC/million PBMC; NT, not tested;
¶ Calculated using NetMHCpan 3.0 and NetMHCIIpan3.1 servers: for MHC class I, strong binders <0.5, weak binders <2.

Figure 2A:
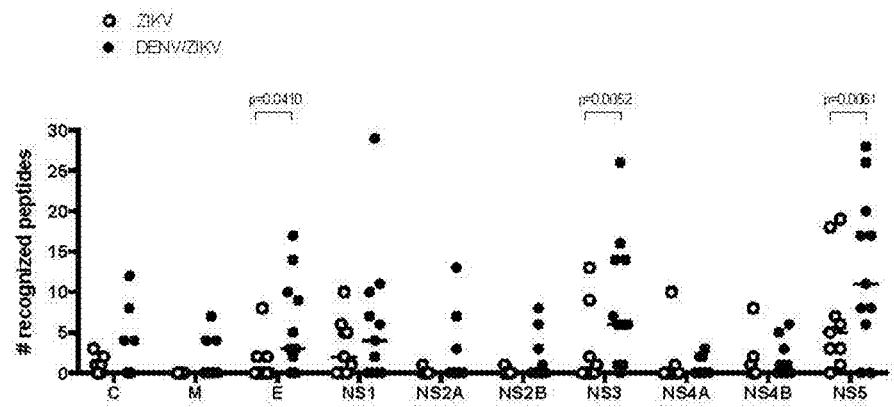
FIG. 2A-D. ZIKV donors with previous DENV infection reveal a broader T-cell response with a higher magnitude. (2A) Breadth and (2B) magnitude of responses in ZIKV and DENV/ZIKV donors. Each dot represents one donor (open circles, ZIKV donors; filled circles, DENV/ZIKV donors) and the bars represent the median value for each group of donors. The P values were calculated using the nonparametric two-tailed Mann-Whitney test. Frequency of responses against individual peptides, per donor, in ZIKV (2C) and DENV/ZIKV (2D) donors. Each dot represents one peptide. The bars represent the median response for each donor.
Figure 2B:
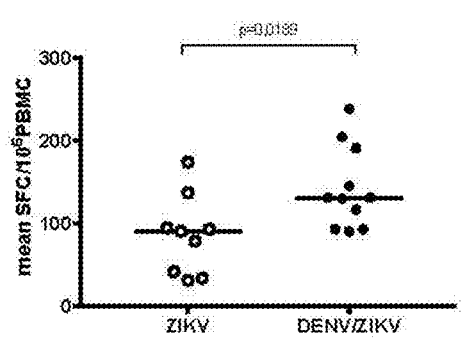
Figure 2C:
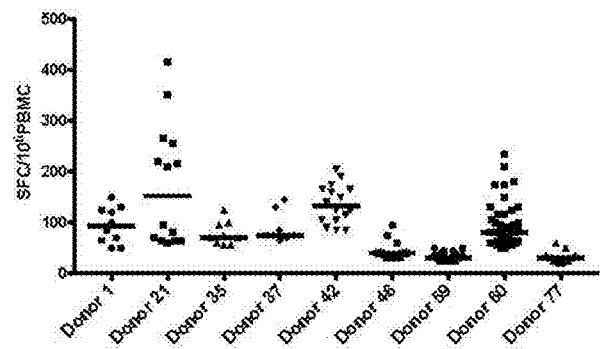
Figure 2D:
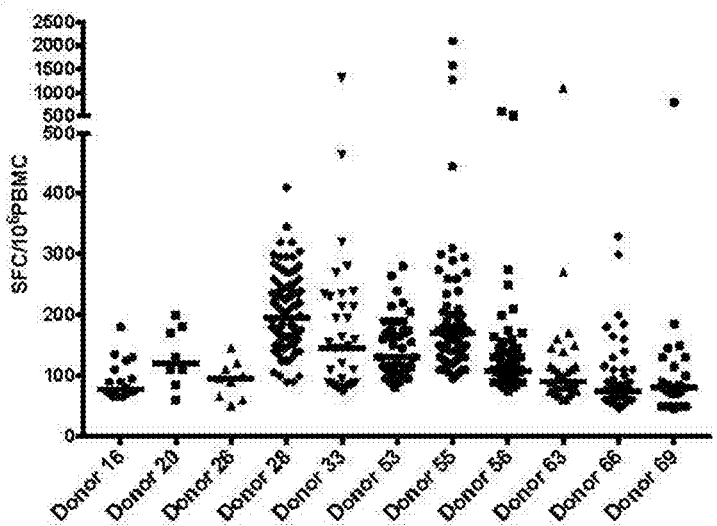

Broader Responses with a Higher Magnitude in Donors with Previous DENV Infection Given the ZIKV-specific antibody response against NS1 and the low level of CD4 T-cell cross-reactivity between DENV and ZIKV against the E and NS1 proteins (Stettler K, et al. 2016, Science 353(6301):823-826), the inventors compared, among the immunodominant epitopes, the T-cell responses in PBMCs from ZIKV donors with those from DENV/ZIKV donors. First, comparison of the frequency of responding T cells in ZIKV and DENV/ZIKV donors underlined the higher magnitude of response in DENV/ZIKV donors, relative to ZIKV donors (FIGS. 1B and 1C). The number of stimulating peptides per donor, as well as the average response per donor differed in these two groups, with a significantly broader response and a higher magnitude of response in donors with previous DENV infection (FIG. 2A, left and right panels). To determine whether this difference concerned only a small number of peptides that elicited a stronger response in each donor, or if it concerned the majority of the peptides, the inventors plotted the frequency of responses against the different peptides, per donor, in the two different groups. As shown in FIG. 2B, two out of nine individuals among the ZIKV donors revealed a median response higher than 100 SFC/million cells, whereas six out of eleven DENV/ZIKV donors developed this strong response, which was also directed against a higher number of peptides. This result revealed the activation of a higher frequency of T cells against ZIKV peptides, with a higher magnitude of response, in donors previously infected with DENV, in comparison with naïve donors. This strongly argued for the existence of cross-reactive T cells, these T cells being primed during the initial infection with DENV and expanded thereafter during the following infection with ZIKV, as shown recently in mice after sequential infection with DENV and ZIKV (Wen J, et al. 2017, *Nat Microbiol* 2:17036).

DENV/ZIKV-Cross-Reactive T Cells Mainly Target the NS5 Protein

Figure 3A:
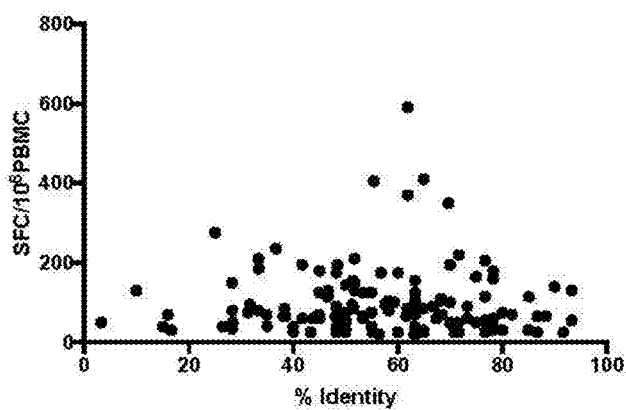
FIG. 3A-B. Comparison of the magnitude of response and sequence identity with DENV in ZIKV and DENV/ZIKV donors. Each dot represents the cumulative response of different donors against one peptide. Percentages represent the mean identity value between the sequences of ZIKV and the 4 DENV serotypes. (3A) peptides inducing a response in ZIKV donors. (3B) peptides inducing a response in DENV/ZIKV donors.
Figure 3B:
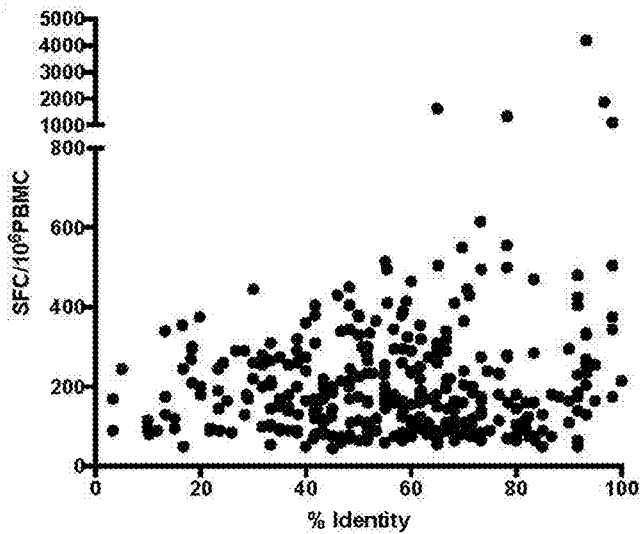
Figure 5:
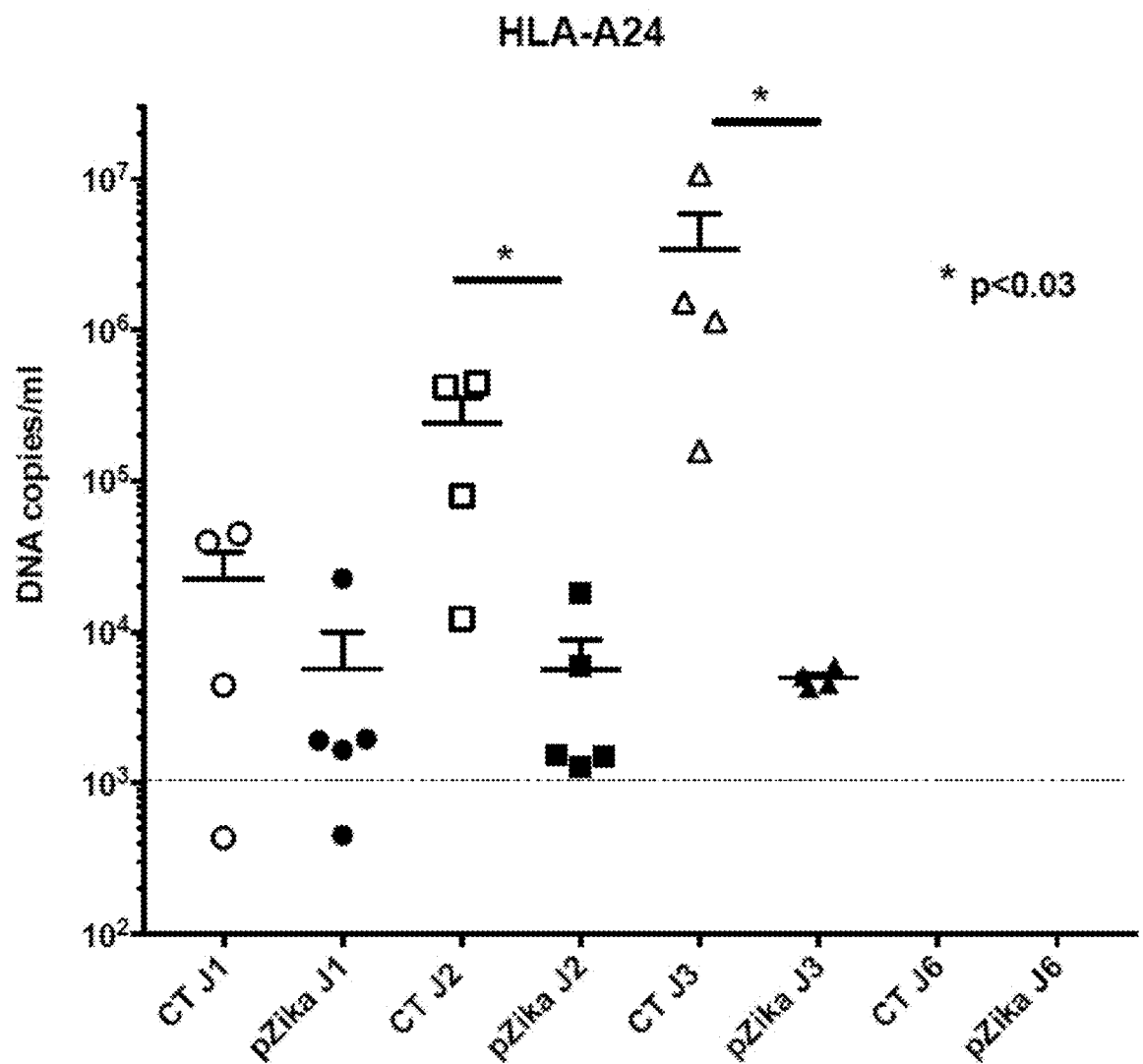
FIG. 5. HLA-A*2402 transgenic mice were immunized by intradermal injections and in vivo electroporation (prime with 2×50 µg DNA at day 0, and boost with 2×50 µg DNA at day 21) with the plasmid DNA coding for a chimeric polyepitope of ZIKV. Said chimeric polyepitope of ZIKV had the amino acid sequence of SEQ ID NO: 99. The nucleotide sequence of the polynucleotide encoding said chimeric polyepitope was as defined in SEQ ID NO: 124. Fourteen days after the boost, immunized mice were transiently depleted for IFN alpha response by intraperitoneal injection with 2 mg anti-IFNAR antibody (MAR1-5A3) and virus inoculation was performed 24 h after treatment with anti-IFNAR antibody. For virus inoculation, mice received intra-peritoneal injection of the French Guyana strain FG15 of ZIKV, using $10^3$ pfu per mouse, and viremia was quantified by qRT-PCR at days 1, 2, 3 and 6 after virus inoculation. Four mice were used as control mice (electroporation with an empty vector) and 5 mice were vaccinated with the pZIKV construct (electroporation with the plasmid DNA coding for the chimeric polyepitope of ZIKV). The electroporation settings, using the AgilePulse apparatus (BTX, Harvard apparatus) consisted of 3 Voltage groups: including the first one with 450V, a pulse length of 50 microseconds, a pulse interval of 0.2 microseconds and 1 pulse, the second one with 450V, a pulse length of 50 microseconds, a pulse interval of 50 microseconds and 1 pulse, and a third one with 110V, a pulse length of 10 milliseconds, a pulse interval of 20 milliseconds and 8 pulses.

To identify more specifically ZIKV-specific peptides and DENV/ZIKV cross-reactive peptides, the inventors compared the sequences of the most immunodominant epitopes recognized by both types of donors. As shown in FIG. 2A and Table 3, NS1 and NS3 proteins contained a high proportion of peptides that elicited strong responses in both ZIKV and DENV/ZIKV donors, whereas the E protein and to a higher extent the NS5 protein contained a majority of peptides inducing a strong response only in DENV/ZIKV donors. This suggested that the NS1 and NS3 proteins contained more ZIKV-specific epitopes, whereas the NS5 protein contained more epitopes shared by DENV and ZIKV and recognized by cross-reactive T cells. Strikingly, most of the peptides recognized only by DENV/ZIKV donors exhibited high degree of identity with the four DENV serotypes. For instance, in the NS1 protein, two out of the five epitopes that induced a response in ZIKV donors revealed a sequence identity higher than 60% with the four DENV serotypes, whereas eight out of the eleven epitopes in the NS5 protein that induced a strong response in DENV/ZIKV donors showed a sequence identity higher than 66.7% with the four DENV serotypes (Table 3). To determine whether the increased magnitude of response was correlated with the recognition of peptides having a higher sequence identity with DENV, the inventors plotted the cumulative responses for each peptide against the percentage of identity between DENV and ZIKV sequences. Among the ZIKV donors, only four ZIKV peptides with about 60% identity with DENV could elicit a response higher than 300 SFC per million cells, whereas twenty-one ZIKV peptides with at least 70% identity with DENV induced this strong response in DENV/ZIKV donors (FIG. 3); the four peptides inducing the strongest T-cell response in these donors shared the highest sequence identity with DENV. Altogether, these data strongly supported the activation of cross-reactive T cells induced after DENV and ZIKV infections, which recognized common epitopes between DENV and ZIKV, and dominated the T-cell response against ZIKV.

TABLE 3

Immunodominant epitopes in ZIKV and DENV/ZIKV donors (having the amino acid sequences as defined in SEQ ID NOs: 17, 25, 46, 48, 52, 57, 62, 64, 67 and 76-93)

| | | ZIKV | | DENV/ZIKV | | % Identity | | | |
|---|---|---|---|---|---|---|---|---|---|
| Peptide[a] | Sequence | Donors | SFC/million PBMC[b] | Donors | SFC/million PBMC[b] | DENV1 | DENV2 | DENV3 | DENV4 |
| $C_{49-63}$ | AILAFLRFTAIKPSL | 60 | 60 | 28, 63 | 365 | 60.0% | 53.3% | 60.0% | 40.0% |
| $E_{67-81}$ | DMASDSRCPTQGEAY | | | 33 | 465 | 66.7% | 53.3% | 66.7% | 53.3% |
| $E_{87-101}$ | DTQYVCKRTLVDRGW | | | 56 | 505 | 66.7% | 53.8% | 73.3% | 66.7% |
| $NS1_{19-33}$ | VFVYNDVEAWRDRYK | 21, 46, 60 | 195 | 28, 56 | 380 | 46.7% | 33.3% | 46.7% | 40.0% |
| $NS1_{55-69}$ | CGISSVSRMENIMWR | 35, 46 | 125 | 56 | 275 | 67.1% | 66.3% | 60.0% | 60.0% |
| $NS1_{91-105}$ | GSVKNPMWRGPQRLP | 21, 35, 46, 60 | 275 | 28 | 165 | 13.3% | 33.3% | 20.0% | 33.3% |
| $NS1_{107-121}$ | PVNELPHGWKAWGKS | | | 28, 53 | 430 | 40.0% | 46.7% | 46.7% | 50.5% |
| $NS1_{147-161}$ | HRAWNSFLVEDHGFG | 46 | 40 | 33, 53 | 445 | 66.7% | 73.3% | 66.7% | 76.2% |
| $NS1_{163-177}$ | FHTSVWLKVREDYSL | 46 | 35 | 20, 28, 55 | 450 | 46.7% | 46.3% | 53.3% | 46.7% |
| $NS1_{195-209}$ | HSDLGYWIESEKNDT | | | 28, 33 | 615 | 80.0% | 73.3% | 66.2% | 73.3% |
| $NS2B_{117-131}$ | AAGAWYVYVKTGKRS | | | 55 | 445 | 33.3% | 33.3% | 26.7% | 26.7% |
| $NS3_{131-145}$ | PAGTSGSPILDKCGR | 21, 42 | 405 | 26, 55, 63 | 495 | 53.3% | 60.8% | 53.3% | 54.3% |
| $NS3_{143-157}$ | CGRVIGLYGNGVVIK | 21 | 350 | 20, 55, 63, 66 | 550 | 60.0% | 66.7% | 72.3% | 80.0% |
| $NS3_{311-325}$ | AAIFMTATPPGTRDA | | | 28, 33 | 470 | 80.0% | 80.0% | 93.3% | 80.0% |
| $NS5_{13-27}$ | KARLNQMSALEFYSY | | | 55, 69 | 405 | 53.3% | 46.7% | 53.3% | 40.0% |
| $NS5_{293-307}$ | WFFDENHPYRTWAYH | | | 55, 69 | 1620 | 66.7% | 66.7% | 60.0% | 66.7% |
| $NS5_{297-311}$ | ENHPYRTWAYHGSYE | | | 55, 69 | 1330 | 80.0% | 80.0% | 73.3% | 80.0% |
| $NS5_{325-339}$ | VVRLLSKPWDVVTGV | | | 28, 55, 66 | 495 | 73.3% | 80.0% | 73.3% | 66.7% |
| $NS5_{345-359}$ | TDTTPYGQQRVFKEK | | | 33, 55, 69 | 4195 | 93.3% | 93.3% | 93.3% | 93.3% |

TABLE 3-continued

Immunodominant epitopes in ZIKV and DENV/ZIKV donors (having the amino acid sequences as defined in SEQ ID NOs: 17, 25, 46, 48, 52, 57, 62, 64, 67 and 76-93)

| Peptide[a] | Sequence | ZIKV Donors | ZIKV SFC/million PBMC[b] | DENV/ZIKV Donors | DENV/ZIKV SFC/million PBMC[b] | % Identity DENV1 | DENV2 | DENV3 | DENV4 |
|---|---|---|---|---|---|---|---|---|---|
| $NS5_{373-387}$ | QVMSMVSSWLWKELG | 60 | 130 | 55, 66, 69 | 340 | 40.0% | 53.3% | 46.7% | 46.7% |
| $NS5_{461-475}$ | KKQGEFGKAKGSRAI | | | 28, 53 | 405 | 93.3% | 93.3% | 93.3% | 86.7% |
| $NS5_{465-479}$ | EFGKAKGSRAIWYMW | | | 28, 53, 55, 56 | 1085 | 100.0% | 100.0% | 100.0% | 93.3% |
| $NS5_{473-487}$ | RAIWYMWLGARFLEF | | | 28, 55 | 505 | 100.0% | 100.0% | 93.3% | 100.0% |
| $NS5_{481-495}$ | GARFLEFEALGFLNE | | | 28, 53, 56, 63 | 1870 | 93.3% | 100.0% | 93.3% | 100.0% |
| $NS5_{546-560}$ | RFDLENEALITNQME | | | 28, 53, 66 | 515 | 60.0% | 47.1% | 53.3% | 60.0% |
| $NS5_{573-586}$ | TYQNKVVKVLRPAEK | | | 28, 53, 56 | 615 | 72.9% | 66.7% | 73.3% | 80.0% |
| $NS5_{849-863}$ | CGSLIGHRPRTTWAE | 60 | 90 | 33, 55 | 340 | 66.7% | 66.7% | 66.7% | 66.7% |

† Cumulative SFC/million PBMC
\* The position of peptides were determined according to NCBI Reference Sequence YP_002790881.1

In this study, using PBMCs from ZIKV-infected human blood donors, the inventors identified numerous T-cell epitopes that were specific to ZIKV or shared between DENV and ZIKV. While the DENV-specific T-cell responses are predominantly directed against NS3, NS4B and NS5, the response against ZIKV mainly targeted epitopes in the NS1, NS3 and NS5 proteins. The stronger and broader IFN-γ response against peptides from the NS5 protein, observed in donors previously infected with DENV, led the inventors to postulate that this region contained more peptides recognized by cross-reactive T cells, whereas the NS1 protein was preferentially targeted by ZIKV-specific T cells. These data were consistent with the higher percentage of identity observed between ZIKV and DENV sequences in the NS5 protein, in comparison with the NS1 protein. In addition to its sequence identity, the high NS1 secretability observed with the Asian lineages of ZIKV (Liu Y, et al. 2017, Nature 545 (7655): 482-486) could also explain the higher frequency of NS1-specific T cells induced in ZIKV-infected donors, in comparison with the frequency of NS1-specific T cells observed in DENV-infected donors (Weiskopf D, et al. 2013, Proc Natl Acad Sci USA 110(22):E2046-2053).

For several epitopes, the 15-mer or 9-mer peptides matched epitopes recently identified in transgenic mice expressing human HLA molecules, thus confirming the class I allele restriction for this peptide. This was the case for 15-mer peptide VARVSPFGGLKRLPA (having the amino acid sequence as defined in SEQ ID NO: 92) inducing a response in a donor expressing the HLA-B*0702 allele (data not shown), which contained the C25-35 peptide SPFGGLKRLPA (having the amino acid sequence as defined in SEQ ID NO: 93) shown to elicit a significant response in HLA-B*0702 transgenic mice infected with ZIKV (Wen J, et al. 2017, Nat Microbiol 2:17036). The same correlations were established with NS3 (FPDSNSPIM, having the amino acid sequence as defined in SEQ ID NO: 94), NS4B (RGSY-LAGASLIYTVT, having the amino acid sequence as defined in SEQ ID NO: 95) and NS5 (NQMSALEFYSY, having the amino acid sequence as defined in SEQ ID NO: 96) peptides that induced a strong response in human donors expressing the HLA-B*0702 and HLA-A*0101 alleles, respectively (data not shown and Table 2), and in transgenic mice expressing these alleles (Wen J, et al. 2017, Nat Microbiol 2:17036). In other cases, the epitopes identified in HLA-B*0702 and HLA-A*0101 transgenic mice were also identified in responding donors that nevertheless did not express these alleles, such as the $NS3_{219-233}$ peptide (having the amino acid sequence as defined in SEQ ID NO: 28) (Table 2) and the $NS1_{19-33}$ (having the amino acid sequence as defined in SEQ ID NO: 78) or the $NS5_{13-27}$ (having the amino acid sequence as defined in SEQ ID NO: 46) peptides (Table 3), which elicited a response in donors that expressed neither of the two alleles, HLA-B*0702 or HLA-A*0101. For these donors, one possibility could be that the epitope identified in transgenic mice had a higher affinity for a human HLA allele different from the allele expressed by the transgenic mice, or that the 15-mer peptide contained another epitope that bound to a different allele. Binding studies with 9-mer epitopes and HLA class I stabilization assays using TAP-deficient cells should discriminate between these possibilities.

The inventors also reported the identification of several peptides that shared common sequences with DENV and were preferentially targeted by cross-reactive T cells, after DENV and ZIKV infection. Among these peptides, the $NS5_{293-307}$ (having the amino acid sequence as defined in SEQ ID NO: 48) and $NS5_{297-311}$ (having the amino acid sequence as defined in SEQ ID NO: 52) peptides contained the amino acid sequence HPYRTWAYH (having the amino acid sequence as defined in SEQ ID NO: 49), which shared seven amino acids with an epitope previously identified in Pacific Islanders infected with DENV1 (Imrie A, et al. 2007, J. Virol. 81(18):10081-10091). Similarly, the NS5325-339 (having the amino acid sequence as defined in SEQ ID NO: 86) peptide contained the amino acid sequence KPWDWTGV (having the amino acid sequence as defined in SEQ ID NO: 97), which was also 66.7% identical to the epitope KPWDVIPMV (having the amino acid sequence as defined in SEQ ID NO: 98) identified in these individuals infected with DENV1 (Imrie A, et al. 2007 *J. Virol.* 81(18): 10081-10091). Finally, the $NS5_{345-359}$ (having the amino acid sequence as defined in SEQ ID NO: 58), $NS5_{465-479}$ (having the amino acid sequence as defined in SEQ ID NO: 88) and $NS5_{481-495}$ (having the amino acid sequence as defined in SEQ ID NO: 89) peptides inducing the strongest response in DENV/ZIKV donors (Table 3) also contained 9-mer epitopes that were previously identified in DENV-infected individuals (Weiskopf D, et al. 2015, *J. Virol.* 89(1):120-128). Altogether, these data revealed the activation of DENV/ZIKV cross-reactive T cells that dominated the response following sequential DENV and ZIKV infections. Notably, although these cross-reactive peptides exhibited a high degree of sequence identity with DENV and could stimulate a T-cell response after DENV infection, these peptides did not induce a response after primary infection with ZIKV, suggesting that these peptides were immunodominant in the context of DENV but not in the context of ZIKV infection. This result was expected, as the immunodominance of an epitope or its relative abundance depends on the other epitopes expressed by the protein. This was also in agreement with previous observations showing that epitope production correlated with cleavability of flanking residues expressed in the protein sequence (Zhang S C, et al. 2012, *J. Immunol.* 188(12):5924-5934). Importantly, for these cross-reactive epitopes, the absence of a T-cell response in ZIKV-infected donors was not simply due to the absence of the presenting HLA allele in this population, as most of the alleles expressed in responding DENV/ZIKV donors were also expressed in ZIKV donors (Table 1). This is what the inventors observed for the $NS5_{13-27}$ (having the amino acid sequence as defined in SEQ ID NO: 46), $NS5_{293-307}$ (having the amino acid sequence as defined in SEQ ID NO: 48), $NS5_{345-359}$ (having the amino acid sequence as defined in SEQ ID NO: 57) and $NS5_{546-560}$ (having the amino acid sequence as defined in SEQ ID NO: 67) epitopes, predicted to be strong binders to the HLA-B*3501 and HLA-B*4002 alleles, respectively, that were frequently expressed by ZIKV donors (Table 2 and FIG. 3). Altogether, these results showed that, in the case of initial ZIKV infection, there was a preferential recognition of ZIKV-specific epitopes, whereas there was a more frequent and stronger T-cell response against cross-reactive epitopes after heterologous DENV/ZIKV infection. Interestingly, the strong T-cell response observed in DENV/ZIKV donors against these NS5 epitopes relied primarily on donors that expressed the HLA-B*3501 allele, an allele associated with high magnitude responses against DENV, and a stronger protection against DENV infection and disease (Weiskopf D, et al. 2013, *Proc Natl Acad Sci USA* 110(22):E2046-2053). As all blood samples were obtained from donors with asymptomatic ZIKV infection history, the inventors could not relate the strength of the ZIKV-specific T-cell response obtained in HLA-B*3501 donors to the protection against the disease. Further studies with more subjects with a higher susceptibility to disease following primary ZIKV infection are required to determine whether, as for DENV, there is an HLA-linked protective role for T cells in ZIKV infection. Likewise, it would also be important to compare disease severity in donors having or not experienced a previous DENV infection, to determine whether cross-reactive T cells induced after DENV infection could mediate a better protection against ZIKV infection and disease, as recently suggested in mice (Wen J, et al. 2017, *Nat Microbiol* 2:17036; Elong Ngono A, et al. 2017, *Cell host & microbe* 21(1):35-46). As both CD4+ and CD8+ T cells were shown to contribute to protection against DENV infection, a comprehensive analysis of MHC class II-restricted response is needed to determine the role of CD4 in ZIKV infection and disease protection. Finally, further phenotypic analyses of ZIKV-specific T cells, in asymptomatic or symptomatic donors will help in defining correlates of protection in natural immunity and vaccination against ZIKV infection and disease. It will be particularly important to determine whether, as for DENV-specific T cells, strong responses against ZIKV-specific peptides are more frequent in specific HLA alleles and are associated with multifunctionality (Weiskopf D, et al. 2013, *Proc Natl Acad Sci USA* 110(22): E2046-2053).

In conclusion, while many studies have focused on the antibody response against ZIKV, more specifically the identification of B cell epitopes shared between ZIKV and DENV, little is known regarding the role of T cells in the control of ZIKV infection. Using PBMCs from blood donors with recent history of ZIKV infection, seropositive or not for DENV, the inventors established the first map of the distribution of ZIKV T-cell epitopes by screening the complete proteome by interferon (IFN)-γ enzyme-linked immunospot (ELISPOT) assay. The inventors showed that the non-structural proteins NS1, NS3 and NS5 contained most of the immunodominant peptides that induced a strong T-cell response. The inventors also showed that the NS5 protein contained many epitopes shared by both viruses, and which induced the highest response following DENV and ZIKV infections. Strikingly, donors with a history of DENV infection revealed a substantial response against peptides previously identified as DENV CD8+ T-cell epitopes. The strongest T-cell responses observed in these donors corresponded to sequences with a high level of amino acid identity with the four DENV serotypes, suggesting the activation of cross-reactive T cells. These results have crucial implications for future ZIKV and DENV vaccines and provide new opportunities to study the role of ZIKV-specific and DENV/ZIKV shared T-cell epitopes in the induction of long-term immunity against these viruses.

Poly-ZIKV DNA Vaccination in Mice

DNA immunization will be performed using plasmid coding for the chimeric polyepitope and electroporation, with 2×50 µg DNA, at 3 weeks interval and challenge 15 days after the boost with the virus (intraperitoneal injection of ZIKV with $10^3$ pfu/mouse).

DNA vaccination with plasmids and electroporation (EP) will be performed as follows:

For vaccination, two injections of 25 μl each of DNA at 2 mg/ml will be performed by intradermal inoculation in the back, followed immediately by electroporation using AgilePulse apparatus (BTX Harvard Apparatus).

The electroporation procedure will consist of 3 voltage groups:

Group 1: 450V, pulse length 50 μsec, pulse interval of 0.2 μsec, Nb pulses: 1;

Group 2: 450V, pulse length 50 μsec, pulse interval of 50 μsec, Nb pulses: 1;

Group 3: 110V, pulse length 10 msec, pulse interval of 20 msec, Nb pulses: 8.

At day −1 before the challenge with ZIKV, intraperitoneal injection with 2 mg anti-IFNAR antibody (MAR1-5A3) will be performed to transiently block the IFN type I response.

The viremia will be quantified by qRT-PCR in plasma samples from day 1 to day 6 after the challenge.

DNA Vaccination in Non-Human Primates (Indian Rhesus Macaques Monkeys)

DNA vaccination will be performed by 2 intramuscular injections with 1 mg plasmid coding for the chimeric polyepitope of ZIKV, at 0 and 4 weeks, followed by a challenge 4 weeks later by inoculating subcutaneously $10^4$ pfu ZIKV, as previously described (Dowd, K. A., et al. *Science* 2016, 354, 237-240).

PBMC will be collected at day 0 (before the prime), day 7 after the prime, then at day 35 (one week after the boost) and day 60 (before challenge with ZIKV), to analyse the T cell response (IFN-γ and TNF-α) by ELISpot against overlapping peptides covering the whole chimeric polyepitope sequence. The number and phenotype of Monocytes CD14, DCs, T cells, B cells, and NK cells, and the cytokine profile of T cells (CD8 T cells) will be analysed by intracellular staining.

Blood samples will also be collected at day 0 (prior to immunization), day 14, day 28 (prior to boost) and day 56 (prior to challenge) to determine neutralizing Ab titres by Focus Reduction Neutralization Titres (FRNT).

Plasma samples will be tested for quantification of viremia by qRT-PCR, daily from day 56 (prior to challenge) until day 66.

Alternate Protocol Using DNA Vaccination with Plasmids Expressing Cytokines, as Genetic Adjuvants to Remove the Electroporation Recent studies have shown that co-administration of plasmids expressing T cell epitopes with plasmids expressing either IL-12, or GM-CSF, or a combination of both IL-12 and GM-CSF improves the T cell response, sufficiently to remove the need for electroporation (EP) (Boyer, J. D., et al. *J Med Primatol* 2005, 34, 262-270; Suschak, J. J., et al. *The Journal of infectious diseases* 2018; Suschak, J. J., et al. *Antiviral research* 2018, 159, 113-121).

The inventors will thus assess the effect of IL-12 and GM-CSF DNA immunization combined with Poly-ZIKV DNA immunization on the magnitude of T cell response against ZIKV peptides and the immune protection against ZIKV infection in Rhesus monkeys.

The invention claimed is:

1. A pharmaceutical composition comprising polynucleotide encoding a chimeric polyepitope an adjuvant and/or a pharmaceutically acceptable vehicle, wherein said chimeric polyepitope comprises:
(i) at least the following T-cell epitopes of (a) and (b), or (ii) at least the following T-cell epitopes of (a) and (c), or (iii) at least the following T-cell epitopes of (b) and (c):
(a) a T-cell epitope of the non-structural (NS) NS1 protein of a Zika virus (ZIKV) comprising or consisting of an amino acid sequence selected from the group consisting of SEQ ID NOs: 10-12, 14, 15, 17-19, 23, 24 and 78-83,
(b) a T-cell epitope of the NS3 protein of a ZIKV comprising or consisting of an amino acid sequence selected from the group consisting of SEQ ID NOs: 28, 29, 31, 33-35, 84 and 85,
(c) a T-cell epitope of the NS5 protein of a ZIKV comprising or consisting of an amino acid sequence selected from the group consisting of SEQ ID NOs: 46, 48-50, 52-55, 57-60, 62, 64, 67, 69, 72, 73 and 86-91,
or a T-cell epitope variant thereof, which differs from the original amino acid sequence of the T-cell epitope of (a), (b) or (c) by point mutation of one or more amino acid residues and which has at least 90% sequence identity or more than 95% sequence identity or 99% sequence identity with said original sequence.

2. The pharmaceutical composition of claim 1, wherein said chimeric polyepitope comprises at least the T-cell epitopes of (a), (b) and (c), or the T-cell epitope variant thereof.

3. The pharmaceutical composition of claim 1, wherein said chimeric polyepitope consists of (i) the T-cell epitopes of (a) and (b), or (ii) the T-cell epitopes of (a) and (c), or (iii) the T-cell epitopes of (b) and (c), or (iv) the T-cell epitopes of (a), (b) and (c), or the T-cell epitope variant thereof.

4. The pharmaceutical composition of claim 1, wherein the T-cell epitope of (a) comprises or consists of the amino acid sequence selected from the group consisting of SEQ ID NOs: 17, 23 and 78-83, the T-cell epitope of (b) comprises or consists of the amino acid sequence selected from the group consisting of SEQ ID NOs: 31, 33, 84 and 85, and the T-cell epitope of (c) comprises or consists of the amino acid sequence selected from the group consisting of SEQ ID NOs: 46, 48, 52, 57, 62, 64, 67 and 86-91.

5. The pharmaceutical composition of claim 1, wherein the T-cell epitope of (a) comprises or consists of the amino acid sequence of SEQ ID NOs: 11, 12, 17-19, 23, 24, 78, 80 and 83, the T-cell epitope of (b) comprises or consists of the amino acid sequence of SEQ ID NOs: 28, 31, 33, 34, 84 and 85, and the T-cell epitope of (c) comprises or consists of the amino acid sequence of SEQ ID NOs: 48-50, 52-55, 57, 58, 60, 62, 67, 88, 89 and 90.

6. The pharmaceutical composition of claim 1, wherein the chimeric polyepitope further comprises at least one T-cell epitope of a ZIKV protein selected from the group consisting of:
(i) a T-cell epitope of the C protein of a ZIKV comprising or consisting of an amino acid sequence selected from the group consisting of SEQ ID NOs: 1, 2, 4-6 and 75,
(ii) a T-cell epitope of the E protein of a ZIKV comprising or consisting of an amino acid sequence selected from the group consisting of SEQ ID NOs: 7, 76 and 77,
(iii) a T-cell epitope of the NS2B protein of a ZIKV comprising or consisting of the amino acid sequence of SEQ ID NO: 25,
(iv) a T-cell epitope of the NS4A protein of a ZIKV comprising or consisting of the amino acid sequence of SEQ ID NO: 36, and
(v) a T-cell epitope of the NS4B protein of a ZIKV comprising or consisting of the amino acid sequence selected from the group consisting of SEQ ID NOs: 40-43.

7. The chimeric polyepitope according to claim 6, wherein said at least one T-cell epitope of a ZIKV protein is selected from the group consisting of:
the T-cell epitope of the C protein of a ZIKV comprising or consisting of an amino acid sequence selected from the group consisting of SEQ ID NOs: 1, 2, 4-6 and 75, and
the T-cell epitope of the NS4B protein of a ZIKV comprising or consisting of the amino acid sequence selected from the group consisting of SEQ ID NOs: 40-43.

8. The pharmaceutical composition of claim 1, wherein the chimeric polyepitope has an amino acid sequence of SEQ ID NO: 99.

9. The pharmaceutical composition of claim 1, which elicits a human leukocyte antigen (HLA)-restricted CD8+ and/or CD4+ T cell response (i) against ZIKV, or (ii) against ZIKV and DENV, in particular DENV serotype 1 (DENV1), DENV serotype 2 (DENV2), DENV serotype 3 (DENV3) and DENV serotype 4 (DENV4).

10. The pharmaceutical composition of claim 1, wherein the T-cell epitopes are assembled in a fusion polypeptide.

11. The pharmaceutical composition of claim 1, wherein the ZIKV is from the African lineage, or from the Asian lineage.

12. The pharmaceutical composition of claim 1, wherein said composition is formulated for an administration by a route selected from the group consisting of subcutaneous (s.c.), intradermal (i.d.), intramuscular (i.m.), intraperitoneal (i.p.) and intravenous (i.v.) injection.

13. The pharmaceutical composition of claim 11, formulated for administration in a prime-boost administration regime.

14. A method of (i) preventing a Zika virus (ZIKV) infection in a human subject or (ii) preventing ZIKV and Dengue virus (DENV) infections in a human subject, comprising administering the pharmaceutical composition of claim 1 to the human subject.

15. The method of preventing a ZIKV infection in a human subject according to claim 14, wherein the T-cell epitopes are ZIKV-specific epitopes comprising or consisting of an amino acid sequence selected from the group consisting of SEQ ID NOs: 1, 2, 5, 10, 11, 19, 27, 31, 40-43, 46, 72, 73, 75, 78-80, 82, 84, 85, 87 and 91.

16. The method of preventing ZIKV and DENV infections in a human subject according to claim 14, wherein the T-cell epitopes are ZIKV-DENV cross-reactive epitopes comprising or consisting of an amino acid sequence selected from the group consisting of SEQ ID NOs: 1, 5, 6, 12, 14, 15, 17-19, 23, 24, 27, 28, 33-35, 40, 41, 46, 48-50, 52-55, 57, 59, 60, 62, 64, 67, 69, 72, 73, 84, 85 and 86-91.

\* \* \* \* \*

UNITED STATES PATENT AND TRADEMARK OFFICE
CERTIFICATE OF CORRECTION

| | | |
|---|---|---|
| PATENT NO. | : 11,872,276 B2 | |
| APPLICATION NO. | : 17/694440 | |
| DATED | : January 16, 2024 | |
| INVENTOR(S) | : Claude Roth | |

It is certified that error appears in the above-identified patent and that said Letters Patent is hereby corrected as shown below:

In the Claims

Column 97, Line 6, Claim 13, replace "of claim 11" with "of claim 1"

Signed and Sealed this
Seventh Day of May, 2024

Katherine Kelly Vidal
*Director of the United States Patent and Trademark Office*